United States Patent
Piel et al.

(10) Patent No.: US 10,969,389 B2
(45) Date of Patent: Apr. 6, 2021

(54) METHOD TO MONITOR AND QUANTIFY INTERPHASE NUCLEAR ENVELOPE RUPTURE EVENTS

(71) Applicants: INSTITUT CURIE, Paris (FR); INSERM (INSTITUT NATIONAL DE LA SANTE ET DE LA RECHERCHE MEDICALE), Paris (FR); CENTRE NATIONAL DE LA RECHERCHE SCIENTIFIQUE, Paris (FR)

(72) Inventors: Matthieu Piel, Paris (FR); Matteo Gentili, Cambridge, MA (US); Matthew Raab, Paris (FR); Nicolas Manel, Paris (FR)

(73) Assignees: INSTITUT CURIE, Paris (FR); INSERM (INSTITUT NATIONAL DE LA SANTE ET DE LA RECHERCHE MEDICALE), Paris (FR); CENTRE NATIONAL DE LA RECHERCHE SCIENTIFIQUE, Paris (FR)

( * ) Notice: Subject to any disclaimer, the term of this patent is extended or adjusted under 35 U.S.C. 154(b) by 0 days.

(21) Appl. No.: 16/077,744

(22) PCT Filed: Feb. 17, 2017

(86) PCT No.: PCT/EP2017/053665
§ 371 (c)(1),
(2) Date: Aug. 14, 2018

(87) PCT Pub. No.: WO2017/140875
PCT Pub. Date: Aug. 24, 2017

(65) Prior Publication Data
US 2019/0033311 A1    Jan. 31, 2019

(30) Foreign Application Priority Data
Feb. 18, 2016 (EP) .................................. 16305184

(51) Int. Cl.
*G01N 33/53* (2006.01)
*G01N 33/569* (2006.01)
*G01N 33/50* (2006.01)
*A01K 67/027* (2006.01)

(52) U.S. Cl.
CPC ... *G01N 33/56966* (2013.01); *A01K 67/0278* (2013.01); *G01N 33/5035* (2013.01); *A01K 2227/105* (2013.01); *G01N 2333/9125* (2013.01)

(58) Field of Classification Search
None
See application file for complete search history.

(56) References Cited

U.S. PATENT DOCUMENTS 8,334,101 B2 * 12/2012 Latz .................. G01N 33/5035
                                                         435/7.1
2015/0343056 A1 * 12/2015 Chen ................. A61K 31/7084
                                                         424/184.1

FOREIGN PATENT DOCUMENTS

WO   WO 2010/036918    4/2010
WO   WO 2014/099824    6/2014
WO   WO 2015/069883    5/2015

OTHER PUBLICATIONS

Choubey, D. et al. "Cytoplasmic localization of the interferon-inducible protein that is encoded by the AIM2 (absent in melanoma) gene from the 200-gene family" *FEBS Letters*, May 26, 2000, pp. 38-42, vol. 474, No. 1.

Cresswell, K. S. et al. "Biochemical and growth regulatory activities of the HIN-200 family member and putative tumor suppressor protein, AIM2" *Biochemical and Biophysical Research Communications*, Jan. 14, 2005, pp. 417-424, vol. 326, No. 2.

Gentili, M. et al. "Transmission of innate immune signaling by packaging of cGAMP in viral particles" *Science*, Sep. 11, 2015, pp. 1232-1236, vol. 349, No. 6253.

Gentili, M. et al. "Transmission of innate immune signaling by packaging of cGAMP in viral particles" *Science*, Jul. 30, 2015, Supplemental Materials, pp. 1-22.

Haraguchi, T. et al. "Live cell imaging and electron microscopy reveal dynamic processes of BAF-directed nuclear envelope assembly" *Journal of Cell Science*, Aug. 1, 2008, pp. 2540-2554, vol. 121, No. 15.

Patsos, G. et al. "Restoration of absent in melanoma 2 (AIM2) induces G2/M cell cycle arrest and promotes invasion of colorectal cancer cells" *International Journal of Cancer*, 2010, pp. 1838-1849, vol. 126.

(Continued)

*Primary Examiner* — Celine X Qian
(74) *Attorney, Agent, or Firm* — Saliwanchik, Lloyd & Eisenschenk

(57) ABSTRACT

The present invention provides an in vitro method for monitoring interphase nuclear envelope rupture events in a eukaryotic cell or screening or identifying compound capable of increasing or decreasing the intensity and/or frequency of interphase nuclear envelope rupture events in a eukaryotic cell. These methods relate on a protein having a cytosolic non-nuclear localization in interphase and a non-sequence specific DNA binding activity. Interphase nuclear envelope rupture events are characterized by the presence of the protein of the invention in the nucleus of the eukaryotic cell.

7 Claims, 20 Drawing Sheets
(20 of 20 Drawing Sheet(s) Filed in Color)
Specification includes a Sequence Listing.

(56) References Cited

OTHER PUBLICATIONS

Shimi, T. et al. "Dynamic interaction between BAF and emerin revealed by FRAP, FLIP, and FRET analyses in living HeLa cells" *Journal of Structural Biology*, Jul. 1, 2004, pp. 31-41, vol. 147.
Vargas, J. D. et al. "Transient nuclear envelope rupturing during interphase in human cancer cells" *Nucleus*, Jan./Feb. 2012, pp. 88-100, vol. 3, No. 1.
Xiong, H. et al. "Dictyostelium Sun-1 Connects the Centrosome to Chromatin and Ensures Genome Stability" *Traffic*, May 1, 2008, pp. 708-724, vol. 9, No. 5.
Written Opinion in International Application No. PCT/EP2017/053665, dated Jun. 28, 2017, pp. 1-12.

* cited by examiner

J

K

A

B

A

B

C

SEQUENCE LISTING

```
<160> NUMBER OF SEQ ID NOS: 17

<210> SEQ ID NO 1
<211> LENGTH: 522
<212> TYPE: PRT
<213> ORGANISM: Homo sapiens

<400> SEQUENCE: 1

Met Gln Pro Trp His Gly Lys Ala Met Gln Arg Ala Ser Glu Ala Gly
1               5                   10                  15

Ala Thr Ala Pro Lys Ala Ser Ala Arg Asn Ala Arg Gly Ala Pro Met
            20                  25                  30

Asp Pro Thr Glu Ser Pro Ala Ala Pro Glu Ala Ala Leu Pro Lys Ala
        35                  40                  45

Gly Lys Phe Gly Pro Ala Arg Lys Ser Gly Ser Arg Gln Lys Lys Ser
    50                  55                  60

Ala Pro Asp Thr Gln Glu Arg Pro Pro Val Arg Ala Thr Gly Ala Arg
65                  70                  75                  80

Ala Lys Lys Ala Pro Gln Arg Ala Gln Asp Thr Gln Pro Ser Asp Ala
                85                  90                  95

Thr Ser Ala Pro Gly Ala Glu Gly Leu Glu Pro Pro Ala Ala Arg Glu
            100                 105                 110

Pro Ala Leu Ser Arg Ala Gly Ser Cys Arg Gln Arg Gly Ala Arg Cys
        115                 120                 125

Ser Thr Lys Pro Arg Pro Pro Gly Pro Trp Asp Val Pro Ser Pro
    130                 135                 140

Gly Leu Pro Val Ser Ala Pro Ile Leu Val Arg Arg Asp Ala Ala Pro
145                 150                 155                 160

Gly Ala Ser Lys Leu Arg Ala Val Leu Glu Lys Leu Lys Leu Ser Arg
                165                 170                 175

Asp Asp Ile Ser Thr Ala Ala Gly Met Val Lys Gly Val Val Asp His
```

```
            180                 185                 190
Leu Leu Leu Arg Leu Lys Cys Asp Ser Ala Phe Arg Gly Val Gly Leu
            195                 200                 205
Leu Asn Thr Gly Ser Tyr Tyr Glu His Val Lys Ile Ser Ala Pro Asn
            210                 215                 220
Glu Phe Asp Val Met Phe Lys Leu Glu Val Pro Arg Ile Gln Leu Glu
225                 230                 235                 240
Glu Tyr Ser Asn Thr Arg Ala Tyr Tyr Phe Val Lys Phe Lys Arg Asn
                245                 250                 255
Pro Lys Glu Asn Pro Leu Ser Gln Phe Leu Glu Gly Glu Ile Leu Ser
            260                 265                 270
Ala Ser Lys Met Leu Ser Lys Phe Arg Lys Ile Ile Lys Glu Glu Ile
            275                 280                 285
Asn Asp Ile Lys Asp Thr Asp Val Ile Met Lys Arg Lys Arg Gly Gly
            290                 295                 300
Ser Pro Ala Val Thr Leu Leu Ile Ser Glu Lys Ile Ser Val Asp Ile
305                 310                 315                 320
Thr Leu Ala Leu Glu Ser Lys Ser Ser Trp Pro Ala Ser Thr Gln Glu
                325                 330                 335
Gly Leu Arg Ile Gln Asn Trp Leu Ser Ala Lys Val Arg Lys Gln Leu
            340                 345                 350
Arg Leu Lys Pro Phe Tyr Leu Val Pro Lys His Ala Lys Glu Gly Asn
            355                 360                 365
Gly Phe Gln Glu Glu Thr Trp Arg Leu Ser Phe Ser His Ile Glu Lys
            370                 375                 380
Glu Ile Leu Asn Asn His Gly Lys Ser Lys Thr Cys Cys Glu Asn Lys
385                 390                 395                 400
Glu Glu Lys Cys Cys Arg Lys Asp Cys Leu Lys Leu Met Lys Tyr Leu
                405                 410                 415
Leu Glu Gln Leu Lys Glu Arg Phe Lys Asp Lys Lys His Leu Asp Lys
            420                 425                 430
Phe Ser Ser Tyr His Val Lys Thr Ala Phe Phe His Val Cys Thr Gln
            435                 440                 445
Asn Pro Gln Asp Ser Gln Trp Asp Arg Lys Asp Leu Gly Leu Cys Phe
450                 455                 460
Asp Asn Cys Val Thr Tyr Phe Leu Gln Cys Leu Arg Thr Glu Lys Leu
465                 470                 475                 480
Glu Asn Tyr Phe Ile Pro Glu Phe Asn Leu Phe Ser Ser Asn Leu Ile
                485                 490                 495
Asp Lys Arg Ser Lys Glu Phe Leu Thr Lys Gln Ile Glu Tyr Glu Arg
            500                 505                 510
Asn Asn Glu Phe Pro Val Phe Asp Glu Phe
            515                 520

<210> SEQ ID NO 2
<211> LENGTH: 343
<212> TYPE: PRT
<213> ORGANISM: Homo sapiens

<400> SEQUENCE: 2

Met Glu Ser Lys Tyr Lys Glu Ile Leu Leu Leu Thr Gly Leu Asp Asn
1               5                   10                  15
Ile Thr Asp Glu Glu Leu Asp Arg Phe Lys Phe Phe Leu Ser Asp Glu
            20                  25                  30
```

Phe Asn Ile Ala Thr Gly Lys Leu His Thr Ala Asn Arg Ile Gln Val
            35                  40                  45

Ala Thr Leu Met Ile Gln Asn Ala Gly Ala Val Ser Ala Val Met Lys
 50                  55                  60

Thr Ile Arg Ile Phe Gln Lys Leu Asn Tyr Met Leu Leu Ala Lys Arg
 65                  70                  75                  80

Leu Gln Glu Glu Lys Glu Lys Val Asp Lys Gln Tyr Lys Ser Val Thr
                 85                  90                  95

Lys Pro Lys Pro Leu Ser Gln Ala Glu Met Ser Pro Ala Ala Ser Ala
            100                 105                 110

Ala Ile Arg Asn Asp Val Ala Lys Gln Arg Ala Ala Pro Lys Val Ser
            115                 120                 125

Pro His Val Lys Pro Glu Gln Lys Gln Met Val Ala Gln Gln Glu Ser
        130                 135                 140

Ile Arg Glu Gly Phe Gln Lys Arg Cys Leu Pro Val Met Val Leu Lys
145                 150                 155                 160

Ala Lys Lys Pro Phe Thr Phe Glu Thr Gln Glu Gly Lys Gln Glu Met
                165                 170                 175

Phe His Ala Thr Val Ala Thr Glu Lys Glu Phe Phe Phe Val Lys Val
            180                 185                 190

Phe Asn Thr Leu Leu Lys Asp Lys Phe Ile Pro Lys Arg Ile Ile Ile
        195                 200                 205

Ile Ala Arg Tyr Tyr Arg His Ser Gly Phe Leu Glu Val Asn Ser Ala
210                 215                 220

Ser Arg Val Leu Asp Ala Glu Ser Asp Gln Lys Val Asn Val Pro Leu
225                 230                 235                 240

Asn Ile Ile Arg Lys Ala Gly Glu Thr Pro Lys Ile Asn Thr Leu Gln
                245                 250                 255

Thr Gln Pro Leu Gly Thr Ile Val Asn Gly Leu Phe Val Val Gln Lys
            260                 265                 270

Val Thr Glu Lys Lys Asn Ile Leu Phe Asp Leu Ser Asp Asn Thr
        275                 280                 285

Gly Lys Met Glu Val Leu Gly Val Arg Asn Glu Asp Thr Met Lys Cys
    290                 295                 300

Lys Glu Gly Asp Lys Val Arg Leu Thr Phe Phe Thr Leu Ser Lys Asn
305                 310                 315                 320

Gly Glu Lys Leu Gln Leu Thr Ser Gly Val His Ser Thr Ile Lys Val
                325                 330                 335

Ile Lys Ala Lys Lys Lys Thr
            340

<210> SEQ ID NO 3
<211> LENGTH: 2319
<212> TYPE: DNA
<213> ORGANISM: Artificial Sequence
<220> FEATURE:
<223> OTHER INFORMATION: human gene cGAS mutated to generate E225A and
      D227A mutations and fused with EGFP and FLAG
<220> FEATURE:
<221> NAME/KEY: CDS
<222> LOCATION: (1)..(2319)
<220> FEATURE:
<221> NAME/KEY: EGFP
<222> LOCATION: (1)..(716)
<220> FEATURE:
<221> NAME/KEY: FLAG
<222> LOCATION: (723)..(749)
<220> FEATURE:
<221> NAME/KEY: cGAS

```
<222> LOCATION: (750)..(2315)
<220> FEATURE:
<221> NAME/KEY: Mutation E225A
<222> LOCATION: (1422)..(1424)
<220> FEATURE:
<221> NAME/KEY: Mutation D227A
<222> LOCATION: (1428)..(1430)

<400> SEQUENCE: 3
```

| | | | | | | | | | | | | | | | | |
|---|---|---|---|---|---|---|---|---|---|---|---|---|---|---|---|---|
| atg | gtg | agc | aag | ggc | gag | gag | ctg | ttc | acc | ggg | gtg | gtg | ccc | atc | ctg | 48 |
| Met | Val | Ser | Lys | Gly | Glu | Glu | Leu | Phe | Thr | Gly | Val | Val | Pro | Ile | Leu | |
| 1 | | | | 5 | | | | | 10 | | | | | 15 | | |
| gtc | gag | ctg | gac | ggc | gac | gta | aac | ggc | cac | aag | ttc | agc | gtg | tcc | ggc | 96 |
| Val | Glu | Leu | Asp | Gly | Asp | Val | Asn | Gly | His | Lys | Phe | Ser | Val | Ser | Gly | |
| | | | 20 | | | | | 25 | | | | | 30 | | | |
| gag | ggc | gag | ggc | gat | gcc | acc | tac | ggc | aag | ctg | acc | ctg | aag | ttc | atc | 144 |
| Glu | Gly | Glu | Gly | Asp | Ala | Thr | Tyr | Gly | Lys | Leu | Thr | Leu | Lys | Phe | Ile | |
| | 35 | | | | | 40 | | | | | 45 | | | | | |
| tgc | acc | acc | ggc | aag | ctg | ccc | gtg | ccc | tgg | ccc | acc | ctc | gtg | acc | acc | 192 |
| Cys | Thr | Thr | Gly | Lys | Leu | Pro | Val | Pro | Trp | Pro | Thr | Leu | Val | Thr | Thr | |
| 50 | | | | | 55 | | | | | 60 | | | | | | |
| ctg | acc | tac | ggc | gtg | cag | tgc | ttc | agc | cgc | tac | ccc | gac | cac | atg | aag | 240 |
| Leu | Thr | Tyr | Gly | Val | Gln | Cys | Phe | Ser | Arg | Tyr | Pro | Asp | His | Met | Lys | |
| 65 | | | | | 70 | | | | | 75 | | | | | 80 | |
| cag | cac | gac | ttc | ttc | aag | tcc | gcc | atg | ccc | gaa | ggc | tac | gtc | cag | gag | 288 |
| Gln | His | Asp | Phe | Phe | Lys | Ser | Ala | Met | Pro | Glu | Gly | Tyr | Val | Gln | Glu | |
| | | | | 85 | | | | | 90 | | | | | 95 | | |
| cgc | acc | atc | ttc | ttc | aag | gac | gac | ggc | aac | tac | aag | acc | cgc | gcc | gag | 336 |
| Arg | Thr | Ile | Phe | Phe | Lys | Asp | Asp | Gly | Asn | Tyr | Lys | Thr | Arg | Ala | Glu | |
| | | | 100 | | | | | 105 | | | | | 110 | | | |
| gtg | aag | ttc | gag | ggc | gac | acc | ctg | gtg | aac | cgc | atc | gag | ctg | aag | ggc | 384 |
| Val | Lys | Phe | Glu | Gly | Asp | Thr | Leu | Val | Asn | Arg | Ile | Glu | Leu | Lys | Gly | |
| | 115 | | | | | 120 | | | | | 125 | | | | | |
| atc | gac | ttc | aag | gag | gac | ggc | aac | atc | ctg | ggg | cac | aag | ctg | gag | tac | 432 |
| Ile | Asp | Phe | Lys | Glu | Asp | Gly | Asn | Ile | Leu | Gly | His | Lys | Leu | Glu | Tyr | |
| 130 | | | | | 135 | | | | | 140 | | | | | | |
| aac | tac | aac | agc | cac | aac | gtc | tat | atc | atg | gcc | gac | aag | cag | aag | aac | 480 |
| Asn | Tyr | Asn | Ser | His | Asn | Val | Tyr | Ile | Met | Ala | Asp | Lys | Gln | Lys | Asn | |
| 145 | | | | | 150 | | | | | 155 | | | | | 160 | |
| ggc | atc | aag | gtg | aac | ttc | aag | atc | cgc | cac | aac | atc | gag | gac | ggc | agc | 528 |
| Gly | Ile | Lys | Val | Asn | Phe | Lys | Ile | Arg | His | Asn | Ile | Glu | Asp | Gly | Ser | |
| | | | | 165 | | | | | 170 | | | | | 175 | | |
| gtg | cag | ctc | gcc | gac | cac | tac | cag | cag | aac | acc | ccc | atc | ggc | gac | ggc | 576 |
| Val | Gln | Leu | Ala | Asp | His | Tyr | Gln | Gln | Asn | Thr | Pro | Ile | Gly | Asp | Gly | |
| | | | 180 | | | | | 185 | | | | | 190 | | | |
| ccc | gtg | ctg | ctg | ccc | gac | aac | cac | tac | ctg | agc | acc | cag | tcc | gcc | ctg | 624 |
| Pro | Val | Leu | Leu | Pro | Asp | Asn | His | Tyr | Leu | Ser | Thr | Gln | Ser | Ala | Leu | |
| | 195 | | | | | 200 | | | | | 205 | | | | | |
| agc | aaa | gac | ccc | aac | gag | aag | cgc | gat | cac | atg | gtc | ctg | ctg | gag | ttc | 672 |
| Ser | Lys | Asp | Pro | Asn | Glu | Lys | Arg | Asp | His | Met | Val | Leu | Leu | Glu | Phe | |
| 210 | | | | | 215 | | | | | 220 | | | | | | |
| gtg | acc | gcc | gcc | ggg | atc | act | ctc | ggc | atg | gac | gag | ctg | tac | aag | act | 720 |
| Val | Thr | Ala | Ala | Gly | Ile | Thr | Leu | Gly | Met | Asp | Glu | Leu | Tyr | Lys | Thr | |
| 225 | | | | | 230 | | | | | 235 | | | | | 240 | |
| agt | atg | gac | tac | aaa | gac | gat | gac | gac | aag | atg | cag | cct | tgg | cac | gga | 768 |
| Ser | Met | Asp | Tyr | Lys | Asp | Asp | Asp | Asp | Lys | Met | Gln | Pro | Trp | His | Gly | |
| | | | | 245 | | | | | 250 | | | | | 255 | | |
| aag | gcc | atg | cag | aga | gct | tcc | gag | gcc | gga | gcc | act | gcc | ccc | aag | gct | 816 |
| Lys | Ala | Met | Gln | Arg | Ala | Ser | Glu | Ala | Gly | Ala | Thr | Ala | Pro | Lys | Ala | |
| | | | 260 | | | | | 265 | | | | | 270 | | | |
| tcc | gca | cgg | aat | gcc | agg | ggc | gcc | ccg | atg | gat | ccc | aac | gag | tct | ccg | 864 |

```
                Ser Ala Arg Asn Ala Arg Gly Ala Pro Met Asp Pro Asn Glu Ser Pro
                            275                 280                 285 gct gcc ccc gag gcc gcc ctg cct aag gcg gga aag ttc ggc ccc gcc        912
Ala Ala Pro Glu Ala Ala Leu Pro Lys Ala Gly Lys Phe Gly Pro Ala
        290                 295                 300 agg aag tcg gga tcc cgg cag aaa aag agc gcc ccg gac acc cag gag        960
Arg Lys Ser Gly Ser Arg Gln Lys Lys Ser Ala Pro Asp Thr Gln Glu
305                 310                 315                 320 agg ccg ccc gtc cgc gca act ggg gcc cgc gcc aaa aag gcc cct cag       1008
Arg Pro Pro Val Arg Ala Thr Gly Ala Arg Ala Lys Lys Ala Pro Gln
                325                 330                 335 cgc gcc cag gac acg cag ccg tct gac gcc acc agc gcc cct ggg gca       1056
Arg Ala Gln Asp Thr Gln Pro Ser Asp Ala Thr Ser Ala Pro Gly Ala
        340                 345                 350 gag ggg ctg gag cct cct gcg gct cgg gag ccg gct ctt tcc agg gct       1104
Glu Gly Leu Glu Pro Pro Ala Ala Arg Glu Pro Ala Leu Ser Arg Ala
355                 360                 365 ggt tct tgc cgc cag agg ggc gcg cgc tgc tcc acg aag cca aga ccc       1152
Gly Ser Cys Arg Gln Arg Gly Ala Arg Cys Ser Thr Lys Pro Arg Pro
        370                 375                 380 ccg ccc ggg ccc tgg gac gtg ccc agc ccc ggc ctg ccg gtc tcg gcc       1200
Pro Pro Gly Pro Trp Asp Val Pro Ser Pro Gly Leu Pro Val Ser Ala
385                 390                 395                 400 ccc att ctc gta cgg agg gat gcg gcg cct ggg gcc tcg aag ctc cgg       1248
Pro Ile Leu Val Arg Arg Asp Ala Ala Pro Gly Ala Ser Lys Leu Arg
                405                 410                 415 gcg gtt ttg gag aag ttg aag ctc agc cgc gat gat atc tcc acg gcg       1296
Ala Val Leu Glu Lys Leu Lys Leu Ser Arg Asp Asp Ile Ser Thr Ala
        420                 425                 430 gcg ggg atg gtg aaa ggg gtt gtg gac cac ctg ctg ctc aga ctg aag       1344
Ala Gly Met Val Lys Gly Val Val Asp His Leu Leu Leu Arg Leu Lys
435                 440                 445 tgc gac tcc gcg ttc aga ggc gtc ggg ctg ctg aac acc ggg agc tac       1392
Cys Asp Ser Ala Phe Arg Gly Val Gly Leu Leu Asn Thr Gly Ser Tyr
        450                 455                 460 tat gag cac gtg aag att tct gca cct aat gca ttt gct gtc atg ttt       1440
Tyr Glu His Val Lys Ile Ser Ala Pro Asn Ala Phe Ala Val Met Phe
465                 470                 475                 480 aaa ctg gaa gtc ccc aga att caa cta gaa gaa tat tcc aac act cgt       1488
Lys Leu Glu Val Pro Arg Ile Gln Leu Glu Glu Tyr Ser Asn Thr Arg
                485                 490                 495 gca tat tac ttt gtg aaa ttt aaa aga aat ccg aaa gaa aat cat ctg       1536
Ala Tyr Tyr Phe Val Lys Phe Lys Arg Asn Pro Lys Glu Asn His Leu
        500                 505                 510 agt cag ttt tta gaa ggt gaa ata tta tca gct tct aag atg ctg tca       1584
Ser Gln Phe Leu Glu Gly Glu Ile Leu Ser Ala Ser Lys Met Leu Ser
515                 520                 525 aag ttt agg aaa atc att aag gaa gaa att aac gac att aaa gat aca       1632
Lys Phe Arg Lys Ile Ile Lys Glu Glu Ile Asn Asp Ile Lys Asp Thr
                530                 535                 540 gat gtc atc atg aag agg aaa aga gga ggg agc cct gct gta aca ctt       1680
Asp Val Ile Met Lys Arg Lys Arg Gly Gly Ser Pro Ala Val Thr Leu
545                 550                 555                 560 ctt att agt gaa aaa ata tct gtg gat ata acc ctg gct ttg gaa tca       1728
Leu Ile Ser Glu Lys Ile Ser Val Asp Ile Thr Leu Ala Leu Glu Ser
                565                 570                 575 aaa agt agc tgg cct gct agc acc caa gaa ggc ctg cgc att caa aac       1776
Lys Ser Ser Trp Pro Ala Ser Thr Gln Glu Gly Leu Arg Ile Gln Asn
        580                 585                 590
```

| | | | | | | | | | | | | | | | |
|---|---|---|---|---|---|---|---|---|---|---|---|---|---|---|---|
|tgg|ctt|tca|gca|aaa|gtt|agg|aag|caa|cta|cga|cta|aag|cca|ttt|tac|1824|
|Trp|Leu|Ser|Ala|Lys|Val|Arg|Lys|Gln|Leu|Arg|Leu|Lys|Pro|Phe|Tyr||
| | |595| | | |600| | | |605| | | | | |

```
tgg ctt tca gca aaa gtt agg aag caa cta cga cta aag cca ttt tac      1824
Trp Leu Ser Ala Lys Val Arg Lys Gln Leu Arg Leu Lys Pro Phe Tyr
        595                 600                 605 ctt gta ccc aag cat gca aag gaa gga aat ggt ttc caa gaa gaa aca      1872
Leu Val Pro Lys His Ala Lys Glu Gly Asn Gly Phe Gln Glu Glu Thr
    610                 615                 620 tgg cgg cta tcc ttc tct cac atc gaa aag gaa att ttg aac aat cat      1920
Trp Arg Leu Ser Phe Ser His Ile Glu Lys Glu Ile Leu Asn Asn His
625                 630                 635                 640 gga aaa tct aaa acg tgc tgt gaa aac aaa gaa gag aaa tgt tgc agg      1968
Gly Lys Ser Lys Thr Cys Cys Glu Asn Lys Glu Glu Lys Cys Cys Arg
                645                 650                 655 aaa gat tgt tta aaa cta atg aaa tac ctt tta gaa cag ctg aaa gaa      2016
Lys Asp Cys Leu Lys Leu Met Lys Tyr Leu Leu Glu Gln Leu Lys Glu
            660                 665                 670 agg ttt aaa gac aaa aaa cat ctg gat aaa ttc tct tct tat cat gtg      2064
Arg Phe Lys Asp Lys Lys His Leu Asp Lys Phe Ser Ser Tyr His Val
        675                 680                 685 aaa act gcc ttc ttt cac gta tgt acc cag aac cct caa gac agt cag      2112
Lys Thr Ala Phe Phe His Val Cys Thr Gln Asn Pro Gln Asp Ser Gln
690                 695                 700 tgg gac cgc aaa gac ctg ggc ctc tgc ttt gat aac tgc gtg aca tac      2160
Trp Asp Arg Lys Asp Leu Gly Leu Cys Phe Asp Asn Cys Val Thr Tyr
705                 710                 715                 720 ttt ctt cag tgc ctc agg aca gaa aaa ctt gag aat tat ttt att cct      2208
Phe Leu Gln Cys Leu Arg Thr Glu Lys Leu Glu Asn Tyr Phe Ile Pro
                725                 730                 735 gaa ttc aat cta ttc tct agc aac tta att gac aaa aga agt aaa gaa      2256
Glu Phe Asn Leu Phe Ser Ser Asn Leu Ile Asp Lys Arg Ser Lys Glu
            740                 745                 750 ttt ctg aca aag caa att gaa tat gaa aga aac aat gag ttt cca gtt      2304
Phe Leu Thr Lys Gln Ile Glu Tyr Glu Arg Asn Asn Glu Phe Pro Val
        755                 760                 765 ttt gat gaa ttt tga                                                   2319
Phe Asp Glu Phe
    770
```

<210> SEQ ID NO 4
<211> LENGTH: 772
<212> TYPE: PRT
<213> ORGANISM: Artificial Sequence
<220> FEATURE:
<223> OTHER INFORMATION: Synthetic Construct

<400> SEQUENCE: 4

```
Met Val Ser Lys Gly Glu Glu Leu Phe Thr Gly Val Val Pro Ile Leu
1               5                   10                  15

Val Glu Leu Asp Gly Asp Val Asn Gly His Lys Phe Ser Val Ser Gly
            20                  25                  30

Glu Gly Glu Gly Asp Ala Thr Tyr Gly Lys Leu Thr Leu Lys Phe Ile
        35                  40                  45

Cys Thr Thr Gly Lys Leu Pro Val Pro Trp Pro Thr Leu Val Thr Thr
    50                  55                  60

Leu Thr Tyr Gly Val Gln Cys Phe Ser Arg Tyr Pro Asp His Met Lys
65                  70                  75                  80

Gln His Asp Phe Phe Lys Ser Ala Met Pro Glu Gly Tyr Val Gln Glu
                85                  90                  95

Arg Thr Ile Phe Phe Lys Asp Asp Gly Asn Tyr Lys Thr Arg Ala Glu
            100                 105                 110
```

```
Val Lys Phe Glu Gly Asp Thr Leu Val Asn Arg Ile Glu Leu Lys Gly
            115                 120                 125

Ile Asp Phe Lys Glu Asp Gly Asn Ile Leu Gly His Lys Leu Glu Tyr
    130                 135                 140

Asn Tyr Asn Ser His Asn Val Tyr Ile Met Ala Asp Lys Gln Lys Asn
145                 150                 155                 160

Gly Ile Lys Val Asn Phe Lys Ile Arg His Asn Ile Glu Asp Gly Ser
                165                 170                 175

Val Gln Leu Ala Asp His Tyr Gln Gln Asn Thr Pro Ile Gly Asp Gly
            180                 185                 190

Pro Val Leu Leu Pro Asp Asn His Tyr Leu Ser Thr Gln Ser Ala Leu
        195                 200                 205

Ser Lys Asp Pro Asn Glu Lys Arg Asp His Met Val Leu Leu Glu Phe
210                 215                 220

Val Thr Ala Ala Gly Ile Thr Leu Gly Met Asp Glu Leu Tyr Lys Thr
225                 230                 235                 240

Ser Met Asp Tyr Lys Asp Asp Asp Lys Met Gln Pro Trp His Gly
                245                 250                 255

Lys Ala Met Gln Arg Ala Ser Glu Ala Gly Ala Thr Ala Pro Lys Ala
            260                 265                 270

Ser Ala Arg Asn Ala Arg Gly Ala Pro Met Asp Pro Asn Glu Ser Pro
        275                 280                 285

Ala Ala Pro Glu Ala Ala Leu Pro Lys Ala Gly Lys Phe Gly Pro Ala
    290                 295                 300

Arg Lys Ser Gly Ser Arg Gln Lys Lys Ser Ala Pro Asp Thr Gln Glu
305                 310                 315                 320

Arg Pro Pro Val Arg Ala Thr Gly Ala Arg Lys Lys Ala Pro Gln
                325                 330                 335

Arg Ala Gln Asp Thr Gln Pro Ser Asp Ala Thr Ser Ala Pro Gly Ala
            340                 345                 350

Glu Gly Leu Glu Pro Pro Ala Ala Arg Glu Pro Ala Leu Ser Arg Ala
        355                 360                 365

Gly Ser Cys Arg Gln Arg Gly Ala Arg Cys Ser Thr Lys Pro Arg Pro
370                 375                 380

Pro Pro Gly Pro Trp Asp Val Pro Ser Pro Gly Leu Pro Val Ser Ala
                385                 390                 395                 400

Pro Ile Leu Val Arg Arg Asp Ala Ala Pro Gly Ala Ser Lys Leu Arg
                405                 410                 415

Ala Val Leu Glu Lys Leu Lys Leu Ser Arg Asp Asp Ile Ser Thr Ala
            420                 425                 430

Ala Gly Met Val Lys Gly Val Val Asp His Leu Leu Leu Arg Leu Lys
        435                 440                 445

Cys Asp Ser Ala Phe Arg Gly Val Gly Leu Leu Asn Thr Gly Ser Tyr
450                 455                 460

Tyr Glu His Val Lys Ile Ser Ala Pro Asn Ala Phe Ala Val Met Phe
465                 470                 475                 480

Lys Leu Glu Val Pro Arg Ile Gln Leu Glu Glu Tyr Ser Asn Thr Arg
                485                 490                 495

Ala Tyr Tyr Phe Val Lys Phe Lys Arg Asn Pro Lys Glu Asn His Leu
            500                 505                 510

Ser Gln Phe Leu Glu Gly Glu Ile Leu Ser Ala Ser Lys Met Leu Ser
        515                 520                 525

Lys Phe Arg Lys Ile Ile Lys Glu Glu Ile Asn Asp Ile Lys Asp Thr
```

```
                        530                 535                 540
Asp Val Ile Met Lys Arg Lys Arg Gly Gly Ser Pro Ala Val Thr Leu
545                 550                 555                 560

Leu Ile Ser Glu Lys Ile Ser Val Asp Ile Thr Leu Ala Leu Glu Ser
                565                 570                 575

Lys Ser Ser Trp Pro Ala Ser Thr Gln Glu Gly Leu Arg Ile Gln Asn
            580                 585                 590

Trp Leu Ser Ala Lys Val Arg Lys Gln Leu Arg Leu Lys Pro Phe Tyr
                595                 600                 605

Leu Val Pro Lys His Ala Lys Glu Gly Asn Gly Phe Gln Glu Glu Thr
                610                 615                 620

Trp Arg Leu Ser Phe Ser His Ile Glu Lys Glu Ile Leu Asn Asn His
625                 630                 635                 640

Gly Lys Ser Lys Thr Cys Cys Glu Asn Lys Glu Lys Cys Cys Arg
                645                 650                 655

Lys Asp Cys Leu Lys Leu Met Lys Tyr Leu Leu Glu Gln Leu Lys Glu
                660                 665                 670

Arg Phe Lys Asp Lys Lys His Leu Asp Lys Phe Ser Ser Tyr His Val
                675                 680                 685

Lys Thr Ala Phe Phe His Val Cys Thr Gln Asn Pro Gln Asp Ser Gln
                690                 695                 700

Trp Asp Arg Lys Asp Leu Gly Leu Cys Phe Asp Asn Cys Val Thr Tyr
705                 710                 715                 720

Phe Leu Gln Cys Leu Arg Thr Glu Lys Leu Glu Asn Tyr Phe Ile Pro
                725                 730                 735

Glu Phe Asn Leu Phe Ser Ser Asn Leu Ile Asp Lys Arg Ser Lys Glu
                740                 745                 750

Phe Leu Thr Lys Gln Ile Glu Tyr Glu Arg Asn Asn Glu Phe Pro Val
                755                 760                 765

Phe Asp Glu Phe
    770

<210> SEQ ID NO 5
<211> LENGTH: 10
<212> TYPE: PRT
<213> ORGANISM: Artificial Sequence
<220> FEATURE:
<223> OTHER INFORMATION: NLS de SV40

<400> SEQUENCE: 5

Pro Lys Lys Lys Arg Lys Val Glu Asp Pro
1               5                   10

<210> SEQ ID NO 6
<211> LENGTH: 21
<212> TYPE: RNA
<213> ORGANISM: Artificial Sequence
<220> FEATURE:
<223> OTHER INFORMATION: siRNA targetting CHMP3

<400> SEQUENCE: 6
aaagcaugga cgaucaggaa g                                         21

<210> SEQ ID NO 7
<211> LENGTH: 19
<212> TYPE: RNA
<213> ORGANISM: Artificial Sequence
<220> FEATURE:
<223> OTHER INFORMATION: siRNA targetting LMNA
```

-continued

<400> SEQUENCE: 7
gguggugacg aucugggcu                                                      19

<210> SEQ ID NO 8
<211> LENGTH: 23
<212> TYPE: RNA
<213> ORGANISM: Artificial Sequence
<220> FEATURE:
<223> OTHER INFORMATION: siRNA targetting LMNA

<400> SEQUENCE: 8
aacuggacuu ccagaagaac auc                                                 23

<210> SEQ ID NO 9
<211> LENGTH: 12048
<212> TYPE: DNA
<213> ORGANISM: Artificial Sequence
<220> FEATURE:
<223> OTHER INFORMATION: Lentiviral vector pTRIP-CMV-EGFP-FLAG-cGAS
      E225A/D227A
<220> FEATURE:
<221> NAME/KEY: LTR
<222> LOCATION: (985)..(1618)
<220> FEATURE:
<221> NAME/KEY: PSI
<222> LOCATION: (1670)..(1807)
<220> FEATURE:
<221> NAME/KEY: RRE
<222> LOCATION: (2294)..(2498)
<220> FEATURE:
<221> NAME/KEY: promoter CMV
<222> LOCATION: (3203)..(3782)
<220> FEATURE:
<221> NAME/KEY: EGFP
<222> LOCATION: (3813)..(4529)
<220> FEATURE:
<221> NAME/KEY: FLAG
<222> LOCATION: (4536)..(4562)
<220> FEATURE:
<221> NAME/KEY: cGAS
<222> LOCATION: (4563)..(6128)
<220> FEATURE:
<221> NAME/KEY: E225A Mutation
<222> LOCATION: (5235)..(5237)
<220> FEATURE:
<221> NAME/KEY: D227A Mutation
<222> LOCATION: (5241)..(5243)
<220> FEATURE:
<221> NAME/KEY: Sin LTR
<222> LOCATION: (6319)..(6580)

<400> SEQUENCE: 9
acataattgg acaaactacc tacagagatt taaagctcta aggtaaatat aaaatttta         60 agtgtataat gtgttaaact actgattcta attgtttgtg tatttagat tccaacctat        120 ggaactgatg aatgggagca gtggtggaat gcctttaatg aggaaaacct gttttgctca       180
gaagaaatgc catctagtga tgatgaggct actgctgact ctcaacattc tactcctcca      240 aaaagaaga gaaggtaga agaccccaag gactttcctt cagaattgct aagttttttg        300
agtcatgctg tgtttagtaa tagaactctt gcttgctttg ctatttacac cacaaaggaa      360
aaagctgcac tgctatacaa gaaaattatg gaaaaatatt ctgtaacctt tataagtagg     420
cataacagtt ataatcataa catactgttt tttcttactc cacacaggca tagagtgtct     480
gctattaata actatgctca aaattgtgt acctttagct ttttaatttg taagggggtt       540
aataaggaat atttgatgta tagtgccttg actagagatc ataatcagcc ataccacatt     600
tgtagaggtt ttacttgctt taaaaaacct cccacacctc cccctgaacc tgaaacataa    660

```
aatgaatgca attgttgttg ttaacttgtt tattgcagct tataatggtt acaaataaag      720
caatagcatc acaaatttca caaataaagc attttttttca ctgcattcta gttgtggttt     780
gtccaaactc atcaatgtat cttatcatgt ctggatcaac tggataactc aagctaacca     840
aaatcatccc aaacttccca ccccatacccc tattaccact gccaattacc tgtggtttca    900
tttactctaa acctgtgatt cctctgaatt attttcattt taaagaaatt gtatttgtta     960
aatatgtact acaaacttag tagttggaag ggctaattca ctcccaaaga agacaagata    1020
tccttgatct gtggatctac cacacacaag gctacttccc tgattagcag aactacacac    1080
cagggccagg ggtcagatat ccactgacct ttggatggtg ctacaagcta gtaccagttg    1140
agccagataa ggtagaagag gccaataaag gagagaacac cagcttgtta caccctgtga    1200
gcctgcatgg gatggatgac ccggagagag aagtgttaga gtggaggttt gacagccgcc    1260
tagcatttca tcacgtggcc cgagagctgc atccggagta cttcaagaac tgctgatatc    1320
gagcttgcta caagggactt tccgctgggg acttttccagg gaggcgtggc ctgggcggga    1380
ctggggagtg gcgagccctc agatcctgca tataagcagc tgcttttttgc ctgtactggg    1440 tctctctggt tagaccagat ctgagcctgg gagctctctg gctaactagg gaacccactg    1500
cttaagcctc aataaagctt gccttgagtg cttcaagtag tgtgtgcccg tctgttgtgt    1560
gactctggta actagagatc cctcagaccc ttttagtcag tgtggaaaat ctctagcagt    1620
ggcgcccgaa cagggacttg aaagcgaaag ggaaaccaga ggagctctct cgacgcagga    1680
ctcggcttgc tgaagcgcgc acggcaagag gcgaggggcg gcgactggtg agtacgccaa    1740
aaattttgac tagcggaggc tagaaggaga gagatgggtg cgagagcgtc agtattaagc    1800
gggggagaat tagatcgcga tgggaaaaaa ttcggttaag gccaggggga agaaaaaat     1860 ataaattaaa acatatagta tgggcaagca gggagctaga acgattcgca gttaatcctg    1920
gcctgttaga aacatcagaa ggctgtagac aaatactggg acagctacaa ccatcccttc    1980
agacaggatc agaagaactt agatcattat ataatacagt agcaaccctc tattgtgtgc    2040
atcaaaggat agagataaaa gacaccaagg aagctttaga caagatagag gaagagcaaa    2100
acaaaagtaa gaccaccgca cagcaagcgg ccgctgatct tcagacctgg aggaggagat    2160
atgagggaca attggagaag tgaattatat aaatataaag tagtaaaaat tgaaccatta    2220
ggagtagcac ccaccaaggc aaagagaaga gtggtgcaga gagaaaaaag agcagtggga    2280
ataggagctt tgttccttgg gttcttggga gcagcaggaa gcactatggg cgcagcgtca    2340
atgacgctga cggtacaggc cagacaatta ttgtctggta tagtgcagca gcagaacaat    2400
ttgctgaggg ctattgaggc gcaacagcat ctgttgcaac tcacagtctg ggcatcaag    2460 cagctccagg caagaatcct ggctgtggaa agatacctaa aggatcaaca gctcctgggg    2520
atttggggtt gctctggaaa actcatttgc accactgctg tgccttggaa tgctagttgg    2580
agtaataaat ctctggaaca gatttggaat cacacgacct ggatggagtg gacagagaa    2640 attaacaatt acacaagctt aatacactcc ttaattgaag aatcgcaaaa ccagcaagaa    2700
aagaatgaac aagaattatt ggaattagat aaatgggcaa gtttgtggaa ttggtttaac    2760
ataacaaatt ggctgtggta tataaaatta ttcataatga tagtaggagg cttggtaggt    2820
ttaagaatag ttttttgctgt actttctata gtgaatagag ttaggcaggg atattcacca    2880
ttatcgtttc agacccacct cccaaccccg aggggacccg acaggcccga aggaatagaa    2940
gaagaaggtg gagagagaga cagagacaga tccattcgat tagtgaacgg atctcgacgg    3000
```

```
tatcgccgaa ttcacaaatg gcagtattca tccacaattt taaaagaaaa ggggggattg    3060
gggggtacag tgcagggaa agaatagtag acataatagc aacagacata caaactaaag    3120
aattacaaaa acaaattaca aaattcaaa attttcgggt ttattacagg gacagcagag    3180
atccactttg gctgatacgc gtatagtaat caattacggg gtcattagtt catagcccat    3240
atatggagtt ccgcgttaca taacttacgg taaatggccc gcctggctga ccgcccaacg    3300 accccgccc attgacgtca ataatgacgt atgttcccat agtaacgcca tagggactt    3360 tccattgacg tcaatgggtg gagtatttac ggtaaactgc ccacttggca gtacatcaag    3420
tgtatcatat gccaagtacg ccccctattg acgtcaatga cggtaaatgg cccgcctggc    3480
attatgccca gtacatgacc ttatgggact ttcctacttg gcagtacatc tacgtattag    3540
tcatcgctat taccatggtg atgcggtttt ggcagtacat caatgggcgt ggatagcggt    3600
ttgactcacg gggatttcca agtctccacc ccattgacgt caatgggagt ttgttttggc    3660
accaaaatca acgggacttt ccaaaatgtc gtaacaactc cgccccattg acgcaaatgg    3720
gcggtaggcg tgtacggtgg gaggtctata taagcagagc tggtttagtg aaccgtcaga    3780
tcccgcgggc tagcggatct gtcgacgcca ccatggtgag caagggcgag gagctgttca    3840
ccggggtggt gcccatcctg gtcgagctgg acggcgacgt aaacgccac aagttcagcg    3900 tgtccggcga gggcgaggc gatgccacct acggcaagct gaccctgaag ttcatctgca    3960
ccaccggcaa gctgcccgtg ccctggccca ccctcgtgac caccctgacc tacggcgtgc    4020
agtgcttcag ccgctacccc gaccacatga gcagcacga cttcttcaag tccgccatgc    4080
ccgaaggcta cgtccaggag cgcaccatct tcttcaagga cgacggcaac tacaagaccc    4140
gcgccgaggt gaagttcgag ggcgacaccc tggtgaaccg catcgagctg aagggcatcg    4200
acttcaagga ggacggcaac atcctggggc acaagctgga gtacaactac aacagccaca    4260
acgtctatat catggccgac aagcagaaga acggcatcaa ggtgaacttc aagatccgcc    4320
acaacatcga ggacggcagc gtgcagctcg ccgaccacta ccagcagaac ccccccatcg    4380
gcgacggccc cgtgctgctg cccgacaacc actacctgag cacccagtcc gccctgagca    4440
aagaccccaa cgagaagcgc gatcacatgg tcctgctgga gttcgtgacc gccgccggga    4500
tcactctcgg catggacgag ctgtacaaga ctagtatgga ctacaaagac gatgacgaca    4560
agatgcagcc ttggcacgga aaggccatgc agagagcttc cgaggccgga gccactgccc    4620
ccaaggcttc cgcacggaat gccaggggcg ccccgatgga tcccaacgag tctccggctg    4680
cccccgagcc cgccctgcct aaggcgggaa agttcggccc cgccaggaag tcgggatccc    4740
ggcagaaaaa gagcgccccg gacacccagg agaggccgcc cgtccgcgca actggggccc    4800
gcgccaaaaa ggcccctcag cgcgcccagg acacgcagcc gtctgacgcc accagcgccc    4860 ctgggcaga ggggctggag cctcctgcgg ctcgggagcc ggctctttcc agggctggtt    4920
cttgccgcca gaggggcgcg cgctgctcca cgaagccaag accccgccc gggccctggg    4980 acgtgcccag ccccggcctg ccggtctcgg cccccattct cgtacggagg gatgcggcgc    5040
ctggggcctc gaagctccgg gcggttttgg agaagttgaa gctcagccgc gatgatatct    5100
ccacggcggc ggggatggtg aaaggggttg tggaccacct gctgctcaga ctgaagtgcg    5160
actccgcgtt cagaggcgtc gggctgctga acaccgggag ctactatgag cacgtgaaga    5220
tttctgcacc taatgcattt gctgtcatgt ttaaactgga agtccccaga attcaactag    5280
aagaatattc caacactcgt gcatattact ttgtgaaatt taaagaaat ccgaaagaaa    5340 atcatctgag tcagttttta gaaggtgaaa tattatcagc ttctaagatg ctgtcaaagt    5400
```

```
ttaggaaaat cattaaggaa gaaattaacg acattaaaga tacagatgtc atcatgaaga    5460
ggaaaagagg agggagccct gctgtaacac ttcttattag tgaaaaaata tctgtggata    5520
taaccctggc tttggaatca aaaagtagct ggcctgctag cacccaagaa ggcctgcgca    5580
ttcaaaactg gctttcagca aaagttagga agcaactacg actaaagcca ttttaccttg    5640
tacccaagca tgcaaaggaa ggaaatggtt tccaagaaga acatggcgg ctatccttct     5700
ctcacatcga aaggaaatt tgaacaatc atggaaaatc taaaacgtgc tgtgaaaaca      5760
aagaagagaa atgttgcagg aaagattgtt taaaactaat gaaataccct ttagaacagc    5820
tgaaagaaag gtttaaagac aaaaaacatc tggataaatt ctcttcttat catgtgaaaa    5880
ctgccttctt tcacgtatgt acccagaacc ctcaagacag tcagtgggac cgcaaagacc    5940
tgggcctctg ctttgataac tgcgtgacat actttcttca gtgcctcagg acagaaaaac    6000
ttgagaatta ttttattcct gaattcaatc tattctctag caacttaatt gacaaaagaa    6060
gtaaagaatt tctgacaaag caaattgaat atgaaagaaa caatgagttt ccagttttg     6120
atgaattttg actcgagacc tagaaaaaca tggagcaatc acaagtagca atacagcagc    6180
taccaatgct gattgtgcct ggctagaagc acaagaggag gaggaggtgg gttttccagt    6240
cacacctcag gtacctttaa gaccaatgac ttacaaggca gctgtagatc ttagccactt    6300
tttaaaagaa aaggggggac tggaagggct aattcactcc caacgaagac aaaatcgtcg    6360
agagatgctg catataagca gctgcttttt gcttgtactg ggtctctctg gttagaccag    6420
atctgagcct gggagctctc tggctaacta gggaacccac tgcttaagcc tcaataaagc    6480
ttgccttgag tgcttcaagt agtgtgtgcc cgtctgttgt gtgactctgg taactagaga    6540
tccctcagac ccttttagtc agtgtggaaa atctctagca gtagtagttc atgtcatctt    6600
attattcagt atttataact tgcaaagaaa tgaatatcag agagtgagag gccttgacat    6660
tataatagat ttagcaggaa ttgaactagg agtggagcac acaggcaaag ctgcagaagt    6720
acttggaaga agccaccaga gatactcacg attctgcaca tacctggcta atcccagatc    6780
ctaaggatta cattaagttt actaacattt atataatgat ttatagttta aagtataaac    6840
ttatctaatt tactattctg acagatatta attaatcctc aaatatcata agagatgatt    6900
actattatcc ccatttaaca caagaggaaa ctgagaggga aagatgttga agtaattttc    6960
ccacaattac agcatccgtt agttacgact ctatgatctt ctgacacaaa ttccatttac    7020
tcctcaccct atgactcagt cgaatatatc aaagttatgg acattatgct aagtaacaaa    7080
ttacccttt atatagtaaa tactgagtag attgagagaa gaaattgttt gcaaacctga    7140
atagcttcaa gaagaagaga agtgaggata agaataacag ttgtcattta acaagtttta    7200
acaagtaact tggttagaaa gggattcaaa tgcataaagc aagggataaa tttttctggc    7260
aacaagacta tacaatataa ccttaaatat gacttcaaat aattgttgga acttgataaa    7320
actaattaaa tattattgaa gattatcaat attataaatg taatttactt ttaaaaaggg    7380
aacatagaaa tgtgtatcat tagagtagaa aacaatcctt attatcacaa tttgtcaaaa    7440
caagtttgtt attaacacaa gtagaatact gcattcaatt aagttgactg cagattttgt    7500
gttttgttaa aattagaaag agataacaac aatttgaatt attgaaagta acatgtaaat    7560
agttctacat acgttctttt gacatcttgt tcaatcattg atcgaagttc tttatcttgg    7620
aagaatttgt tccaaagact ctgaaataag gaaaacaatc tattatatag tctcacacct    7680
ttgttttact tttagtgatt tcaatttaat aatgtaaatg gttaaaattt attcttctct    7740
```

```
gagatcattt cacattgcag atagaaaacc tgagactggg gtaattttta ttaaaatcta      7800
atttaatctc agaaacacat ctttattcta acatcaattt ttccagtttg atattatcat      7860
ataaagtcag ccttcctcat ctgcaggttc cacaacaaaa atccaaccaa ctgtggatca      7920
aaaatattgg gaaaaaatta aaaatagcaa tacaacaata aaaaaataca aatcagaaaa      7980
acagcacagt ataacaactt tatttagcat ttacaatcta ttaggtatta taagtaatct      8040
agccagatcc tctacgccgg acgcatcgtg gccggcatca ccggcgccac aggtgcggtt      8100
gctggcgcct atatcgccga catcaccgat ggggaagatc gggctcgcca cttcgggctc      8160
atgagcgctt gtttcggcgt gggtatggtg gcaggcccg tggccggggg actgttgggc       8220
gccatctcct tgcatgcacc attccttgcg gcggcggtgc tcaacggcct caacctacta      8280
ctgggctgct tcctaatgca ggagtcgcat aagggagagc gtcgaatggt gcactctcag      8340
tacaatctgc tctgatgccg catagttaag ccagccccga cacccgccaa cacccgctga      8400
cgcgccctga cgggcttgtc tgctcccggc atccgcttac agacaagctg tgaccgtctc      8460
cgggagctgc atgtgtcaga ggttttcacc gtcatcaccg aaacgcgcga dacgaaaggg      8520
cctcgtgata cgcctatttt tataggttaa tgtcatgata ataatggttt cttagacgtc      8580
aggtggcact tttcggggaa atgtgcgcgg aaccccctatt tgtttatttt tctaaataca     8640
ttcaaatatg tatccgctca tgagacaata accctgataa atgcttcaat aatattgaaa      8700
aaggaagagt atgagtattc aacatttccg tgtcgccctt attcccttt ttgcggcatt       8760 ttgccttcct gttttgctc acccagaaac gctggtgaaa gtaaaagatg ctgaagatca       8820
gttgggtgca cgagtgggtt acatcgaact ggatctcaac agcggtaaga tccttgagag      8880
ttttcgcccc gaagaacgtt ttccaatgat gagcactttt aaagttctgc tatgtggcgc      8940
ggtattatcc cgtattgacg ccgggcaaga gcaactcggt cgccgcatac actattctca      9000
gaatgacttg gttgagtact caccagtcac agaaaagcat cttacggatg gcatgacagt      9060
aagagaatta tgcagtgctg ccataaccat gagtgataac actgcggcca acttacttct      9120
gacaacgatc ggaggaccga aggagctaac cgcttttttg cacaacatgg ggatcatgt       9180 aactcgcctt gatcgttggg aaccggagct gaatgaagcc ataccaaacg acgagcgtga     9240
caccacgatg cctgtagcaa tggcaacaac gttgcgcaaa ctattaactg gcgaactact     9300
tactctagct tcccggcaac aattaataga ctggatggag gcggataaag ttgcaggacc      9360
acttctgcgc tcggcccttc cggctggctg gtttattgct gataaatctg gagccggtga     9420
gcgtgggtct cgcggtatca ttgcagcact ggggccagat ggtaagccct cccgtatcgt      9480
agttatctac acgacgggga gtcaggcaac tatggatgaa cgaaatagac agatcgctga     9540
gataggtgcc tcactgatta agcattggta actgtcagac caagtttact catatatact      9600
ttagattgat ttaaaacttc attttaatt taaaaggatc taggtgaaga tccttttga       9660 taatctcatg accaaaatcc cttaacgtga gttttcgttc cactgagcgt cagaccccgt      9720
agaaaagatc aaaggatctt cttgagatcc ttttttctg cgcgtaatct gctgcttgca      9780
aacaaaaaaa ccaccgctac cagcggtggt ttgtttgccg gatcaagagc taccaactct      9840
ttttccgaag gtaactggct tcagcagagc gcagatacca aatactgttc ttctagtgta     9900
gccgtagtta ggccaccact tcaagaactc tgtagcaccg cctacatacc tcgctctgct     9960
aatcctgtta ccagtggctg ctgccagtgg cgataagtcg tgtcttaccg ggttggactc    10020
aagacgatag ttaccggata aggcgcagcg gtcgggctga acggggggtt cgtgcacaca    10080
gcccagcttg gagcgaacga cctacaccga actgagatac ctacagcgtg agctatgaga    10140
```

```
aagcgccacg cttcccgaag ggagaaaggc ggacaggtat ccggtaagcg gcagggtcgg    10200
aacaggagag cgcacgaggg agcttccagg gggaaacgcc tggtatcttt atagtcctgt    10260
cgggtttcgc cacctctgac ttgagcgtcg attttttgtga tgctcgtcag ggggcggag    10320 cctatggaaa aacgccagca acgcggcctt tttacggttc ctggccttt gctggccttt    10380 tgctcacatg ttctttcctg cgttatcccc tgattctgtg gataaccgta ttaccgcctt    10440
tgagtgagct gataccgctc gccgcagccg aacgaccgag cgcagcgagt cagtgagcga    10500
ggaagcggaa gagcgcccaa tacgcaaacc gcctctcccc gcgcgttggc cgattcatta    10560
atgcagctgt ggaatgtgtg tcagttaggg tgtggaaagt ccccaggctc cccagcaggc    10620
agaagtatgc aaagcatgca tctcaattag tcagcaacca ggtgtggaaa gtccccaggc    10680
tccccagcag gcagaagtat gcaaagcatg catctcaatt agtcagcaac catagtcccg    10740
cccctaactc cgcccatccc gcccctaact ccgcccagtt ccgcccattc tccgcccat    10800 ggctgactaa ttttttttat ttatgcagag gccgaggccg cctcggcctc tgagctattc    10860
cagaagtagt gaggaggctt ttttggaggc ctaggctttt gcaaaaagct tggacacaag    10920
acaggcttgc gagatatgtt tgagaatacc actttatccc gcgtcaggga gaggcagtgc    10980
gtaaaaagac gcggactcat gtgaaatact ggttttagt gcgccagatc tctataatct    11040
cgcgcaacct attttcccct cgaacacttt ttaagccgta gataaacagg ctgggacact    11100
tcacatgagc gaaaaataca tcgtcacctg ggacatgttg cagatccatg cacgtaaact    11160
cgcaagccga ctgatgcctt ctgaacaatg gaaaggcatt attgccgtaa gccgtggcgg    11220
tctgtaccgg gtgcgttact ggcgcgtgaa ctgggtattc gtcatgtcga taccgtttgt    11280
atttccagct acgatcacga caaccagcgc gagcttaaag tgctgaaacg cgcagaaggc    11340
gatggcgaag gcttcatcgt tattgatgac ctggtggata ccggtggtac tgcggttgcg    11400
attcgtgaaa tgtatccaaa agcgcacttt gtcaccatct tcgcaaaacc ggctggtcgt    11460
ccgctggttg atgactatgt tgttgatatc ccgcaagata cctggattga acagccgtgg    11520
gatatgggcg tcgtattcgt cccgccaatc tccggtcgct aatcttttca acgcctggca    11580
ctgccgggcg ttgttctttt taacttcagg cgggttacaa tagtttccag taagtattct    11640
ggaggctgca tccatgacac aggcaaacct gagcgaaacc ctgttcaaac ccgctttaa    11700 acatcctgaa acctcgacgc tagtccgccg ctttaatcac ggcgcacaac cgcctgtgca    11760
gtcggccctt gatggtaaaa ccatccctca ctggtatcgc atgattaacc gtctgatgtg    11820
gatctggcgc ggcattgacc cacgcgaaat cctcgacgtc caggcacgta ttgtgatgag    11880
cgatgccgaa cgtaccgacg atgatttata cgatacggtg attggctacc gtggcggcaa    11940
ctggatttat gagtgggccc cggatctttg tgaaggaacc ttacttctgt ggtgtgacat    12000
aattggacaa actacctaca gagatttaaa gctctaaggt aatataaa                 12048
```

<210> SEQ ID NO 10
<211> LENGTH: 1755
<212> TYPE: DNA
<213> ORGANISM: Artificial Sequence
<220> FEATURE:
<223> OTHER INFORMATION: human gene AIM2 mutated to generate F27G
      mutation and fused with EGFP
<220> FEATURE:
<221> NAME/KEY: CDS
<222> LOCATION: (1)..(1755)
<220> FEATURE:
<221> NAME/KEY: AIM2
<222> LOCATION: (1)..(1129)

```
<220> FEATURE:
<221> NAME/KEY: Muation F27G
<222> LOCATION: (79)..(81)
<220> FEATURE:
<221> NAME/KEY: EGFP
<222> LOCATION: (1136)..(1755)

<400> SEQUENCE: 10 atg gag agt aaa tac aag gag ata ctc ttg cta aca ggc ctg gat aac      48
Met Glu Ser Lys Tyr Lys Glu Ile Leu Leu Leu Thr Gly Leu Asp Asn
1               5                   10                  15 atc act gat gag gaa ctg gat agg ttt aag ggc ttt ctt tca gac gag      96
Ile Thr Asp Glu Glu Leu Asp Arg Phe Lys Gly Phe Leu Ser Asp Glu
            20                  25                  30 ttt aat att gcc aca ggc aaa cta cat act gca aac aga ata caa gta     144
Phe Asn Ile Ala Thr Gly Lys Leu His Thr Ala Asn Arg Ile Gln Val
        35                  40                  45 gct acc ttg atg att caa aat gct ggg gcg gtg tct gca gtg atg aag     192
Ala Thr Leu Met Ile Gln Asn Ala Gly Ala Val Ser Ala Val Met Lys
    50                  55                  60 acc att cgt att ttt cag aag ttg aat tat atg ctt ttg gca aaa cgt     240
Thr Ile Arg Ile Phe Gln Lys Leu Asn Tyr Met Leu Leu Ala Lys Arg
65                  70                  75                  80 ctt cag gag gag aag gag aaa gtt gat aag caa tac aaa tcg gta aca     288
Leu Gln Glu Glu Lys Glu Lys Val Asp Lys Gln Tyr Lys Ser Val Thr
                85                  90                  95 aaa cca aag cca cta agt caa gct gaa atg agt cct gct gca tct gca     336
Lys Pro Lys Pro Leu Ser Gln Ala Glu Met Ser Pro Ala Ala Ser Ala
            100                 105                 110 gcc atc aga aat gat gtc gca aag caa cgt gct gca cca aaa gtc tct     384
Ala Ile Arg Asn Asp Val Ala Lys Gln Arg Ala Ala Pro Lys Val Ser
        115                 120                 125 cct cat gtt aag cct gaa cag aaa cag atg gtg gcc cag cag gaa tct     432
Pro His Val Lys Pro Glu Gln Lys Gln Met Val Ala Gln Gln Glu Ser
    130                 135                 140 atc aga gaa ggg ttt cag aag cgc tgt ttg cca gtt atg gta ctg aaa     480
Ile Arg Glu Gly Phe Gln Lys Arg Cys Leu Pro Val Met Val Leu Lys
145                 150                 155                 160 gca aag aag ccc ttc acg ttt gag acc caa gaa ggc aag cag gag atg     528
Ala Lys Lys Pro Phe Thr Phe Glu Thr Gln Glu Gly Lys Gln Glu Met
                165                 170                 175 ttt cat gct aca gtg gct aca gaa aag gaa ttc ttc ttt gta aaa gtt     576
Phe His Ala Thr Val Ala Thr Glu Lys Glu Phe Phe Phe Val Lys Val
            180                 185                 190 ttt aat aca ctg ctg aaa gat aaa ttc att cca aag aga ata att ata     624
Phe Asn Thr Leu Leu Lys Asp Lys Phe Ile Pro Lys Arg Ile Ile Ile
        195                 200                 205 ata gca aga tat tat cgg cac agt ggt ttc tta gag gta aat agc gcc     672
Ile Ala Arg Tyr Tyr Arg His Ser Gly Phe Leu Glu Val Asn Ser Ala
    210                 215                 220 tca cgt gtg tta gat gct gaa tct gac caa aag gtt aat gtc ccg ctg     720
Ser Arg Val Leu Asp Ala Glu Ser Asp Gln Lys Val Asn Val Pro Leu
225                 230                 235                 240 aac att atc aga aaa gct ggt gaa acc ccg aag atc aac acg ctt caa     768
Asn Ile Ile Arg Lys Ala Gly Glu Thr Pro Lys Ile Asn Thr Leu Gln
                245                 250                 255 act cag ccc ctt gga aca att gtg aat ggt ttg ttt gta gtc cag aag     816
Thr Gln Pro Leu Gly Thr Ile Val Asn Gly Leu Phe Val Val Gln Lys
            260                 265                 270 gta aca gaa aag aag aaa aac ata tta ttt gac cta agt gac aac act     864
Val Thr Glu Lys Lys Lys Asn Ile Leu Phe Asp Leu Ser Asp Asn Thr
```

-continued

|   |   |   |   |   |   |   |   |   |   |   |   |   |   |   |   |
|---|---|---|---|---|---|---|---|---|---|---|---|---|---|---|---|
| | | 275 | | | | 280 | | | | | 285 | | | | |
| ggg | aaa | atg | gaa | gta | ctg | ggg | gtt | aga | aac | gag | gac | aca | atg | aaa | tgt | 912
| Gly | Lys | Met | Glu | Val | Leu | Gly | Val | Arg | Asn | Glu | Asp | Thr | Met | Lys | Cys |
| | 290 | | | | 295 | | | | | 300 | | | | | |

| aag | gaa | gga | gat | aag | gtt | cga | ctt | aca | ttc | ttc | aca | ctg | tca | aaa | aat | 960
| Lys | Glu | Gly | Asp | Lys | Val | Arg | Leu | Thr | Phe | Phe | Thr | Leu | Ser | Lys | Asn |
| 305 | | | | | 310 | | | | | 315 | | | | | 320 |

| gga | gaa | aaa | cta | cag | ctg | aca | tct | gga | gtt | cat | agc | acc | ata | aag | gtt | 1008
| Gly | Glu | Lys | Leu | Gln | Leu | Thr | Ser | Gly | Val | His | Ser | Thr | Ile | Lys | Val |
| | | | | 325 | | | | | 330 | | | | | 335 | |

| att | aag | gcc | aaa | aaa | aaa | aca | act | agt | atg | gtg | agc | aag | ggc | gag | gag | 1056
| Ile | Lys | Ala | Lys | Lys | Lys | Thr | Thr | Ser | Met | Val | Ser | Lys | Gly | Glu | Glu |
| | | | 340 | | | | | 345 | | | | | 350 | | |

| ctg | ttc | acc | ggg | gtg | gtg | ccc | atc | ctg | gtc | gag | ctg | gac | ggc | gac | gta | 1104
| Leu | Phe | Thr | Gly | Val | Val | Pro | Ile | Leu | Val | Glu | Leu | Asp | Gly | Asp | Val |
| | | | 355 | | | | | 360 | | | | | 365 | | |

| aac | ggc | cac | aag | ttc | agc | gtg | tcc | ggc | gag | ggc | gag | ggc | gat | gcc | acc | 1152
| Asn | Gly | His | Lys | Phe | Ser | Val | Ser | Gly | Glu | Gly | Glu | Gly | Asp | Ala | Thr |
| | 370 | | | | 375 | | | | | 380 | | | | | |

| tac | ggc | aag | ctg | acc | ctg | aag | ttc | atc | tgc | acc | acc | ggc | aag | ctg | ccc | 1200
| Tyr | Gly | Lys | Leu | Thr | Leu | Lys | Phe | Ile | Cys | Thr | Thr | Gly | Lys | Leu | Pro |
| 385 | | | | | 390 | | | | | 395 | | | | | 400 |

| gtg | ccc | tgg | ccc | acc | ctc | gtg | acc | acc | ctg | acc | tac | ggc | gtg | cag | tgc | 1248
| Val | Pro | Trp | Pro | Thr | Leu | Val | Thr | Thr | Leu | Thr | Tyr | Gly | Val | Gln | Cys |
| | | | | 405 | | | | | 410 | | | | | 415 | |

| ttc | agc | cgc | tac | ccc | gac | cac | atg | aag | cag | cac | gac | ttc | ttc | aag | tcc | 1296
| Phe | Ser | Arg | Tyr | Pro | Asp | His | Met | Lys | Gln | His | Asp | Phe | Phe | Lys | Ser |
| | | | 420 | | | | | 425 | | | | | 430 | | |

| gcc | atg | ccc | gaa | ggc | tac | gtc | cag | gag | cgc | acc | atc | ttc | ttc | aag | gac | 1344
| Ala | Met | Pro | Glu | Gly | Tyr | Val | Gln | Glu | Arg | Thr | Ile | Phe | Phe | Lys | Asp |
| | | 435 | | | | | 440 | | | | | 445 | | | |

| gac | ggc | aac | tac | aag | acc | cgc | gcc | gag | gtg | aag | ttc | gag | ggc | gac | acc | 1392
| Asp | Gly | Asn | Tyr | Lys | Thr | Arg | Ala | Glu | Val | Lys | Phe | Glu | Gly | Asp | Thr |
| | 450 | | | | | 455 | | | | | 460 | | | | |

| ctg | gtg | aac | cgc | atc | gag | ctg | aag | ggc | atc | gac | ttc | aag | gag | gac | ggc | 1440
| Leu | Val | Asn | Arg | Ile | Glu | Leu | Lys | Gly | Ile | Asp | Phe | Lys | Glu | Asp | Gly |
| 465 | | | | | 470 | | | | | 475 | | | | | 480 |

| aac | atc | ctg | ggg | cac | aag | ctg | gag | tac | aac | tac | aac | agc | cac | aac | gtc | 1488
| Asn | Ile | Leu | Gly | His | Lys | Leu | Glu | Tyr | Asn | Tyr | Asn | Ser | His | Asn | Val |
| | | | | 485 | | | | | 490 | | | | | 495 | |

| tat | atc | atg | gcc | gac | aag | cag | aag | aac | ggc | atc | aag | gtg | aac | ttc | aag | 1536
| Tyr | Ile | Met | Ala | Asp | Lys | Gln | Lys | Asn | Gly | Ile | Lys | Val | Asn | Phe | Lys |
| | | | 500 | | | | | 505 | | | | | 510 | | |

| atc | cgc | cac | aac | atc | gag | gac | ggc | agc | gtg | cag | ctc | gcc | gac | cac | tac | 1584
| Ile | Arg | His | Asn | Ile | Glu | Asp | Gly | Ser | Val | Gln | Leu | Ala | Asp | His | Tyr |
| | | 515 | | | | | 520 | | | | | 525 | | | |

| cag | cag | aac | acc | ccc | atc | ggc | gac | ggc | ccc | gtg | ctg | ctg | ccc | gac | aac | 1632
| Gln | Gln | Asn | Thr | Pro | Ile | Gly | Asp | Gly | Pro | Val | Leu | Leu | Pro | Asp | Asn |
| | 530 | | | | | 535 | | | | | 540 | | | | |

| cac | tac | ctg | agc | acc | cag | tcc | gcc | ctg | agc | aaa | gac | ccc | aac | gag | aag | 1680
| His | Tyr | Leu | Ser | Thr | Gln | Ser | Ala | Leu | Ser | Lys | Asp | Pro | Asn | Glu | Lys |
| 545 | | | | | 550 | | | | | 555 | | | | | 560 |

| cgc | gat | cac | atg | gtc | ctg | ctg | gag | ttc | gtg | acc | gcc | gcc | ggg | atc | act | 1728
| Arg | Asp | His | Met | Val | Leu | Leu | Glu | Phe | Val | Thr | Ala | Ala | Gly | Ile | Thr |
| | | | | 565 | | | | | 570 | | | | | 575 | |

| ctc | ggc | atg | gac | gag | ctg | tac | aag | taa | | | | | | | | 1755
| Leu | Gly | Met | Asp | Glu | Leu | Tyr | Lys | | | | | | | | |
| | | | 580 | | | | | | | | | | | | |

<210> SEQ ID NO 11
<211> LENGTH: 584
<212> TYPE: PRT
<213> ORGANISM: Artificial Sequence
<220> FEATURE:
<223> OTHER INFORMATION: Synthetic Construct

<400> SEQUENCE: 11

```
Met Glu Ser Lys Tyr Lys Glu Ile Leu Leu Leu Thr Gly Leu Asp Asn
1               5                   10                  15

Ile Thr Asp Glu Glu Leu Asp Arg Phe Lys Gly Phe Leu Ser Asp Glu
                20                  25                  30

Phe Asn Ile Ala Thr Gly Lys Leu His Thr Ala Asn Arg Ile Gln Val
            35                  40                  45

Ala Thr Leu Met Ile Gln Asn Ala Gly Ala Val Ser Ala Val Met Lys
        50                  55                  60

Thr Ile Arg Ile Phe Gln Lys Leu Asn Tyr Met Leu Leu Ala Lys Arg
65                  70                  75                  80

Leu Gln Glu Glu Lys Lys Val Asp Lys Gln Tyr Lys Ser Val Thr
                85                  90                  95

Lys Pro Lys Pro Leu Ser Gln Ala Glu Met Ser Pro Ala Ala Ser Ala
                100                 105                 110

Ala Ile Arg Asn Asp Val Ala Lys Gln Arg Ala Ala Pro Lys Val Ser
            115                 120                 125

Pro His Val Lys Pro Glu Gln Lys Gln Met Val Ala Gln Gln Glu Ser
        130                 135                 140

Ile Arg Glu Gly Phe Gln Lys Arg Cys Leu Pro Val Met Val Leu Lys
145                 150                 155                 160

Ala Lys Lys Pro Phe Thr Phe Glu Thr Gln Glu Gly Lys Gln Glu Met
                165                 170                 175

Phe His Ala Thr Val Ala Thr Glu Lys Glu Phe Phe Val Lys Val
            180                 185                 190

Phe Asn Thr Leu Leu Lys Asp Lys Phe Ile Pro Lys Arg Ile Ile Ile
        195                 200                 205

Ile Ala Arg Tyr Tyr Arg His Ser Gly Phe Leu Glu Val Asn Ser Ala
    210                 215                 220

Ser Arg Val Leu Asp Ala Glu Ser Asp Gln Lys Val Asn Val Pro Leu
225                 230                 235                 240

Asn Ile Ile Arg Lys Ala Gly Glu Thr Pro Lys Ile Asn Thr Leu Gln
                245                 250                 255

Thr Gln Pro Leu Gly Thr Ile Val Asn Gly Leu Phe Val Gln Lys
                260                 265                 270

Val Thr Glu Lys Lys Lys Asn Ile Leu Phe Asp Leu Ser Asp Asn Thr
                275                 280                 285

Gly Lys Met Glu Val Leu Gly Val Arg Asn Glu Asp Thr Met Lys Cys
        290                 295                 300

Lys Glu Gly Asp Lys Val Arg Leu Thr Phe Phe Thr Leu Ser Lys Asn
305                 310                 315                 320

Gly Glu Lys Leu Gln Leu Thr Ser Gly Val His Ser Thr Ile Lys Val
                325                 330                 335

Ile Lys Ala Lys Lys Thr Thr Ser Met Val Ser Lys Gly Glu Glu
            340                 345                 350

Leu Phe Thr Gly Val Val Pro Ile Leu Val Glu Leu Asp Gly Asp Val
        355                 360                 365

Asn Gly His Lys Phe Ser Val Ser Gly Glu Gly Glu Gly Asp Ala Thr
```

370                 375                 380
Tyr Gly Lys Leu Thr Leu Lys Phe Ile Cys Thr Thr Gly Lys Leu Pro
385                 390                 395                 400

Val Pro Trp Pro Thr Leu Val Thr Thr Leu Thr Tyr Gly Val Gln Cys
                405                 410                 415

Phe Ser Arg Tyr Pro Asp His Met Lys Gln His Asp Phe Phe Lys Ser
            420                 425                 430

Ala Met Pro Glu Gly Tyr Val Gln Glu Arg Thr Ile Phe Phe Lys Asp
        435                 440                 445

Asp Gly Asn Tyr Lys Thr Arg Ala Glu Val Lys Phe Glu Gly Asp Thr
    450                 455                 460

Leu Val Asn Arg Ile Glu Leu Lys Gly Ile Asp Phe Lys Glu Asp Gly
465                 470                 475                 480

Asn Ile Leu Gly His Lys Leu Glu Tyr Asn Tyr Asn Ser His Asn Val
                485                 490                 495

Tyr Ile Met Ala Asp Lys Gln Lys Asn Gly Ile Lys Val Asn Phe Lys
            500                 505                 510

Ile Arg His Asn Ile Glu Asp Gly Ser Val Gln Leu Ala Asp His Tyr
        515                 520                 525

Gln Gln Asn Thr Pro Ile Gly Asp Gly Pro Val Leu Leu Pro Asp Asn
    530                 535                 540

His Tyr Leu Ser Thr Gln Ser Ala Leu Ser Lys Asp Pro Asn Glu Lys
545                 550                 555                 560

Arg Asp His Met Val Leu Leu Glu Phe Val Thr Ala Ala Gly Ile Thr
                565                 570                 575

Leu Gly Met Asp Glu Leu Tyr Lys
            580

<210> SEQ ID NO 12
<211> LENGTH: 11264
<212> TYPE: DNA
<213> ORGANISM: Artificial Sequence
<220> FEATURE:
<223> OTHER INFORMATION: Lentiviral vector pTRIP-CMV-AIM2 F27G-EGFP
<220> FEATURE:
<221> NAME/KEY: LTR
<222> LOCATION: (985)..(1618)
<220> FEATURE:
<221> NAME/KEY: PSI
<222> LOCATION: (1670)..(1807)
<220> FEATURE:
<221> NAME/KEY: RRE
<222> LOCATION: (2294)..(2498)
<220> FEATURE:
<221> NAME/KEY: CMV promoter
<222> LOCATION: (3203)..(3782)
<220> FEATURE:
<221> NAME/KEY: AIM2
<222> LOCATION: (3801)..(4829)
<220> FEATURE:
<221> NAME/KEY: Mutation F27G
<222> LOCATION: (3879)..(3881)
<220> FEATURE:
<221> NAME/KEY: EGFP
<222> LOCATION: (4836)..(5552)
<220> FEATURE:
<221> NAME/KEY: Sin LTR
<222> LOCATION: (5743)..(6004)

<400> SEQUENCE: 12
acataattgg acaaactacc tacagagatt taaagctcta aggtaaatat aaaattttta      60
agtgtataat gtgttaaact actgattcta attgtttgtg tatttagat tccaacctat     120

```
ggaactgatg aatgggagca gtggtggaat gcctttaatg aggaaaacct gttttgctca    180
gaagaaatgc catctagtga tgatgaggct actgctgact ctcaacattc tactcctcca    240
aaaaagaaga gaaaggtaga agaccccaag gactttcctt cagaattgct aagttttttg    300
agtcatgctg tgtttagtaa tagaactctt gcttgctttg ctatttacac cacaaaggaa    360
aaagctgcac tgctatacaa gaaaattatg gaaaaatatt ctgtaacctt tataagtagg    420
cataacagtt ataatcataa catactgttt tttcttactc cacacaggca tagagtgtct    480
gctattaata actatgctca aaaattgtgt acctttagct ttttaatttg taaaggggtt    540
aataaggaat atttgatgta tagtgccttg actagagatc ataatcagcc ataccacatt    600
tgtagaggtt ttacttgctt taaaaaacct cccacacctc cccctgaacc tgaaacataa    660
aatgaatgca attgttgttg ttaacttgtt tattgcagct tataatggtt acaaataaag    720
caatagcatc acaaatttca caaataaagc attttttttca ctgcattcta gttgtggttt    780
gtccaaactc atcaatgtat cttatcatgt ctggatcaac tggataactc aagctaacca    840
aaatcatccc aaacttccca ccccataccc tattaccact gccaattacc tgtggtttca    900
tttactctaa acctgtgatt cctctgaatt attttcattt taaagaaatt gtatttgtta    960
aatatgtact acaaacttag tagttggaag ggctaattca ctcccaaaga agacaagata   1020
tccttgatct gtggatctac cacacacaag gctacttccc tgattagcag aactacacac   1080
cagggccagg ggtcagatat ccactgacct ttggatggtg ctacaagcta gtaccagttg   1140
agccagataa ggtagaagag gccaataaag gagagaacac cagcttgtta caccctgtga   1200
gcctgcatgg gatggatgac ccggagagag aagtgttaga gtggaggttt gacagccgcc   1260
tagcatttca tcacgtggcc cgagagctgc atccggagta cttcaagaac tgctgatatc   1320
gagcttgcta aagggacttt ccgctgggga ctttccaggg aggcgtggcc tgggcgggga   1380
ctggggagtg gcgagccctc agatcctgca tataagcagc tgcttttttgc ctgtactggg   1440 tctctctggt tagaccagat ctgagcctgg gagctctctg gctaactagg gaacccactg   1500
cttaagcctc aataaagctt gccttgagtg cttcaagtag tgtgtgcccg tctgttgtgt   1560
gactctggta actagagatc cctcagaccc ttttagtcag tgtggaaaat ctctagcagt   1620
ggcgcccgaa cagggacttg aaagcgaaag ggaaaccaga ggagctctct cgacgcagga   1680
ctcggcttgc tgaagcgcgc acggcaagag gcgaggggcg cgactggtg agtacgccaa   1740 aaattttgac tagcggaggc tagaaggaga gagatgggtg cgagagcgtc agtattaagc   1800
gggggagaat tagatcgcga tgggaaaaaa ttcggttaag gccaggggga aagaaaaat   1860 ataaattaaa acatatagta tgggcaagca gggagctaga acgattcgca gttaatcctg   1920
gcctgttaga aacatcagaa ggctgtagac aaatactggg acagctacaa ccatcccttc   1980
agacaggatc agaagaactt agatcattat ataatacagt agcaaccctc tattgtgtgc   2040
atcaaaggat agagataaaa gacaccaagg aagctttaga caagatagag gaagagcaaa   2100
acaaaagtaa gaccaccgca cagcaagcgg ccgctgatct tcagacctgg aggaggagat   2160
atgagggaca attggagaag tgaattatat aaatataaag tagtaaaaat tgaaccatta   2220
ggagtagcac ccaccaaggc aaagagaaga gtggtgcaga gagaaaaaag agcagtggga   2280
ataggagctt tgttccttgg gttcttggga gcagcaggaa gcactatggg cgcagcgtca   2340
atgacgctga cggtacaggc cagacaatta ttgtctggta tagtgcagca gcagaacaat   2400
ttgctgaggg ctattgaggc gcaacagcat ctgttgcaac tcacagtctg ggcatcaag   2460 cagctccagg caagaatcct ggctgtggaa agatacctaa aggatcaaca gctcctgggg   2520
```

```
atttggggtt gctctggaaa actcatttgc accactgctg tgccttggaa tgctagttgg    2580
agtaataaat ctctggaaca gatttggaat cacacgacct ggatggagtg ggacagagaa    2640
attaacaatt acacaagctt aatacactcc ttaattgaag aatcgcaaaa ccagcaagaa    2700
aagaatgaac aagaattatt ggaattagat aaatgggcaa gtttgtggaa ttggtttaac    2760
ataacaaatt ggctgtggta tataaaatta ttcataatga tagtaggagg cttggtaggt    2820
ttaagaatag ttttgctgt actttctata gtgaatagag ttaggcaggg atattcacca     2880
ttatcgtttc agacccacct cccaaccccg aggggacccg acaggcccga aggaatagaa    2940
gaagaaggtg gagagagaga cagagacaga tccattcgat tagtgaacgg atctcgacgg    3000
tatcgccgaa ttcacaaatg gcagtattca tccacaattt taaaagaaaa gggggattg    3060 gggggtacag tgcaggggaa agaatagtag acataatagc aacagacata caaactaaag    3120
aattacaaaa acaaattaca aaaattcaaa attttcgggt ttattacagg gacagcagag    3180
atccactttg gctgatacgc gtatagtaat caattacggg gtcattagtt catagcccat    3240
atatggagtt ccgcgttaca taacttacgg taaatggccc gcctggctga ccgcccaacg    3300 accccccgccc attgacgtca ataatgacgt atgttcccat agtaacgcca atagggactt    3360
tccattgacg tcaatgggtg gagtatttac ggtaaactgc ccacttggca gtacatcaag    3420
tgtatcatat gccaagtacg cccctattg acgtcaatga cggtaaatgg cccgcctggc    3480
attatgccca gtacatgacc ttatgggact ttcctacttg gcagtacatc tacgtattag    3540
tcatcgctat taccatggtg atgcggtttt ggcagtacat caatgggcgt ggatagcggt    3600
ttgactcacg gggatttcca agtctccacc ccattgacgt caatgggagt ttgttttggc    3660
accaaaatca acgggacttt ccaaaatgtc gtaacaactc cgccccattg acgcaaatgg    3720
gcggtaggcg tgtacggtgg gaggtctata taagcagagc tggtttagtg aaccgtcaga    3780
tcccgcgggc tagcgccacc atggagagta aatacaagga gatactcttg ctaacaggcc    3840
tggataacat cactgatgag gaactggata ggtttaaggg ctttcttttca gacgagttta    3900 atattgccac aggcaaacta catactgcaa acagaataca agtagctacc ttgatgattc    3960
aaaatgctgg ggcggtgtct gcagtgatga agaccattcg tattttttcag aagttgaatt    4020 atatgctttt ggcaaaacgt cttcaggagg agaaggagaa agttgataag caatacaaat    4080
cggtaacaaa accaaagcca ctaagtcaag ctgaaatgag tcctgctgca tctgcagcca    4140
tcagaaatga tgtcgcaaag caacgtgctg caccaaaagt ctctcctcat gttaagcctg    4200
aacagaaaca gatggtggcc cagcaggaat ctatcagaga agggtttcag aagcgctgtt    4260
tgccagttat ggtactgaaa gcaaagaagc ccttcacgtt tgagacccaa gaaggcaagc    4320
aggagatgtt tcatgctaca gtggctacag aaaaggaatt cttctttgta aaagttttta    4380
atacactgct gaaagataaa ttcattccaa agagaataat tataatagca agatattatc    4440
ggcacagtgg tttcttagag gtaaaatagcg cctcacgtgt gttagatgct gaatctgacc    4500
aaaaggttaa tgtcccgctg aacattatca gaaaagctgg tgaaacccg aagatcaaca    4560 cgcttcaaac tcagcccctt ggaacaattg tgaatggttt gtttgtagtc cagaaggtaa    4620
cagaaaagaa gaaaaacata ttatttgacc taagtgacaa cactgggaaa atggaagtac    4680
tgggggttag aaacgaggac acaatgaaat gtaaggaagg agataaggtt cgacttacat    4740
tcttcacact gtcaaaaaat ggagaaaaac tacagctgac atctggagtt catagcacca    4800
taaaggttat taaggccaaa aaaaaaacaa ctagtatggt gagcaagggc gaggagctgt    4860
```

```
tcaccggggt ggtgcccatc ctggtcgagc tggacggcga cgtaaacggc cacaagttca    4920
gcgtgtccgg cgagggcgag ggcgatgcca cctacggcaa gctgaccctg aagttcatct    4980
gcaccaccgg caagctgccc gtgccctggc ccaccctcgt gaccaccctg acctacggcg    5040
tgcagtgctt cagccgctac cccgaccaca tgaagcagca cgacttcttc aagtccgcca    5100
tgcccgaagg ctacgtccag gagcgcacca tcttcttcaa ggacgacggc aactacaaga    5160
cccgcgccga ggtgaagttc gagggcgaca ccctggtgaa ccgcatcgag ctgaagggca    5220
tcgacttcaa ggaggacggc aacatcctgg ggcacaagct ggagtacaac tacaacagcc    5280
acaacgtcta tatcatggcc gacaagcaga agaacggcat caaggtgaac ttcaagatcc    5340
gccacaacat cgaggacggc agcgtgcagc tcgccgacca ctaccagcag aacacccca     5400
tcggcgacgg ccccgtgctg ctgcccgaca accactacct gagcacccag tccgccctga    5460
gcaaagaccc caacgagaag cgcgatcaca tggtcctgct ggagttcgtg accgccgccg    5520
ggatcactct cggcatggac gagctgtaca agtaactcga gacctagaaa acatggagc     5580
aatcacaagt agcaatacag cagctaccaa tgctgattgt gcctggctag aagcacaaga    5640
ggaggaggag gtgggttttc cagtcacacc tcaggtacct ttaagaccaa tgacttacaa    5700
ggcagctgta gatcttagcc acttttaaa agaaaagggg ggactggaag ggctaattca     5760
ctcccaacga agacaaaatc gtcgagagat gctgcatata agcagctgct ttttgcttgt    5820
actgggtctc tctggttaga ccagatctga gcctgggagc tctctggcta actagggaac    5880
ccactgctta agcctcaata aagcttgcct tgagtgcttc aagtagtgtg tgcccgtctg    5940
ttgtgtgact ctggtaacta gagatccctc agacccttt agtcagtgtg aaaatctct     6000
agcagtagta gttcatgtca tcttattatt cagtatttat aacttgcaaa gaaatgaata    6060
tcagagagtg agaggccttg acattataat agatttagca ggaattgaac taggagtgga    6120
gcacacaggc aaagctgcag aagtacttgg aagaagccac cagagatact cacgattctg    6180
cacatacctg gctaatccca gatcctaagg attacattaa gtttactaac atttatataa    6240
tgatttatag tttaaagtat aaacttatct aatttactat tctgacagat attaattaat    6300
cctcaaatat cataagagat gattactatt atccccattt aacacaagag gaaactgaga    6360
gggaaagatg ttgaagtaat tttcccacaa ttacagcatc cgttagttac gactctatga    6420
tcttctgaca caaattccat ttactcctca ccctatgact cagtcgaata tatcaaagtt    6480
atggacatta tgctaagtaa caaattaccc ttttatatag taaatactga gtagattgag    6540
agaagaaatt gtttgcaaac ctgaatagct tcaagaagaa gagaagtgag gataagaata    6600
acagttgtca tttaacaagt tttaacaagt aacttggtta gaaagggatt caaatgcata    6660
aagcaaggga taaattttc tggcaacaag actatacaat ataaccttaa atatgacttc     6720
aaataattgt tggaacttga taaaactaat taaatattat tgaagattat caatattata    6780
aatgtaattt acttttaaaa agggaacata gaaatgtgta tcattagagt agaaaacaat    6840
ccttattatc acaatttgtc aaaacaagtt tgttattaac acaagtagaa tactgcattc    6900
aattaagttg actgcagatt ttgtgttttg ttaaaattag aaagagataa caacaatttg    6960
aattattgaa agtaacatgt aaatagttct acatacgttc ttttgacatc ttgttcaatc    7020
attgatcgaa gttctttatc ttggaagaat tgttccaaa gactctgaaa taaggaaaac     7080
aatctattat atagtctcac acctttgttt tactttagt gatttcaatt taataatgta     7140
aatggttaaa atttattctt ctctgagatc atttcacatt gcagatagaa aacctgagac    7200
tgggtaatt tttattaaaa tctaatttaa tctcagaaac acatctttat ctaacatca     7260
```

```
attttttccag tttgatatta tcatataaag tcagccttcc tcatctgcag gttccacaac   7320
aaaaatccaa ccaactgtgg atcaaaaata ttgggaaaaa attaaaaata gcaatacaac   7380
aataaaaaaa tacaaatcag aaaaacagca cagtataaca actttattta gcatttacaa   7440
tctattaggt attataagta atctagccag atcctctacg ccggacgcat cgtggccggc   7500
atcaccggcg ccacaggtgc ggttgctggc gcctatatcg ccgacatcac cgatggggaa   7560
gatcgggctc gccacttcgg gctcatgagc gcttgtttcg cgtgggtat ggtggcaggc   7620
cccgtggccg ggggactgtt gggcgccatc tccttgcatg caccattcct tgcggcggcg   7680
gtgctcaacg gcctcaacct actactgggc tgcttcctaa tgcaggagtc gcataaggga   7740
gagcgtcgaa tggtgcactc tcagtacaat ctgctctgat gccgcatagt taagccagcc   7800
ccgacacccg ccaacacccg ctgacgcgcc ctgacgggct tgtctgctcc cggcatccgc   7860
ttacagacaa gctgtgaccg tctccgggag ctgcatgtgt cagaggtttt caccgtcatc   7920
accgaaacgc gcgagacgaa agggcctcgt gatacgccta ttttttatagg ttaatgtcat   7980
gataataatg gtttcttaga cgtcaggtgg cacttttcgg ggaaatgtgc gcggaacccc   8040
tatttgttta ttttttctaaa tacattcaaa tatgtatccg ctcatgagac aataaccctg   8100
ataaatgctt caataatatt gaaaaaggaa gagtatgagt attcaacatt tccgtgtcgc   8160
ccttattccc ttttttgcgg cattttgcct tcctgttttt gctcacccag aaacgctggt   8220
gaaagtaaaa gatgctgaag atcagttggg tgcacgagtg ggttacatcg aactggatct   8280
caacagcggt aagatccttg agagttttcg ccccgaagaa cgttttccaa tgatgagcac   8340
ttttaaagtt ctgctatgtg gcgcggtatt atcccgtatt gacgccgggc aagagcaact   8400
cggtcgccgc atacactatt ctcagaatga cttggttgag tactcaccag tcacagaaaa   8460
gcatcttacg gatggcatga cagtaagaga attatgcagt gctgccataa ccatgagtga   8520
taacactgcg gccaacttac ttctgacaac gatcggagga ccgaaggagc taaccgcttt   8580
tttgcacaac atgggggatc atgtaactcg ccttgatcgt tgggaaccgg agctgaatga   8640
agccatacca aacgacgagc gtgacaccac gatgcctgta gcaatggcaa caacgttgcg   8700
caaactatta actggcgaac tacttactct agcttcccgg caacaattaa tagactggat   8760
ggaggcggat aaagttgcag gaccacttct gcgctcggcc cttccggctg gctggtttat   8820
tgctgataaa tctggagccg gtgagcgtgg gtctcgcggt atcattgcag cactggggcc   8880
agatggtaag ccctcccgta tcgtagttat ctacacgacg gggagtcagg caactatgga   8940
tgaacgaaat agacagatcg ctgagatagg tgcctcactg attaagcatt ggtaactgtc   9000
agaccaagtt tactcatata ctttagat tgatttaaaa cttcatttt aatttaaaag   9060
gatctaggtg aagatccttt ttgataatct catgaccaaa atcccttaac gtgagttttc   9120
gttccactga gcgtcagacc ccgtagaaaa gatcaaagga tcttcttgag atcctttttt   9180
tctgcgcgta atctgctgct tgcaaacaaa aaaaccaccg ctaccagcgg tggtttgttt   9240
gccggatcaa gagctaccaa ctcttttttcc gaaggtaact ggcttcagca gagcgcagat   9300
accaaatact gttcttctag tgtagccgta gttaggccac cacttcaaga actctgtagc   9360
accgcctaca tacctcgctc tgctaatcct gttaccagtg gctgctgcca gtggcgataa   9420
gtcgtgtctt accgggttgg actcaagacg atagttaccg gataaggcgc agcggtcggg   9480
ctgaacgggg ggttcgtgca cacagcccag cttggagcga acgacctaca ccgaactgag   9540
atacctacag cgtgagctat gagaaagcgc cacgcttccc gaagggagaa aggcggacag   9600
```

```
gtatccggta agcggcaggg tcggaacagg agagcgcacg agggagcttc caggggaaa          9660 cgcctggtat ctttatagtc ctgtcgggtt tcgccacctc tgacttgagc gtcgattttt          9720
gtgatgctcg tcagggggc ggagcctatg gaaaaacgcc agcaacgcgg ccttttacg          9780 gttcctggcc ttttgctggc cttttgctca catgttcttt cctgcgttat ccctgattc          9840 tgtggataac cgtattaccg cctttgagtg agctgatacc gctcgccgca gccgaacgac          9900
cgagcgcagc gagtcagtga gcgaggaagc ggaagagcgc ccaatacgca aaccgcctct          9960
ccccgcgcgt tggccgattc attaatgcag ctgtggaatg tgtgtcagtt agggtgtgga         10020
aagtccccag gctccccagc aggcagaagt atgcaaagca tgcatctcaa ttagtcagca         10080
accaggtgtg gaaagtcccc aggctcccca gcaggcagaa gtatgcaaag catgcatctc         10140
aattagtcag caaccatagt cccgcccct a actccgccca tcccgcccct aactccgccc         10200
agttccgccc attctccgcc ccatggctga ctaatttttt tatttatgc agaggccgag          10260 gccgcctcgg cctctgagct attccagaag tagtgaggag gcttttttgg aggcctaggc         10320
ttttgcaaaa agcttggaca caagacaggc ttgcagata tgtttgagaa taccacttta         10380
tcccgcgtca gggagaggca gtgcgtaaaa agacgcggac tcatgtgaaa tactggtttt         10440
tagtgcgcca gatctctata atctcgcgca acctatttc ccctcgaaca cttttaagc          10500 cgtagataaa caggctggga cacttcacat gagcgaaaaa tacatcgtca cctgggacat         10560
gttgcagatc catgcacgta aactcgcaag ccgactgatg ccttctgaac aatggaaagg         10620
cattattgcc gtaagccgtg gcggtctgta ccgggtgcgt tactggcgcg tgaactgggt         10680
attcgtcatg tcgataccgt ttgtatttcc agctacgatc acgacaacca gcgcgagctt         10740
aaagtgctga acgcgcaga aggcgatggc gaaggcttca tcgttattga tgacctggtg         10800
gataccggtg gtactgcggt tgcgattcgt gaaatgtatc caaaagcgca ctttgtcacc         10860
atcttcgcaa aacccggctgg tcgtccgctg gttgatgact atgttgttga tatcccgcaa         10920
gataccggga ttgaacagcc gtgggatatg gcgtcgtat tcgtcccgcc aatctccggt         10980
cgctaatctt ttcaacgcct ggcactgccg ggcgttgttc ttttttaactt caggcgggtt         11040 acaatagttt ccagtaagta ttctggaggc tgcatccatg acacaggcaa acctgagcga         11100
aaccctgttc aaaccccgct ttaaacatcc tgaaacctcg acgctagtcc gccgctttaa         11160
tcacggcgca caaccgcctg tgcagtcggc ccttgatggt aaaaccatcc ctcactggta         11220
tcgcatgatt aaccgtctga tgtggatctg gcgcggcatt gacc                         11264
```

<210> SEQ ID NO 13
<211> LENGTH: 1644
<212> TYPE: DNA
<213> ORGANISM: Artificial Sequence
<220> FEATURE:
<223> OTHER INFORMATION: human gene cGAS mutated to generate E225A and
      D227A mutations and fused with GFP11 and FLAG
<220> FEATURE:
<221> NAME/KEY: CDS
<222> LOCATION: (1)..(1644)
<220> FEATURE:
<221> NAME/KEY: GFP11
<222> LOCATION: (1)..(51)
<220> FEATURE:
<221> NAME/KEY: FLAG
<222> LOCATION: (52)..(78)
<220> FEATURE:
<221> NAME/KEY: cGAS
<222> LOCATION: (79)..(1644)
<220> FEATURE:
<221> NAME/KEY: Mutation E225A
<222> LOCATION: (751)..(753)

```
<220> FEATURE:
<221> NAME/KEY: Mutation D227A
<222> LOCATION: (757)..(759)

<400> SEQUENCE: 13
```

| | | | | | | | | | | | | | | | | |
|---|---|---|---|---|---|---|---|---|---|---|---|---|---|---|---|---|
| atg | cgt | gac | cac | atg | gtc | ctt | cat | gag | tat | gta | aat | gct | gcc | ggt | atc | 48 |
| Met | Arg | Asp | His | Met | Val | Leu | His | Glu | Tyr | Val | Asn | Ala | Ala | Gly | Ile | |
| 1 | | | | 5 | | | | | 10 | | | | | 15 | | |
| acc | atg | gac | tac | aaa | gac | gat | gac | gac | aag | atg | cag | cct | tgg | cac | gga | 96 |
| Thr | Met | Asp | Tyr | Lys | Asp | Asp | Asp | Asp | Lys | Met | Gln | Pro | Trp | His | Gly | |
| | | | 20 | | | | | 25 | | | | | 30 | | | |
| aag | gcc | atg | cag | aga | gct | tcc | gag | gcc | gga | gcc | act | gcc | ccc | aag | gct | 144 |
| Lys | Ala | Met | Gln | Arg | Ala | Ser | Glu | Ala | Gly | Ala | Thr | Ala | Pro | Lys | Ala | |
| | | 35 | | | | | 40 | | | | | 45 | | | | |
| tcc | gca | cgg | aat | gcc | agg | ggc | gcc | ccg | atg | gat | ccc | aac | gag | tct | ccg | 192 |
| Ser | Ala | Arg | Asn | Ala | Arg | Gly | Ala | Pro | Met | Asp | Pro | Asn | Glu | Ser | Pro | |
| 50 | | | | | 55 | | | | | 60 | | | | | | |
| gct | gcc | ccc | gag | gcc | gcc | ctg | cct | aag | gcg | gga | aag | ttc | ggc | ccc | gcc | 240 |
| Ala | Ala | Pro | Glu | Ala | Ala | Leu | Pro | Lys | Ala | Gly | Lys | Phe | Gly | Pro | Ala | |
| 65 | | | | | 70 | | | | | 75 | | | | | 80 | |
| agg | aag | tcg | gga | tcc | cgg | cag | aaa | aag | agc | gcc | ccg | gac | acc | cag | gag | 288 |
| Arg | Lys | Ser | Gly | Ser | Arg | Gln | Lys | Lys | Ser | Ala | Pro | Asp | Thr | Gln | Glu | |
| | | | | 85 | | | | | 90 | | | | | 95 | | |
| agg | ccg | ccc | gtc | cgc | gca | act | ggg | gcc | cgc | gcc | aaa | aag | gcc | cct | cag | 336 |
| Arg | Pro | Pro | Val | Arg | Ala | Thr | Gly | Ala | Arg | Ala | Lys | Lys | Ala | Pro | Gln | |
| | | | 100 | | | | | 105 | | | | | 110 | | | |
| cgc | gcc | cag | gac | acg | cag | ccg | tct | gac | gcc | acc | agc | gcc | cct | ggg | gca | 384 |
| Arg | Ala | Gln | Asp | Thr | Gln | Pro | Ser | Asp | Ala | Thr | Ser | Ala | Pro | Gly | Ala | |
| | | 115 | | | | | 120 | | | | | 125 | | | | |
| gag | ggg | ctg | gag | cct | cct | gcg | gct | cgg | gag | ccg | gct | ctt | tcc | agg | gct | 432 |
| Glu | Gly | Leu | Glu | Pro | Pro | Ala | Ala | Arg | Glu | Pro | Ala | Leu | Ser | Arg | Ala | |
| | 130 | | | | | 135 | | | | | 140 | | | | | |
| ggt | tct | tgc | cgc | cag | agg | ggc | gcg | cgc | tgc | tcc | acg | aag | cca | aga | ccc | 480 |
| Gly | Ser | Cys | Arg | Gln | Arg | Gly | Ala | Arg | Cys | Ser | Thr | Lys | Pro | Arg | Pro | |
| 145 | | | | | 150 | | | | | 155 | | | | | 160 | |
| ccg | ccc | ggg | ccc | tgg | gac | gtg | ccc | agc | ccg | ggc | ctg | ccg | gtc | tcg | gcc | 528 |
| Pro | Pro | Gly | Pro | Trp | Asp | Val | Pro | Ser | Pro | Gly | Leu | Pro | Val | Ser | Ala | |
| | | | | 165 | | | | | 170 | | | | | 175 | | |
| ccc | att | ctc | gta | cgg | agg | gat | gcg | gcg | cct | ggg | gcc | tcg | aag | ctc | cgg | 576 |
| Pro | Ile | Leu | Val | Arg | Arg | Asp | Ala | Ala | Pro | Gly | Ala | Ser | Lys | Leu | Arg | |
| | | | 180 | | | | | 185 | | | | | 190 | | | |
| gcg | gtt | ttg | gag | aag | ttg | aag | ctc | agc | cgc | gat | gat | atc | tcc | acg | gcg | 624 |
| Ala | Val | Leu | Glu | Lys | Leu | Lys | Leu | Ser | Arg | Asp | Asp | Ile | Ser | Thr | Ala | |
| | | 195 | | | | | 200 | | | | | 205 | | | | |
| gcg | ggg | atg | gtg | aaa | ggg | gtt | gtg | gac | cac | ctg | ctg | ctc | aga | ctg | aag | 672 |
| Ala | Gly | Met | Val | Lys | Gly | Val | Val | Asp | His | Leu | Leu | Leu | Arg | Leu | Lys | |
| | 210 | | | | | 215 | | | | | 220 | | | | | |
| tgc | gac | tcc | gcg | ttc | aga | ggc | gtc | ggg | ctg | ctg | aac | acc | ggg | agc | tac | 720 |
| Cys | Asp | Ser | Ala | Phe | Arg | Gly | Val | Gly | Leu | Leu | Asn | Thr | Gly | Ser | Tyr | |
| 225 | | | | | 230 | | | | | 235 | | | | | 240 | |
| tat | gag | cac | gtg | aag | att | tct | gca | cct | aat | gca | ttt | gct | gtc | atg | ttt | 768 |
| Tyr | Glu | His | Val | Lys | Ile | Ser | Ala | Pro | Asn | Ala | Phe | Ala | Val | Met | Phe | |
| | | | | 245 | | | | | 250 | | | | | 255 | | |
| aaa | ctg | gaa | gtc | ccc | aga | att | caa | cta | gaa | gaa | tat | tcc | aac | act | cgt | 816 |
| Lys | Leu | Glu | Val | Pro | Arg | Ile | Gln | Leu | Glu | Glu | Tyr | Ser | Asn | Thr | Arg | |
| | | | 260 | | | | | 265 | | | | | 270 | | | |
| gca | tat | tac | ttt | gtg | aaa | ttt | aaa | aga | aat | ccg | aaa | gaa | aat | cat | ctg | 864 |
| Ala | Tyr | Tyr | Phe | Val | Lys | Phe | Lys | Arg | Asn | Pro | Lys | Glu | Asn | His | Leu | |
| | | 275 | | | | | 280 | | | | | 285 | | | | |
| agt | cag | ttt | tta | gaa | ggt | gaa | ata | tta | tca | gct | tct | aag | atg | ctg | tca | 912 |

```
                Ser Gln Phe Leu Glu Gly Glu Ile Leu Ser Ala Ser Lys Met Leu Ser
                    290                 295                 300 aag ttt agg aaa atc att aag gaa gaa att aac gac att aaa gat aca               960
Lys Phe Arg Lys Ile Ile Lys Glu Glu Ile Asn Asp Ile Lys Asp Thr
305                 310                 315                 320 gat gtc atc atg aag agg aaa aga gga ggg agc cct gct gta aca ctt              1008
Asp Val Ile Met Lys Arg Lys Arg Gly Gly Ser Pro Ala Val Thr Leu
                325                 330                 335 ctt att agt gaa aaa ata tct gtg gat ata acc ctg gct ttg gaa tca              1056
Leu Ile Ser Glu Lys Ile Ser Val Asp Ile Thr Leu Ala Leu Glu Ser
            340                 345                 350 aaa agt agc tgg cct gct agc acc caa gaa ggc ctg cgc att caa aac              1104
Lys Ser Ser Trp Pro Ala Ser Thr Gln Glu Gly Leu Arg Ile Gln Asn
        355                 360                 365 tgg ctt tca gca aaa gtt agg aag caa cta cga cta aag cca ttt tac              1152
Trp Leu Ser Ala Lys Val Arg Lys Gln Leu Arg Leu Lys Pro Phe Tyr
    370                 375                 380 ctt gta ccc aag cat gca aag gaa gga aat ggt ttc caa gaa gaa aca              1200
Leu Val Pro Lys His Ala Lys Glu Gly Asn Gly Phe Gln Glu Glu Thr
385                 390                 395                 400 tgg cgg cta tcc ttc tct cac atc gaa aag gaa att ttg aac aat cat              1248
Trp Arg Leu Ser Phe Ser His Ile Glu Lys Glu Ile Leu Asn Asn His
                405                 410                 415 gga aaa tct aaa acg tgc tgt gaa aac aaa gaa gag aaa tgt tgc agg              1296
Gly Lys Ser Lys Thr Cys Cys Glu Asn Lys Glu Glu Lys Cys Cys Arg
            420                 425                 430 aaa gat tgt tta aaa cta atg aaa tac ctt tta gaa cag ctg aaa gaa              1344
Lys Asp Cys Leu Lys Leu Met Lys Tyr Leu Leu Glu Gln Leu Lys Glu
        435                 440                 445 agg ttt aaa gac aaa aaa cat ctg gat aaa ttc tct tct tat cat gtg              1392
Arg Phe Lys Asp Lys Lys His Leu Asp Lys Phe Ser Ser Tyr His Val
    450                 455                 460 aaa act gcc ttc ttt cac gta tgt acc cag aac cct caa gac agt cag              1440
Lys Thr Ala Phe Phe His Val Cys Thr Gln Asn Pro Gln Asp Ser Gln
465                 470                 475                 480 tgg gac cgc aaa gac ctg ggc ctc tgc ttt gat aac tgc gtg aca tac              1488
Trp Asp Arg Lys Asp Leu Gly Leu Cys Phe Asp Asn Cys Val Thr Tyr
                485                 490                 495 ttt ctt cag tgc ctc agg aca gaa aaa ctt gag aat tat ttt att cct              1536
Phe Leu Gln Cys Leu Arg Thr Glu Lys Leu Glu Asn Tyr Phe Ile Pro
            500                 505                 510 gaa ttc aat cta ttc tct agc aac tta att gac aaa aga agt aaa gaa              1584
Glu Phe Asn Leu Phe Ser Ser Asn Leu Ile Asp Lys Arg Ser Lys Glu
        515                 520                 525 ttt ctg aca aag caa att gaa tat gaa aga aac aat gag ttt cca gtt              1632
Phe Leu Thr Lys Gln Ile Glu Tyr Glu Arg Asn Asn Glu Phe Pro Val
    530                 535                 540 ttt gat gaa ttt                                                              1644
Phe Asp Glu Phe
545

<210> SEQ ID NO 14
<211> LENGTH: 548
<212> TYPE: PRT
<213> ORGANISM: Artificial Sequence
<220> FEATURE:
<223> OTHER INFORMATION: Synthetic Construct

<400> SEQUENCE: 14

Met Arg Asp His Met Val Leu His Glu Tyr Val Asn Ala Ala Gly Ile
1               5                   10                  15
```

```
Thr Met Asp Tyr Lys Asp Asp Asp Lys Met Gln Pro Trp His Gly
            20              25              30
Lys Ala Met Gln Arg Ala Ser Glu Ala Gly Ala Thr Ala Pro Lys Ala
        35              40              45
Ser Ala Arg Asn Ala Arg Gly Ala Pro Met Asp Pro Asn Glu Ser Pro
50              55              60
Ala Ala Pro Glu Ala Ala Leu Pro Lys Ala Gly Lys Phe Gly Pro Ala
65              70              75              80
Arg Lys Ser Gly Ser Arg Gln Lys Lys Ser Ala Pro Asp Thr Gln Glu
            85              90              95
Arg Pro Pro Val Arg Ala Thr Gly Ala Arg Ala Lys Lys Ala Pro Gln
            100             105             110
Arg Ala Gln Asp Thr Gln Pro Ser Asp Ala Thr Ser Ala Pro Gly Ala
            115             120             125
Glu Gly Leu Glu Pro Pro Ala Ala Arg Glu Pro Ala Leu Ser Arg Ala
130             135             140
Gly Ser Cys Arg Gln Arg Gly Ala Arg Cys Ser Thr Lys Pro Arg Pro
145             150             155             160
Pro Pro Gly Pro Trp Asp Val Pro Ser Pro Gly Leu Pro Val Ser Ala
            165             170             175
Pro Ile Leu Val Arg Arg Asp Ala Ala Pro Gly Ala Ser Lys Leu Arg
            180             185             190
Ala Val Leu Glu Lys Leu Lys Leu Ser Arg Asp Asp Ile Ser Thr Ala
            195             200             205
Ala Gly Met Val Lys Gly Val Val Asp His Leu Leu Leu Arg Leu Lys
            210             215             220
Cys Asp Ser Ala Phe Arg Gly Val Gly Leu Leu Asn Thr Gly Ser Tyr
225             230             235             240
Tyr Glu His Val Lys Ile Ser Ala Pro Asn Ala Phe Ala Val Met Phe
            245             250             255
Lys Leu Glu Val Pro Arg Ile Gln Leu Glu Glu Tyr Ser Asn Thr Arg
            260             265             270
Ala Tyr Tyr Phe Val Lys Phe Lys Arg Asn Pro Lys Glu Asn His Leu
            275             280             285
Ser Gln Phe Leu Glu Gly Glu Ile Leu Ser Ala Ser Lys Met Leu Ser
            290             295             300
Lys Phe Arg Lys Ile Ile Lys Glu Glu Ile Asn Asp Ile Lys Asp Thr
305             310             315             320
Asp Val Ile Met Lys Arg Lys Arg Gly Gly Ser Pro Ala Val Thr Leu
            325             330             335
Leu Ile Ser Glu Lys Ile Ser Val Asp Ile Thr Leu Ala Leu Glu Ser
            340             345             350
Lys Ser Ser Trp Pro Ala Ser Thr Gln Glu Gly Leu Arg Ile Gln Asn
            355             360             365
Trp Leu Ser Ala Lys Val Arg Lys Gln Leu Arg Leu Lys Pro Phe Tyr
            370             375             380
Leu Val Pro Lys His Ala Lys Glu Gly Asn Gly Phe Gln Glu Glu Thr
385             390             395             400
Trp Arg Leu Ser Phe Ser His Ile Glu Lys Glu Ile Leu Asn Asn His
            405             410             415
Gly Lys Ser Lys Thr Cys Cys Glu Asn Lys Glu Glu Lys Cys Cys Arg
            420             425             430
```

```
Lys Asp Cys Leu Lys Leu Met Lys Tyr Leu Leu Glu Gln Leu Lys Glu
            435                 440                 445

Arg Phe Lys Asp Lys Lys His Leu Asp Lys Phe Ser Ser Tyr His Val
    450                 455                 460

Lys Thr Ala Phe Phe His Val Cys Thr Gln Asn Pro Gln Asp Ser Gln
465                 470                 475                 480

Trp Asp Arg Lys Asp Leu Gly Leu Cys Phe Asp Asn Cys Val Thr Tyr
                485                 490                 495

Phe Leu Gln Cys Leu Arg Thr Glu Lys Leu Glu Asn Tyr Phe Ile Pro
            500                 505                 510

Glu Phe Asn Leu Phe Ser Ser Asn Leu Ile Asp Lys Arg Ser Lys Glu
        515                 520                 525

Phe Leu Thr Lys Gln Ile Glu Tyr Glu Arg Asn Asn Glu Phe Pro Val
    530                 535                 540

Phe Asp Glu Phe
545

<210> SEQ ID NO 15
<211> LENGTH: 1047
<212> TYPE: DNA
<213> ORGANISM: Artificial Sequence
<220> FEATURE:
<223> OTHER INFORMATION: human gene H2B fused with GFP(1-10)
<220> FEATURE:
<221> NAME/KEY: CDS
<222> LOCATION: (1)..(1047)
<220> FEATURE:
<221> NAME/KEY: GFP1-10
<222> LOCATION: (1)..(663)
<220> FEATURE:
<221> NAME/KEY: H2B
<222> LOCATION: (664)..(1047)

<400> SEQUENCE: 15 atg tcc aaa gga gaa gaa ctg ttt acc ggt gtt gtg cca att ttg gtt      48
Met Ser Lys Gly Glu Glu Leu Phe Thr Gly Val Val Pro Ile Leu Val
1               5                   10                  15 gaa ctc gat ggt gat gtc aac gga cat aag ttc tca gtg aga ggc gaa      96
Glu Leu Asp Gly Asp Val Asn Gly His Lys Phe Ser Val Arg Gly Glu
            20                  25                  30 gga gaa ggt gac gcc acc att gga aaa ttg act ctt aaa ttc atc tgt     144
Gly Glu Gly Asp Ala Thr Ile Gly Lys Leu Thr Leu Lys Phe Ile Cys
        35                  40                  45 act act ggt aaa ctt cct gta cca tgg ccg act ctc gta aca acg ctt     192
Thr Thr Gly Lys Leu Pro Val Pro Trp Pro Thr Leu Val Thr Thr Leu
    50                  55                  60 acg tac gga gtt cag tgc ttt tcg aga tac cca gac cat atg aaa aga     240
Thr Tyr Gly Val Gln Cys Phe Ser Arg Tyr Pro Asp His Met Lys Arg
65                  70                  75                  80 cat gac ttt ttt aag tcg gct atg cct gaa ggt tac gtg caa gaa aga     288
His Asp Phe Phe Lys Ser Ala Met Pro Glu Gly Tyr Val Gln Glu Arg
                85                  90                  95 aca att tcg ttc aaa gat gat gga aaa tat aaa act aga gca gtt gtt     336
Thr Ile Ser Phe Lys Asp Asp Gly Lys Tyr Lys Thr Arg Ala Val Val
            100                 105                 110 aaa ttt gaa gga gat act ttg gtt aac cgc att gaa ctg aaa gga aca     384
Lys Phe Glu Gly Asp Thr Leu Val Asn Arg Ile Glu Leu Lys Gly Thr
        115                 120                 125 gat ttt aaa gaa gat ggt aat att ctt gga cac aaa ctc gaa tac aat     432
Asp Phe Lys Glu Asp Gly Asn Ile Leu Gly His Lys Leu Glu Tyr Asn
    130                 135                 140
```

| | | |
|---|---|---|
| ttt aat agt cat aac gta tac atc act gct gat aag caa aag aac gga<br>Phe Asn Ser His Asn Val Tyr Ile Thr Ala Asp Lys Gln Lys Asn Gly<br>145                    150                  155                  160 | 480 |
| att aaa gcg aat ttc aca gta cgc cat aat gta gaa gat ggc agt gtt<br>Ile Lys Ala Asn Phe Thr Val Arg His Asn Val Glu Asp Gly Ser Val<br>                  165                  170                  175 | 528 |
| caa ctt gcc gac cat tac caa caa aac acc cct att gga gac ggt ccg<br>Gln Leu Ala Asp His Tyr Gln Gln Asn Thr Pro Ile Gly Asp Gly Pro<br>                  180                  185                  190 | 576 |
| gta ctt ctt cct gat aat cac tac ctc tca aca caa aca gtc ctg agc<br>Val Leu Leu Pro Asp Asn His Tyr Leu Ser Thr Gln Thr Val Leu Ser<br>         195                  200                  205 | 624 |
| aaa gat cca aat gaa aaa gga aca ggt ggc gga agt atg cca gag<br>Lys Asp Pro Asn Glu Lys Gly Thr Gly Gly Gly Ser Met Pro Glu<br>210                  215                  220 | 672 |
| cca gcg aag tct gct ccc gcc ccg aaa aag ggc tcc aag aag gcg gtg<br>Pro Ala Lys Ser Ala Pro Ala Pro Lys Lys Gly Ser Lys Lys Ala Val<br>225                  230                  235                  240 | 720 |
| act aag gcg cag aag aaa ggc ggc aag aag cgc aag cgc agc cgc aag<br>Thr Lys Ala Gln Lys Lys Gly Gly Lys Lys Arg Lys Arg Ser Arg Lys<br>                  245                  250                  255 | 768 |
| gag agc tat tcc atc tat gtg tac aag gtt ctg aag cag gtc cac cct<br>Glu Ser Tyr Ser Ile Tyr Val Tyr Lys Val Leu Lys Gln Val His Pro<br>         260                  265                  270 | 816 |
| gac acc ggc att tcg tcc aag gcc atg ggc atc atg aat tcg ttt gtg<br>Asp Thr Gly Ile Ser Ser Lys Ala Met Gly Ile Met Asn Ser Phe Val<br>                  275                  280                  285 | 864 |
| aac gac att ttc gag cgc atc gca ggt gag gct tcc cgc ctg gcg cat<br>Asn Asp Ile Phe Glu Arg Ile Ala Gly Glu Ala Ser Arg Leu Ala His<br>290                    295                  300 | 912 |
| tac aac aag cgc tcg acc atc acc tcc agg gag atc cag acg gcc gtg<br>Tyr Asn Lys Arg Ser Thr Ile Thr Ser Arg Glu Ile Gln Thr Ala Val<br>305                    310                  315                  320 | 960 |
| cgc ctg ctg cct ggg gag ttg gcc aag cac gcc gtg tcc gag ggt<br>Arg Leu Leu Leu Pro Gly Glu Leu Ala Lys His Ala Val Ser Glu Gly<br>                  325                  330                  335 | 1008 |
| act aag gcc atc acc aag tac acc agc gct aag gat ccg<br>Thr Lys Ala Ile Thr Lys Tyr Thr Ser Ala Lys Asp Pro<br>                  340                  345 | 1047 |

<210> SEQ ID NO 16
<211> LENGTH: 349
<212> TYPE: PRT
<213> ORGANISM: Artificial Sequence
<220> FEATURE:
<223> OTHER INFORMATION: Synthetic Construct

<400> SEQUENCE: 16

Met Ser Lys Gly Glu Glu Leu Phe Thr Gly Val Val Pro Ile Leu Val
1                 5                    10                  15

Glu Leu Asp Gly Asp Val Asn Gly His Lys Phe Ser Val Arg Gly Glu
                  20                  25                  30

Gly Glu Gly Asp Ala Thr Ile Gly Lys Leu Thr Leu Lys Phe Ile Cys
         35                  40                  45

Thr Thr Gly Lys Leu Pro Val Pro Trp Pro Thr Leu Val Thr Thr Leu
 50                  55                  60

Thr Tyr Gly Val Gln Cys Phe Ser Arg Tyr Pro Asp His Met Lys Arg
65                70                  75                  80

His Asp Phe Phe Lys Ser Ala Met Pro Glu Gly Tyr Val Gln Glu Arg
                  85                  90                  95

```
Thr Ile Ser Phe Lys Asp Asp Gly Lys Tyr Lys Thr Arg Ala Val Val
            100                 105                 110

Lys Phe Glu Gly Asp Thr Leu Val Asn Arg Ile Glu Leu Lys Gly Thr
        115                 120                 125

Asp Phe Lys Glu Asp Gly Asn Ile Leu Gly His Lys Leu Glu Tyr Asn
130                 135                 140

Phe Asn Ser His Asn Val Tyr Ile Thr Ala Asp Lys Gln Lys Asn Gly
145                 150                 155                 160

Ile Lys Ala Asn Phe Thr Val Arg His Asn Val Glu Asp Gly Ser Val
                165                 170                 175

Gln Leu Ala Asp His Tyr Gln Gln Asn Thr Pro Ile Gly Asp Gly Pro
            180                 185                 190

Val Leu Leu Pro Asp Asn His Tyr Leu Ser Thr Gln Thr Val Leu Ser
        195                 200                 205

Lys Asp Pro Asn Glu Lys Gly Thr Gly Gly Gly Ser Met Pro Glu
210                 215                 220

Pro Ala Lys Ser Ala Pro Ala Pro Lys Lys Gly Ser Lys Lys Ala Val
225                 230                 235                 240

Thr Lys Ala Gln Lys Lys Gly Gly Lys Lys Arg Lys Arg Ser Arg Lys
                245                 250                 255

Glu Ser Tyr Ser Ile Tyr Val Tyr Lys Val Leu Lys Gln Val His Pro
            260                 265                 270

Asp Thr Gly Ile Ser Ser Lys Ala Met Gly Ile Met Asn Ser Phe Val
        275                 280                 285

Asn Asp Ile Phe Glu Arg Ile Ala Gly Glu Ala Ser Arg Leu Ala His
290                 295                 300

Tyr Asn Lys Arg Ser Thr Ile Thr Ser Arg Glu Ile Gln Thr Ala Val
305                 310                 315                 320

Arg Leu Leu Leu Pro Gly Glu Leu Ala Lys His Ala Val Ser Glu Gly
                325                 330                 335

Thr Lys Ala Ile Thr Lys Tyr Thr Ser Ala Lys Asp Pro
            340                 345

<210> SEQ ID NO 17
<211> LENGTH: 11472
<212> TYPE: DNA
<213> ORGANISM: Artificial Sequence
<220> FEATURE:
<223> OTHER INFORMATION: Lentiviral vector pTRIP-SFFV-GFP(1-10)-H2B-2A-
      GFP11-FLAG-cGAS E225A_D227A
<220> FEATURE:
<221> NAME/KEY: LTR
<222> LOCATION: (985)..(1618)
<220> FEATURE:
<221> NAME/KEY: PSI
<222> LOCATION: (1670)..(1807)
<220> FEATURE:
<221> NAME/KEY: RRE
<222> LOCATION: (2294)..(2498)
<220> FEATURE:
<221> NAME/KEY: Promoter SFFV
<222> LOCATION: (3203)..(3702)
<220> FEATURE:
<221> NAME/KEY: GFP-10
<222> LOCATION: (3721)..(4383)
<220> FEATURE:
<221> NAME/KEY: H2B
<222> LOCATION: (4384)..(4767)
<220> FEATURE:
<221> NAME/KEY: P2A
<222> LOCATION: (4774)..(4839)
<220> FEATURE:
```

```
<221> NAME/KEY: GFP11
<222> LOCATION: (4840)..(4890)
<220> FEATURE:
<221> NAME/KEY: FLAG
<222> LOCATION: (4891)..(4917)
<220> FEATURE:
<221> NAME/KEY: cGAS
<222> LOCATION: (4918)..(6483)
<220> FEATURE:
<221> NAME/KEY: Mutation E225A
<222> LOCATION: (5590)..(5592)
<220> FEATURE:
<221> NAME/KEY: Mutation D227A
<222> LOCATION: (5596)..(5598)
<220> FEATURE:
<221> NAME/KEY: Sin LTR
<222> LOCATION: (6674)..(6935)

<400> SEQUENCE: 17
```

| | | | | | |
|---|---|---|---|---|---|
| acataattgg | acaaactacc | tacagagatt | taaagctcta | aggtaaatat | aaaattttta       60 |
| agtgtataat | gtgttaaact | actgattcta | attgtttgtg | tattttagat | tccaacctat      120 |
| ggaactgatg | aatgggagca | gtggtggaat | gcctttaatg | aggaaaacct | gttttgctca      180 |
| gaagaaatgc | catctagtga | tgatgaggct | actgctgact | ctcaacattc | tactcctcca      240 |
| aaaaagaaga | gaaaggtaga | agaccccaag | gactttcctt | cagaattgct | aagttttttg      300 |
| agtcatgctg | tgtttagtaa | tagaactctt | gcttgctttg | ctatttacac | cacaaaggaa      360 |
| aaagctgcac | tgctatacaa | gaaaattatg | gaaaaatatt | ctgtaacctt | tataagtagg      420 |
| cataacagtt | ataatcataa | catactgttt | tttcttactc | cacacaggca | tagagtgtct      480 |
| gctattaata | actatgctca | aaaattgtgt | acctttagct | tttaatttg  | taagggggtt      540 |
| aataaggaat | atttgatgta | tagtgccttg | actagagatc | ataatcagcc | ataccacatt      600 |
| tgtagaggtt | ttacttgctt | taaaaaacct | cccacacctc | cccctgaacc | tgaaacataa      660 |
| aatgaatgca | attgttgttg | ttaacttgtt | tattgcagct | tataatggtt | acaaataaag      720 |
| caatagcatc | acaaatttca | caaataaagc | attttttca  | ctgcattcta | gttgtggttt      780 |
| gtccaaactc | atcaatgtat | cttatcatgt | ctggatcaac | tggataactc | aagctaacca      840 |
| aaatcatccc | aaacttccca | ccccatacc  | tattaccact | gccaattacc | tgtggtttca      900 |
| tttactctaa | acctgtgatt | cctctgaatt | attttcattt | taaagaaatt | gtatttgtta      960 |
| aatatgtact | acaaacttag | tagttggaag | ggctaattca | ctcccaaaga | agacaagata     1020 |
| tccttgatct | gtggatctac | cacacacaag | gctacttccc | tgattagcag | aactacacac     1080 |
| cagggccagg | ggtcagatat | ccactgacct | ttggatggtg | ctacaagcta | gtaccagttg     1140 |
| agccagataa | ggtagaagag | gccaataaag | gagagaacac | cagcttgtta | caccctgtga     1200 |
| gcctgcatgg | gatggatgac | ccggagagag | aagtgttaga | gtggaggttt | gacagccgcc     1260 |
| tagcatttca | tcacgtggcc | cgagagctgc | atccggagta | cttcaagaac | tgctgatatc     1320 |
| gagcttgcta | caagggactt | tccgctgggg | actttccagg | gaggcgtggc | ctgggcggga     1380 |
| ctggggagtg | gcgagccctc | agatcctgca | tataagcagc | tgcttttgc  | ctgtactggg     1440 |
| tctctctggt | tagaccagat | ctgagcctgg | gagctctctg | gctaactagg | gaacccactg     1500 |
| cttaagcctc | aataaagctt | gccttgagtg | cttcaagtag | tgtgtgcccg | tctgttgtgt     1560 |
| gactctggta | actagagatc | cctcagaccc | ttttagtcag | tgtggaaaat | ctctagcagt     1620 |
| ggcgcccgaa | cagggacttg | aaagcgaaag | ggaaaccaga | ggagctctct | cgacgcagga     1680 |
| ctcggcttgc | tgaagcgcgc | acggcaagag | gcgaggggcg | gcgactggtg | agtacgccaa     1740 |
| aaattttgac | tagcggaggc | tagaaggaga | gagatgggtg | cgagagcgtc | agtattaagc     1800 |

```
gggggagaat tagatcgcga tgggaaaaaa ttcggttaag gccagggggca aagaaaaaat    1860
ataaattaaa acatatagta tgggcaagca gggagctaga acgattcgca gttaatcctg    1920
gcctgttaga acatcagaa ggctgtagac aaatactggg acagctacaa ccatcccttc     1980
agacaggatc agaagaactt agatcattat ataatacagt agcaaccctc tattgtgtgc    2040
atcaaaggat agagataaaa gacaccaagg aagctttaga caagatagag gaagagcaaa   2100
acaaaagtaa gaccaccgca cagcaagcgg ccgctgatct tcagacctgg aggaggagat   2160
atgagggaca attggagaag tgaattatat aaatataaag tagtaaaaat tgaaccatta   2220
ggagtagcac ccaccaaggc aaagagaaga gtggtgcaga gagaaaaaag agcagtggga   2280
ataggagctt tgttccttgg gttcttggga gcagcaggaa gcactatggg cgcagcgtca   2340
atgacgctga cggtacaggc cagacaatta ttgtctggta tagtgcagca gcagaacaat   2400
ttgctgaggg ctattgaggc gcaacagcat ctgttgcaac tcacagtctg gggcatcaag   2460
cagctccagg caagaatcct ggctgtggaa agatacctaa aggatcaaca gctcctgggg   2520
atttggggtt gctctggaaa actcatttgc accactgctg tgccttggaa tgctagttgg   2580
agtaataaat ctctggaaca gatttggaat cacacgacct ggatggagtg ggacagagaa   2640
attaacaatt acacaagctt aatacactcc ttaattgaag aatcgcaaaa ccagcaagaa   2700
aagaatgaac aagaattatt ggaattagat aaatgggcaa gtttgtggaa ttggtttaac   2760
ataacaaatt ggctgtggta tataaaatta ttcataatga tagtaggagg cttggtaggt   2820
ttaagaatag tttttgctgt actttctata gtgaatagag ttaggcaggg atattcacca   2880
ttatcgtttc agacccacct cccaaccccg aggggacccg acaggcccga aggaatagaa   2940
gaagaaggtg gagagagaga cagagacaga tccattcgat tagtgaacgg atctcgacgg   3000
tatcgccgaa ttcacaaatg gcagtattca tccacaattt taaaagaaaa ggggggattg   3060
gggggtacag tgcaggggaa agaatagtag acataatagc aacagacata caaactaaag   3120
aattacaaaa acaaattaca aaaattcaaa attttcgggt ttattacagg gacagcagag   3180
atccactttg gctgatacgc gtatagtaat caattacggg gtcattagtt catagcccat   3240
atatggagtt ccgcgttaca taacttacgg taaatggccc gcctggctga ccgcccaacg   3300
accccccgcc attgacgtca ataatgacgt atgttcccat agtaacgcca atagggactt   3360
tccattgacg tcaatgggtg gagtatttac ggtaaactgc ccacttggca gtacatcaag   3420
tgtatcatat gccaagtacg ccccctattg acgtcaatga cggtaaatgg cccgcctggc   3480
attatgccca gtacatgacc ttatgggact ttcctacttg gcagtacatc tacgtattag   3540
tcatcgctat taccatggtg atgcggtttt ggcagtacat caatgggcgt ggatagcggt   3600
ttgactcacg gggatttcca agtctccacc ccattgacgt caatgggagt ttgttttggc   3660
accaaaatca acgggacttt ccaaaatgtc gtaacaactc cgccccattg acgcaaatgg   3720
gcggtaggcg tgtacggtgg gaggtctata taagcagagc tggtttagtg aaccgtcaga   3780
tcccgcgggc tagcgccacc atggagagta aatacaagga gatactcttg ctaacaggcc   3840
tggataacat cactgatgag gaactggata ggtttaaggg ctttctttca gacgagttta   3900
atattgccac aggcaaacta catactgcaa acagaataca agtagctacc ttgatgattc   3960
aaaatgctgg ggcggtgtct gcagtgatga agaccattcg tattttcag aagttgaatt    4020
atatgctttt ggcaaaacgt cttcaggagg agaaggagaa agttgataag caatacaaat   4080
cggtaacaaa accaaagcca ctaagtcaag ctgaaatgag tcctgctgca tctgcagcca   4140
```

```
tcagaaatga tgtcgcaaag caacgtgctg caccaaaagt ctctcctcat gttaagcctg    4200
aacagaaaca gatggtggcc cagcaggaat ctatcagaga agggtttcag aagcgctgtt    4260
tgccagttat ggtactgaaa gcaaagaagc ccttcacgtt tgagacccaa gaaggcaagc    4320
aggagatgtt tcatgctaca gtggctacag aaaaggaatt cttctttgta aaagttttta    4380
atacactgct gaaagataaa ttcattccaa agagaataat tataatagca agatattatc    4440
ggcacagtgg tttcttagag gtaaatagcg cctcacgtgt gttagatgct gaatctgacc    4500
aaaaggttaa tgtcccgctg aacattatca gaaaagctgg tgaaacccccg aagatcaaca    4560 cgcttcaaac tcagcccctt ggaacaattg tgaatggttt gtttgtagtc cagaaggtaa    4620
cagaaaagaa gaaaaacata ttatttgacc taagtgacaa cactgggaaa atggaagtac    4680
tgggggttag aaacgaggac acaatgaaat gtaaggaagg agataaggtt cgacttacat    4740
tcttcacact gtcaaaaaat ggagaaaaac tacagctgac atctggagtt catagcacca    4800
taaaggttat taaggccaaa aaaaaaacaa ctagtatggt gagcaagggc gaggagctgt    4860
tcaccggggt ggtgcccatc ctggtcgagc tggacggcga cgtaaacggc cacaagttca    4920
gcgtgtccgg cgagggcgag ggcgatgcca cctacggcaa gctgaccctg aagttcatct    4980
gcaccaccgg caagctgccc gtgccctggc ccaccctcgt gaccaccctg acctacggcg    5040
tgcagtgctt cagccgctac cccgaccaca tgaagcagca cgacttcttc aagtccgcca    5100
tgcccgaagg ctacgtccag gagcgcacca tcttcttcaa ggacgacggc aactacaaga    5160
cccgcgccga ggtgaagttc gagggcgaca ccctggtgaa ccgcatcgag ctgaagggca    5220
tcgacttcaa ggaggacggc aacatcctgg ggcacaagct ggagtacaac tacaacagcc    5280
acaacgtcta tatcatggcc gacaagcaga gaacggcat caaggtgaac ttcaagatcc    5340
gccacaacat cgaggacggc agcgtgcagc tcgccgacca ctaccagcag aacacccccca    5400 tcggcgacgg ccccgtgctg ctgcccgaca ccactacct gagcacccag tccgccctga    5460
gcaaagaccc caacgagaag cgcgatcaca tggtcctgct ggagttcgtg accgccgccg    5520
ggatcactct cggcatggac gagctgtaca gtaactcga acctagaaaa acatggagc    5580 aatcacaagt agcaatacag cagctaccaa tgctgattgt gcctggctag aagcacaaga    5640
ggaggaggag gtgggttttc cagtcacacc tcaggtacct ttaagaccaa tgacttacaa    5700
ggcagctgta gatcttagcc acttttttaaa agaaaagggg ggactggaag gctaattca    5760 ctcccaacga agacaaaatc gtcgagagat gctgcatata agcagctgct ttttgcttgt    5820
actgggtctc tctggttaga ccagatctga gcctgggagc tctctggcta actagggaac    5880
ccactgctta agcctcaata aagcttgcct tgagtgcttc aagtagtgtg tgcccgtctg    5940
ttgtgtgact ctggtaacta gagatccctc agaccctttt agtcagtgtg gaaaatctct    6000
agcagtagta gttcatgtca tcttattatt cagtatttat aacttgcaaa gaaatgaata    6060
tcagagagtg agaggccttg acattataat agatttagca ggaattgaac taggagtgga    6120
gcacacaggc aaagctgcag aagtacttgg aagaagccac cagagatact cacgattctg    6180
cacatacctg gctaatccca gatcctaagg attacattaa gtttactaac atttatataa    6240
tgatttatag tttaaagtat aaacttatct aatttactat tctgacagat attaattaat    6300
cctcaaatat cataagagat gattactatt atccccattt aacacaagag gaaactgaga    6360
gggaaagatg ttgaagtaat tttcccacaa ttcagcatc cgttagttac gactctatga    6420
tcttctgaca caaattccat ttactcctca ccctatgact cagtcgaata tatcaaagtt    6480
atggacatta tgctaagtaa caaattaccc ttttatatag taaatactga gtagattgag    6540
```

| | |
|---|---|
| agaagaaatt gtttgcaaac ctgaatagct tcaagaagaa gagaagtgag gataagaata | 6600 |
| acagttgtca tttaacaagt tttaacaagt aacttggtta gaaagggatt caaatgcata | 6660 |
| aagcaaggga taaattttc tggcaacaag actatacaat ataaccttaa atatgacttc | 6720 |
| aaataattgt tggaacttga taaaactaat taaatattat tgaagattat caatattata | 6780 |
| aatgtaattt acttttaaaa agggaacata gaaatgtgta tcattagagt agaaaacaat | 6840 |
| ccttattatc acaatttgtc aaaacaagtt tgttattaac acaagtagaa tactgcattc | 6900 |
| aattaagttg actgcagatt ttgtgttttg ttaaaattag aaagagataa caacaatttg | 6960 |
| aattattgaa agtaacatgt aaatagttct acatacgttc ttttgacatc ttgttcaatc | 7020 |
| attgatcgaa gttctttatc ttggaagaat ttgttccaaa gactctgaaa taaggaaaac | 7080 |
| aatctattat atagtctcac acctttgttt tacttttagt gatttcaatt taataatgta | 7140 |
| aatggttaaa atttattctt ctctgagatc atttcacatt gcagatagaa aacctgagac | 7200 |
| tggggtaatt tttattaaaa tctaatttaa tctcagaaac acatctttat tctaacatca | 7260 |
| attttttccag tttgatatta tcatataaag tcagccttcc tcatctgcag gttccacaac | 7320 |
| aaaaatccaa ccaactgtgg atcaaaaata ttgggaaaaa attaaaaata gcaatacaac | 7380 |
| aataaaaaaa tacaaatcag aaaaacagca cagtataaca actttattta gcatttacaa | 7440 |
| tctattaggt attataagta atctagccag atcctctacg ccggacgcat cgtggccggc | 7500 |
| atcaccggcg ccacaggtgc ggttgctggc gcctatatcg ccgacatcac cgatggggaa | 7560 |
| gatcgggctc gccacttcgg gctcatgagc gcttgtttcg gcgtgggtat ggtggcaggc | 7620 |
| cccgtggccg ggggactgtt gggcgccatc tccttgcatg caccattcct tgcggcggcg | 7680 |
| gtgctcaacg gcctcaacct actactgggc tgcttcctaa tgcaggagtc gcataaggga | 7740 |
| gagcgtcgaa tggtgcactc tcagtacaat ctgctctgat gccgcatagt taagccagcc | 7800 |
| ccgacacccg ccaacacccg ctgacgcgcc ctgacgggct tgtctgctcc cggcatccgc | 7860 |
| ttacagacaa gctgtgaccg tctccgggag ctgcatgtgt cagaggtttt caccgtcatc | 7920 |
| accgaaacgc gcgagacgaa agggcctcgt gatacgccta ttttataggt taatgtcat | 7980 |
| gataataatg gtttcttaga cgtcaggtgg cacttttcgg ggaaatgtgc gcggaacccc | 8040 |
| tatttgttta ttttttctaaa tacattcaaa tatgtatccg ctcatgagac aataaccctg | 8100 |
| ataaatgctt caataatatt gaaaaaggaa gagtatgagt attcaacatt tccgtgtcgc | 8160 |
| ccttattccc ttttttgcgg cattttgcct tcctgttttt gctcacccag aaacgctggt | 8220 |
| gaaagtaaaa gatgctgaag atcagttggg tgcacgagtg ggttacatcg aactggatct | 8280 |
| caacagcggt aagatccttg agagttttcg ccccgaagaa cgttttccaa tgatgagcac | 8340 |
| ttttaaagtt ctgctatgtg gcgcggtatt atcccgtatt gacgccgggc aagagcaact | 8400 |
| cggtcgccgc atacactatt ctcagaatga cttggttgag tactcaccag tcacagaaaa | 8460 |
| gcatcttacg gatggcatga cagtaagaga attatgcagt gctgccataa ccatgagtga | 8520 |
| taacactgcg gccaacttac ttctgacaac gatcggagga ccgaaggagc taaccgcttt | 8580 |
| tttgcacaac atgggggatc atgtaactcg ccttgatcgt tgggaaccgg agctgaatga | 8640 |
| agccatacca aacgacgagc gtgacaccac gatgcctgta gcaatggcaa caacgttgcg | 8700 |
| caaactatta actggcgaac tacttactct agcttcccgg caacaattaa tagactggat | 8760 |
| ggaggcggat aaagttgcag gaccacttct gcgctcggcc cttccggctg gctggtttat | 8820 |
| tgctgataaa tctggagccg gtgagcgtgg gtctcgcggt atcattgcag cactggggcc | 8880 |

```
agatggtaag ccctcccgta tcgtagttat ctacacgacg gggagtcagg caactatgga    8940
tgaacgaaat agacagatcg ctgagatagg tgcctcactg attaagcatt ggtaactgtc    9000
agaccaagtt tactcatata tactttagat tgatttaaaa cttcattttt aatttaaaag    9060
gatctaggtg aagatccttt ttgataatct catgaccaaa atcccttaac gtgagttttc    9120
gttccactga gcgtcagacc ccgtagaaaa gatcaaagga tcttcttgag atccttttttt   9180
tctgcgcgta atctgctgct tgcaaacaaa aaaaccaccg ctaccagcgg tggtttgttt    9240
gccggatcaa gagctaccaa ctcttttttcc gaaggtaact ggcttcagca gagcgcagat    9300
accaaatact gttcttctag tgtagccgta gttaggccac cacttcaaga actctgtagc    9360
accgcctaca tacctcgctc tgctaatcct gttaccagtg gctgctgcca gtggcgataa    9420
gtcgtgtctt accgggttgg actcaagacg atagttaccg gataaggcgc agcggtcggg    9480
ctgaacgggg ggttcgtgca cacagcccag cttggagcga acgacctaca ccgaactgag    9540
atacctacag cgtgagctat gagaaagcgc cacgcttccc gaagggagaa aggcggacag    9600
gtatccggta agcggcaggg tcggaacagg agagcgcacg agggagcttc caggggggaaa   9660
cgcctggtat ctttatagtc ctgtcgggtt tcgccacctc tgacttgagc gtcgattttt    9720
gtgatgctcg tcaggggggc ggagcctatg gaaaaacgcc agcaacgcgg cctttttacg    9780
gttcctggcc ttttgctggc cttttgctca catgttcttt cctgcgttat cccctgattc    9840
tgtggataac cgtattaccg cctttgagtg agctgatacc gctcgccgca gccgaacgac    9900
cgagcgcagc gagtcagtga gcgaggaagc ggaagagcgc ccaatacgca aaccgcctct    9960
ccccgcgcgt tggccgattc attaatgcag ctgtggaatg tgtgtcagtt agggtgtgga   10020
aagtccccag gctccccagc aggcagaagt atgcaaagca tgcatctcaa ttagtcagca   10080
accaggtgtg gaaagtcccc aggctcccca gcaggcagaa gtatgcaaag catgcatctc   10140
aattagtcag caaccatagt cccgccccta actccgccca tcccgcccct aactccgccc   10200
agttccgccc attctccgcc ccatggctga ctaattttttt ttatttatgc agaggccgag   10260
gccgcctcgg cctctgagct attccagaag tagtgaggag gcttttttgg aggcctaggc   10320
ttttgcaaaa agcttggaca caagacaggc ttgcagagata tgtttgagaa taccacttta   10380
tcccgcgtca gggagaggca gtgcgtaaaa agacgcggac tcatgtgaaa tactggtttt   10440
tagtgcgcca gatctctata atctcgcgca acctatttt ccctcgaaca ctttttaagc   10500
cgtagataaa caggctggga cacttcacat gagcgaaaaa tacatcgtca cctgggacat   10560
gttgcagatc catgcacgta aactcgcaag ccgactgatg ccttctgaac aatggaaagg   10620
cattattgcc gtaagccgtg gcggtctgta ccgggtgcgt tactggcgcg tgaactgggt   10680
attcgtcatg tcgataccgt ttgtatttcc agctacgatc acgacaacca gcgcgagctt   10740
aaagtgctga acgcgcaga aggcgatggc gaaggcttca tcgttattga tgacctggtg   10800
gataccggtg gtactgcggt tgcgattcgt gaaatgtatc caaaagcgca ctttgtcacc   10860
atcttcgcaa aaccggctgg tcgtccgctg gttgatgact atgttgttga tatcccgcaa   10920
gataccggga ttgaacagcc gtgggatatg ggcgtcgtat tcgtcccgcc aatctccggt   10980
cgctaatctt tcaacgcct ggcactgccg ggcgttgttc tttttaactt caggcggtt    11040
acaatagttt ccagtaagta ttctggaggc tgcatccatg acacaggcaa acctgagcga   11100
aaccctgttc aaacccgct ttaaacatcc tgaaacctcg acgctagtcc gccgctttaa   11160
tcacggcgca caaccgcctg tgcagtcggc ccttgatggt aaaaccatcc ctcactggta   11220
tcgcatgatt aaccgtctga tgtggatctg gcgcggcatt gacccacgcg aaatcctcga   11280
```

```
cgtccaggca cgtattgtga tgagcgatgc cgaacgtacc gacgatgatt tatacgatac  11340
ggtgattggc taccgtggcg gcaactggat ttatgagtgg gccccggatc tttgtgaagg  11400
aaccttactt ctgtggtgtg acataattgg acaaactacc tacagagatt taaagctcta  11460
aggtaatata aa                                                      11472
```

METHOD TO MONITOR AND QUANTIFY INTERPHASE NUCLEAR ENVELOPE RUPTURE EVENTS

CROSS-REFERENCE TO RELATED APPLICATION

This application is the U.S. national stage application of International Patent Application No. PCT/EP2017/053665, filed Feb. 17, 2017.

The Sequence Listing for this application is labeled "Seq-List.txt" which was created on Jul. 31, 2018 and is 109 KB. The entire content of the sequence listing is incorporated herein by reference in its entirety.

FIELD OF THE INVENTION

The present invention relates to the field of medicine, in particular of oncology, immunity and aging. It provides new methods for studying interphase nuclear envelope rupture events and for screening compounds capable of modifying their intensity and/or frequency.

BACKGROUND OF THE INVENTION

The nuclear envelope is a physical barrier that separates the nucleus from the cytoplasm. It has a complex structure consisting of two nuclear membranes, the inner and the outer nuclear membranes, an underlying nuclear lamina, and nuclear pore complexes. It fulfills at least three essential functions in eukaryotic cells: first it regulates the movements of molecules between the nucleus and the cytoplasm by active, signal-dependent transport via aqueous channels that are formed by the nuclear pore complexes, second it creates a permeability barrier that prevents the passive diffusion of molecules larger than ~60 kDa across the nuclear envelope and, third it provides the structural framework of the nucleus. In particular, the nuclear lamina is an intimately connected meshwork of intermediate filament proteins, providing structural support to the nuclear envelop and having a central role in defining nuclear organization.

The nuclear envelope is not aimed to remain intact during the whole cell cycle. It's indeed a dynamic structure that undergoes complete disassembly and reformation during mitosis. The nuclear envelope breakdown occurs at the onset of mitosis and facilitates the equal segregation of the genome and other cellular components into two daughter cells. However, an intact nuclear permeability barrier is generally considered to be a prerequisite for nuclear transport and to be critical for proper cell compartmentalization during interphase.

Under pathological circumstances, it has been shown that the nuclear envelope can be breached in non-mitotic cells. Indeed, the nuclear envelope can bud during viral infection (Lee C P et al, Plos Pathog, 2012, 8(9), e1002904) or be completely breached in laminopathies, pathologies associated to mutations in genes coding for nuclear lamina proteins, especially in LMN A/C (Hatch E et al, J Cell Biol, 2014, 205(2), pp. 131-141; De Vos W H et al, Hum Mol Genet, 2011, 20(21), pp. 4175-4186). The nuclear envelope can also be transiently breached during interphase of cancer cells (Vargas D J et al, Nucleus, 2012, 3(1), pp. 88-100). This tendency of breaches in cancer cells might be correlated to mutations in LMN A/C, such mutations have been found in many cancer cells. The cancer cells which express lower levels of LMN A/C, also present a higher degree of metastatic potential (Harada T et al, J Cell Biol, 2014, 204(5), pp. 669-682), potentially because it makes their nuclei more deformable, and thus allow them to migrate through narrower pores and to invade tissues. Importantly, a recent study demonstrated that complete removal of this protein leads to an increase in cell death during transmigration, and eventually reduces the extent of metastasis (Harada T et al).

Similarly to cancer cells, several types of immune cells have also been reported to express lower levels of LMNA/C.

Despite evidences that connect interphase nuclear envelope rupture events to cancer and immunity, there is actually no reliable method to study nuclear envelope breaching events.

Indeed, breaches in the nuclear envelope are too small and transient to be directly studied. However, when a breach occurs in the nuclear envelope, molecules can transiently diffuse from the nucleus to the cytoplasm or from the cytoplasm to the nucleus.

Many proteins possess a localization signal for either the nucleus (Nuclear Localization Signal, NLS), or the cytoplasm (Nuclear Export Signal, NES). These localization signals allow the proteins who express them to be addressed to the proper compartment or to go back to it in case of abnormal localization.

A fusion protein of EGFP (Enhanced Green Fluorescent Protein) and NLS has been used to study interphase nuclear envelope rupture events (Vargas D J et al). If it is possible to follow the movements of such a protein out of the nucleus after a breach in the nuclear envelope, the signal is very transitory since these proteins will be redirected to their normal compartment as soon as the breach will be repaired. To be able to efficiently quantify, in a population of cells, the intensity and/or frequency of interphase nuclear envelope rupture events, the signal need to be strong and persistent, even after nuclear envelope reparation. Indeed, with the method developed by Vargas D J et al, it's not possible to count, in a population of fixed cells, the proportion of cells which have recently experienced a nuclear envelope rupture event. It's a huge limitation for experimental studies and it makes it impossible to develop any screening test.

There is thus still a strong need to provide new methods that allow to study efficiently interphase nuclear envelope rupture events and to screen new compounds that can modulate the intensity and/or frequency of these events. The present invention seeks to meet these and other needs.

SUMMARY OF THE INVENTION

The inventors have discovered a new method that allows to detect interphase nuclear envelope rupture events, even hours after the event occurred. This method can also be used to screen compounds capable of modulating the intensity and/or the frequency of these events.

Accordingly, in a first aspect, the present invention concerns the use of an in vitro method for screening or identifying a compound capable of increasing or decreasing the intensity and/or frequency of interphase nuclear envelope rupture events in eukaryotic cells comprising:
(a) providing a eukaryotic cell expressing a protein fused to a detection entity and having a cytosolic non-nuclear localization in interphase, in particular an exclusive cytosolic non-nuclear localization, and a non-sequence specific DNA binding activity; and
(b) contacting said cell with a test compound; and
(c) measuring the intensity and/or frequency of interphase nuclear envelope rupture events in said cell, said interphase nuclear envelope rupture events being characterized by the presence of said protein in the nucleus of said cell; and (d) comparing the intensity and/or frequency of said interphase nuclear envelope rupture events with a reference level in the absence of said test compound and determining if said compound increases or decreases the intensity and/or frequency of said interphase nuclear envelope rupture events.

Preferably, said method further comprises a step of selecting the compound which increases or decreases the intensity and/or frequency of said interphase nuclear envelope rupture events.

The present invention also concerns, in a second aspect, an in vitro method for monitoring interphase nuclear envelope rupture events in a eukaryotic cell comprising:
(a) expressing a protein fused to a detection entity and having a cytosolic non-nuclear localization in interphase, in particular an exclusive cytosolic non-nuclear localization, and a non-sequence specific DNA binding activity in a eukaryotic cell or providing a eukaryotic cell expressing a protein being fused to a detection entity and having a cytosolic non-nuclear localization in interphase and a non-sequence specific DNA binding activity;
(b) measuring the intensity and/or frequency of interphase nuclear envelope rupture events, said interphase nuclear envelope rupture events being characterized by the presence of said protein in the nucleus of said cell; and
(c) optionally, comparing the intensity and/or frequency of said interphase nuclear envelope rupture events with a reference level.

Preferably, said method further comprises a step of submitting said cell to an experimental procedure and a step of determining if said experimental procedure increases or decreases the intensity and/or frequency of said interphase nuclear envelope rupture events in said cell.

Preferably, the protein is selected from the group consisting of a cGAS protein and an AIM2 protein, more preferably the protein is selected from the group consisting of human cGAS (SEQ ID NO: 1) and human AIM2 (SEQ ID NO: 2), even more preferably the protein is the human cGAS.

Preferably, the protein has lost its function, more preferably its catalytic or enzymatic function, even more preferably the protein is a human cGAS that presents an E225A mutation and/or a D227A mutation or a human AIM2 that presents a F27G mutation.

Preferably, the protein is stably expressed in the cell.

Preferably, the protein has a molecular weight above about 40 kDa, preferably above about 60 kDa.

Preferably, the protein is fused to a detection entity selected from the group consisting of a tag, an enzyme or a fluorescent protein, more preferably the detection entity is a fluorescent protein or a part thereof, still more preferably the detection entity is a fluorescent protein selected from the group consisting of GFP, EGFP, sfGFP, RFP, TagBFP, mTagBFP2, tagRFP, tdTomato, mCherry, sfCherry, Venus, TagRFP657, and a part thereof, and even more preferably the protein is fused to, GFP, EGFP, sfGFP, or a part thereof.

Preferably, the intensity and/or frequency of the interphase nuclear envelope rupture events are measured on a population of between 10 cells and between about 10,000,000 cells, preferably between about 50 cells and between about 1,000,000 cells, more preferably between about 1,000 cells and about 500,000 cells, still more preferably between 10,000 and 100,000 cells even more preferably between about 20,000 cells and about 60,000 cells.

Preferably, the reference level is obtained by measuring the intensity and/or frequency of the interphase nuclear envelope rupture events in the absence of said test compound or any other experimental procedure.

The present invention also concerns, in a third aspect, a recombinant cell stably expressing a cGAS protein or an AIM2 protein, preferably mutated for losing its catalytic or enzymatic function, for instance in E225A and/or D227A for cGAS and F27G for AIM2, fused with at least one detection entity, preferably the protein is a human cGAS protein mutated in E225A and/or D227A or a human AIM2 protein mutated in F27G and is fused with a fluorescent protein or a part thereof, preferably an GFP, EGFP or sfGFP or a part thereof, even more preferably the cell stably express a human cGAS protein mutated in E225A and/or D227A and fused with an EGFP, sfGFP or a part thereof and a FLAG or a human AIM2 protein mutated in F27G and fused with EGFP, sfGFP, or a part thereof.

In a forth aspect, the invention also concerns a transgenic mouse expressing a cGAS protein or an AIM2 protein, preferably mutated for losing its catalytic or enzymatic function, for instance in E225A and/or D227A for cGAS and F27G for AIM2, fused with at least one detection entity, preferably the protein is a human cGAS protein mutated in E225A and/or D227A or a human AIM2 protein mutated in F27G and is fused with a fluorescent protein or a part thereof, preferably an GFP, EGFP or sfGFP or a part thereof, even more preferably the cell stably express a human cGAS protein mutated in E225A and/or D227A and fused with an EGFP, sfGFP, or a part thereof and a FLAG or a human AIM2 protein mutated in F27G and fused with EGFP, sfGFP, or part thereof.

In a fifth aspect, the invention also concerns a kit for screening or identifying a compound capable of increasing or decreasing the intensity and/or the frequency of interphase nuclear membrane rupture events in eukaryotic cells according to the method of the invention and/or for monitoring interphase nuclear membrane rupture events in a eukaryotic cell according to the method of the invention, wherein the kit comprises a recombinant cell as described above and optionally a leaflet providing guidelines to use such a kit.

The invention also concerns, in a sixth aspect, the use of a kit for screening or identifying a compound capable of increasing or decreasing the intensity and/or frequency of interphase nuclear membrane rupture events in eukaryotic cells and/or for monitoring interphase nuclear membrane rupture events in a eukaryotic cell, wherein the kit comprises a recombinant cell as described above and/or a vector suitable for preparing such a cell, preferably a vector suitable for stable transfection and comprising a gene coding for a cGAS protein mutated in E225A and/or D227A or an AIM2 protein mutated in F27G and fused with a fluorescent protein or a part thereof, and eukaryotic cell stable transfection means.

In a seventh aspect, the invention finally concerns the use of a protein fused to a detection entity and having a cytosolic non-nuclear localization in interphase and a non-sequence specific DNA binding activity, a cell expressing such a protein fused to a detection entity or a transgenic animal comprising such a cell for screening or identifying a compound capable of increasing or decreasing the intensity and/or the frequency of interphase nuclear membrane rupture events in eukaryotic cells and/or for monitoring interphase nuclear membrane rupture events in a eukaryotic cell. Preferably, the protein is cGAS or AIM2, more preferably human cGAS (SEQ ID NO: 1) or human AIM2 (SEQ ID NO: 2), even more preferably a cGAS protein mutated in E225A and/or D227A or an AIM2 protein mutated in F27G and fused with at least one detection entity. Preferably, the protein is a human cGAS protein mutated in E225A and/or D227A or an AIM2 protein mutated in F27G and fused with a fluorescent protein or a part thereof, preferably an EGFP, GFP or sfGFP or a part thereof.

Even more preferably, the cell stably express a human cGAS protein mutated in E225A and/or D227A and fused with an EGFP, a sfGFP, or part thereof and a FLAG or an AIM2 protein mutated in F27G and fused with an EGFP, sfGFP, or a part thereof.

BRIEF DESCRIPTION OF THE DRAWINGS

The patent or application file contains at least one drawing executed in color. Copies of this patent or patent application publication, with color drawing(s), will be provided by the Office upon request and payment of the necessary fee.

DETAILED DESCRIPTION OF THE INVENTION

Figure 1:
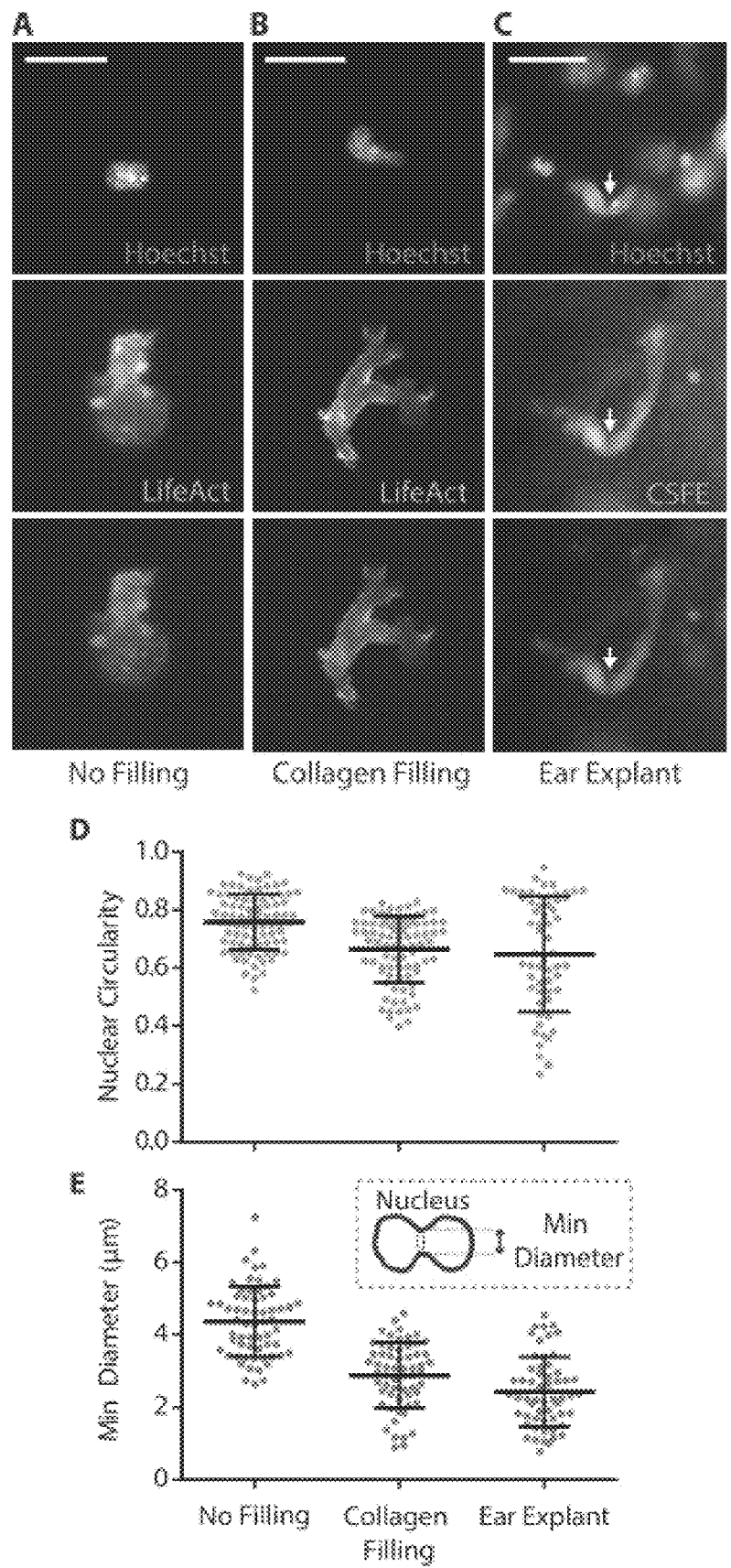
FIG. 1: Dendritic cells deform their nucleus when migrating through confined environments and NLS-EGFP leaks from nucleus to cytoplasm. (A-B) Images of live immature mouse dendritic cells (mDCs) expressing EGFP-LifeAct (green) and DNA stained with Hoechst (blue), migrating between a glass surface and a 5 μm height roof. (A) mDC migrating in 2D confinement without collagen. (B) mDC migrating in 2D confinement with collagen filling, gel of 1.6 mg/ml. (C) images of fixed mDCs prelabeled with CFSE (green) migrating in a mouse ear explant. Post fixation Hoechst staining of nuclei (blue). Arrow points to a deformed nucleus. (D) Nuclear circularity and (E) minimum diameter of Hoechst labeled nuclei quantified for cells migrating in 5 μm height with or without collagen gel or in ear explants (for D and E n>50 cells for each condition, N=2) (F) False color images of mature mDC expressing NLS-EGFP migrating in a collagen gel towards a gradient of the CCL21 chemokine. (G) False color images of mDC expressing NLS-EGFP migrating in an ear explant. Arrows point to strong nuclear constriction. (H) Quantification of nuclear circularity (grey) and NLS-EGFP levels inside nucleus (blue) and in cytoplasm (green) for mDCs migrating in collagen with a CCL21 gradient, during the passage through a confined space. Data were aligned to have time of zero when circularity was at lowest value. n=13 cells. (I) Same quantification for mDCs migrating in ear explants. n=15 cells. Images are maximum projections from 3D confocal stacks acquired every 5 μm over 50 μm. Error bars SD. Scale bars 20 μm.
Figure 1:
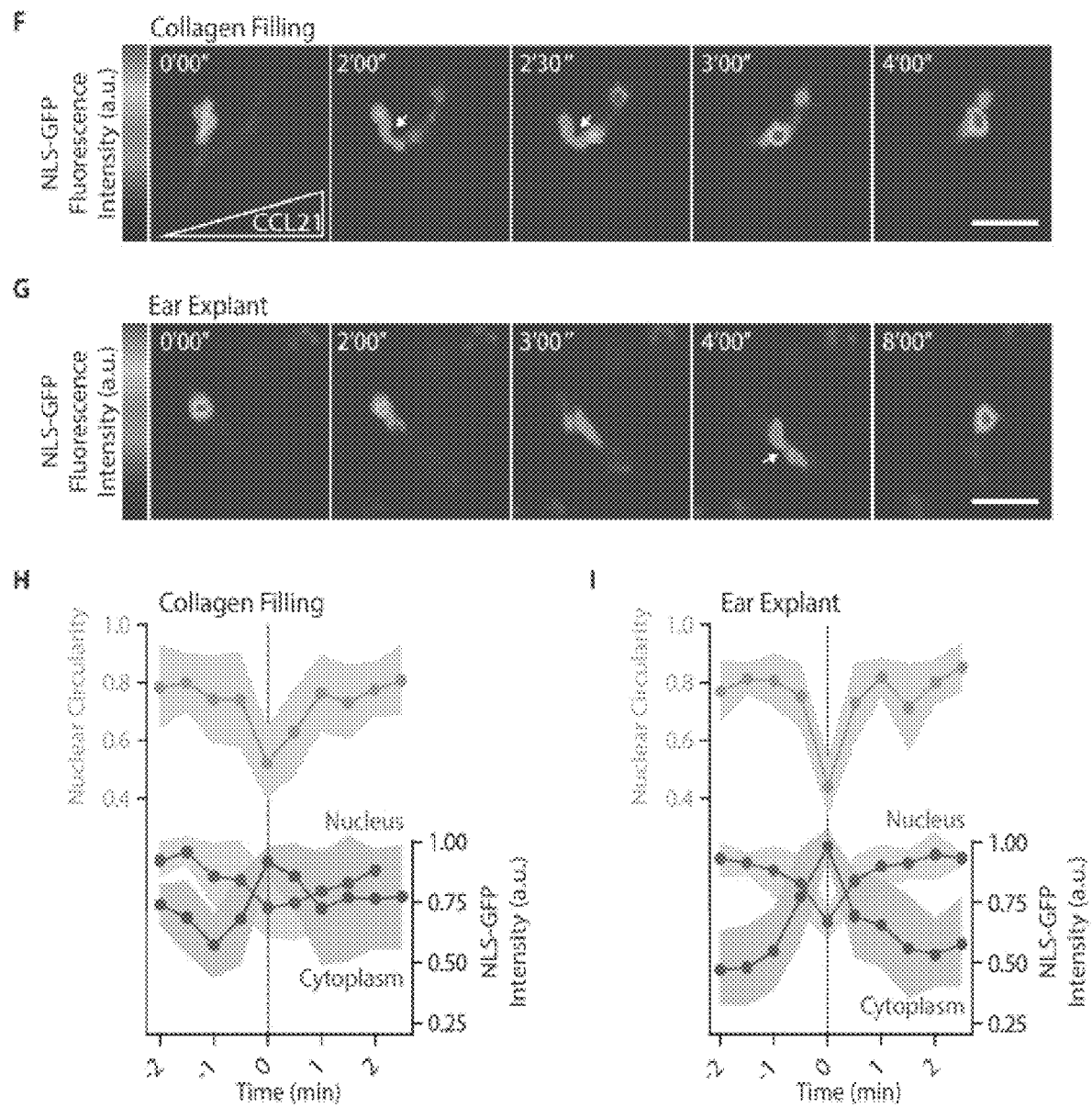

The inventors have discovered a new method that allows to study interphase nuclear envelope rupture events, even hours after the event occurred. This method relies on proteins that have a cytosolic non-nuclear localization in interphase and a non-sequence specific DNA binding activity. Indeed such proteins are normally absent of the nucleus and when they enter it, they bind DNA and stayed in the nucleus. This method can be adapted to the screening of compounds capable of increasing or decreasing the intensity and/or frequency of interphase nuclear envelope rupture events.

Definitions

The term "eukaryotic cell", as used herein, refers to any cell which contains a nucleus and other organelles enclosed within membranes. Especially, in eukaryotic cells, the nucleus, which contains the genetic material, is enclosed by a nuclear envelope. Preferably, the eukaryotic cell is a mammalian cell.

As used herein, the term "nuclear envelope" refers to a structure consisting of two nuclear membranes, the inner and the outer nuclear membranes, an underlying nuclear lamina, and nuclear pore complexes. One of the main function of the nuclear envelope is to segregates the chromatin from the cytoplasm during interphase. The outer nuclear membrane is continuous with the endoplasmic reticulum and is functionally similar to the membranes of the endoplasmic reticulum. In contrast, the inner nuclear membrane carries unique proteins that are specific to the nucleus. The nuclear lamina is directly underlying the double lipid bilayer, it is constitute of an intimately connected meshwork of intermediate filament proteins which provides structural support to the nuclear envelop and has a central role in defining nuclear organization. The nuclear pore complexes are large protein complexes that cross the nuclear envelope. They allow the active transport of molecules across the nuclear envelope. Small particles (especially with a molecular weight under about 40 kDa) are also able to pass through the nuclear pore complexes by passive diffusion.

As used herein, the term "interphase", refers to the phase of the cell cycle that precedes mitosis. The interphase is a metabolic phase of the cell cycle in which the cell obtains nutrients and metabolizes them, grows, reads its DNA, and conducts other normal cell functions. The majority of eukaryotic cells spend most of their time in interphase.

As used herein, the terms "interphase nuclear envelope rupture event", "nuclear envelope rupture event", "nuclear envelope rupture", "interphase nuclear envelope breaching event", "nuclear envelope breaching event", "nuclear envelope breaching" are interchangeable and refer to the rupture of the nuclear envelope of a eukaryotic cell during interphase. This rupture allows proteins to cross the nuclear envelope. Most interphase nuclear envelope rupture events are transient and too small to be directly detected. However, some pathologies like laminopathies, lead to permanent breaches of the nuclear envelope.

The term "nuclear localization signal" (NLS), as used herein, refers to a short amino acid sequence in a protein that targets it for import into the cell nucleus from the cytosol through the nuclear pore complex using nuclear transport.

The term "nuclear export signal" (NES), as used herein, refers to a short amino acid sequence in a protein that targets it for export from the cell nucleus to the cytosol through the nuclear pore complex using nuclear transport.

As used herein, the term "cytoplasm" refers to all the biological material comprises between the plasma membrane and the nuclear envelope of a cell.

As used herein, the term "cytosol" refers to the liquid fraction of the cytoplasm.

The term "cancer" or "tumor", as used herein, refers to the presence of cells possessing characteristics typical of cancer-causing cells, such as uncontrolled proliferation, and/or immortality, and/or metastatic potential, and/or rapid growth and/or proliferation rate, and/or certain characteristic morphological features. This term refers to any type of malignancy (primary or metastases) in any type of subject and any stage of progression.

As used herein, the term "treatment", "treat" or "treating" refers to any act intended to ameliorate the health status of patients such as therapy, prevention, prophylaxis and retardation of the disease.

The terms "quantity," "amount," and "level" are used interchangeably herein and may refer to an absolute quantification of a molecule in a sample, or to a relative quantification of a molecule in a sample, i.e., relative to another value such as relative to a reference value as taught herein.

In the present document, the term «about» refers to a range of values of ±10% of the specified value. For example, «about 40» comprise values of ±10% of 40, i.e. values in the range between 36 and 44. Preferably, the term «about» refers to a range of values of ±5% of the specified value.

In a first aspect, the invention relates to an in vitro method for monitoring interphase nuclear envelope rupture events in a eukaryotic cell comprising:

(a) expressing a protein having a cytosolic non-nuclear localization in interphase and a non-sequence specific DNA binding activity in a eukaryotic cell or providing a eukaryotic cell expressing a protein having a cytosolic non-nuclear localization in interphase and a non-sequence specific DNA binding activity;

(b) measuring the intensity and/or frequency of interphase nuclear envelope rupture events, said interphase nuclear envelope rupture events being characterized by the presence of said protein in the nucleus of said cell; and (c) optionally, comparing the intensity and/or frequency of said interphase nuclear envelope rupture events with a reference level.

Protein Suitable for the Monitoring of Interphase Nuclear Envelope Rupture Events The above mentioned method relies on a protein suitable for the monitoring of interphase nuclear envelope rupture events. To be suitable for the monitoring of interphase nuclear envelope rupture events, said protein must have at least the following properties:

having a cytosolic non-nuclear localization in interphase; and having a DNA binding activity, preferably a non-sequence specific DNA binding activity.

As used herein, "cytosolic non-nuclear localization in interphase" refers to a protein that is, during the interphase and under normal circumstances, exclusively located in the cytosol, and therefore absent of the nucleus, or located in the cytosol and other cytoplasmic compartments but absent of the nucleus.

As used herein, "normal circumstances" refers to the absence of circumstances that would lead to a mislocalization of the protein. Circumstances that would lead to a mislocalization of the protein may be, for example, a breach of the nuclear envelope or any pathological condition or mutation of the protein or of an interaction partner of this protein that would lead to its localization into the nucleus during interphase.

As used herein, the term "exclusively" refers to a protein that is at least at 80%, 85%, 90%, 95%, 99% located in the cytosol and eventually in other cytoplasmic compartments during the interphase, under normal circumstances. In a preferred embodiment, the protein of the invention is 100% located in the cytosol and eventually in other cytoplasmic compartments during the interphase, under normal circumstances.

Other cytoplasmic compartments may be, for example, without limitation, mitochondria compartment, reticulum endoplasmic compartment, Golgi compartment, lysosomal compartment, peroxisomal compartment and other cytoplasmic vesicles.

Preferably, the above mentioned protein is a protein which has naturally a cytosolic non-nuclear localization in interphase. Alternatively, the sequence of a protein can be modified so as it acquires a cytosolic non-nuclear localization in interphase. For example, the sequence of a protein having a non-sequence specific DNA binding activity and a nuclear localization signal (NLS) can be modified in order to suppress or inactivate its NLS, thereby preventing such a protein to be imported from the cytosol into the cell nucleus through nuclear transport. Such a protein can be selected, for example, from the list consisting in histones, the family of HIN200 proteins (hematopoietic interferon-inducible nuclear proteins with a 200-amino-acid repeat), in particular IFI16 (interferon gamma-inducible protein 16) DNA-PK (DNA-dependent protein kinase), DNA damage-binding proteins, in particular DDB1 (damage-specific DNA binding protein 1) or DDB2, DNA damage-sensor proteins, in particular proteins of the MRN complex (Mre11 (meiotic recombination 11, Rad50 (double strand break repair protein) and Nbs1 (nijmegen breakage syndrome 1 protein), RPA (Replication protein A), or Ku70 (ATP-dependent DNA helicase 2 subunit), SOX proteins (SRY (Sex determining Region on Y)-box proteins), DNA helicases, in particular DDX41 (DEAD-box helicase 41), and DAI proteins (DNA dependent activator of IFN-regulatory factors). A variety of genetic manipulation techniques, well known by the skilled person, can be used to modify the genetic sequence of a protein.

As used herein, "DNA binding activity" refers to a protein that is capable to bind any sequence of DNA but is not capable to bind RNA. Preferably, the protein is only capable to bind DNA.

In a preferred embodiment, the DNA binding activity is a non-sequence specific DNA binding activity. As used herein, "non-sequence specific DNA binding activity" refers to a protein that has affinity for DNA whatever the sequence is. In other words, the affinity of this protein for DNA is not specific of a particular DNA sequence.

Preferably, the above mentioned protein is a protein that has naturally a non-sequence specific DNA binding activity. Alternatively, the genetic sequence of a protein can be modified so as it acquires a non-sequence specific DNA binding activity. For example, the non-sequence specific DNA binding domain of a protein can be fused to a protein that has a cytosolic non-nuclear localization in interphase but can't bind DNA. Such a non-sequence specific DNA binding domain can be provided, for example, by a protein selected from the list consisting in histones, the family of HIN200 proteins, in particular IFI16, DNA-PK, DNA damage-binding proteins, in particular DDB1 or DDB2, DNA damage-sensor proteins, in particular proteins of the MRN complex (Mre11, Rad50 and Nbs1), RPA, or Ku70, SOX proteins, DNA helicases, in particular DDX41, and DAI.

In a preferred embodiment, the above mentioned protein has a molecular weight above about 40 kDa, preferably above about 60 kDa. Indeed, proteins with a low molecular weight, especially with a molecular weight under about 40 kDa, are more susceptible to undergo passive diffusion through the nuclear envelope.

In a particular embodiment, the above mentioned protein has a molecular weight above 40 kDa, preferably above 60 kDa. Proteins with a low molecular weight, especially with a molecular weight under 40 kDa, are more susceptible to undergo passive diffusion through the nuclear envelope.

In another preferred embodiment, the above mentioned protein is selected from the group consisting of a cGAS protein and an AIM2 protein, preferably the protein is selected from the group consisting of mammalian cGAS and AIM2 protein, more preferably the protein is selected from the group consisting of mouse, rat and human cGAS and AIM2 proteins, still more preferably the protein is selected from the group consisting of the human cGAS protein (SEQ ID NO: 1) and the human AIM2 protein (SEQ ID NO: 2), even more preferably the protein is the human cGAS protein.

As used herein, the term "human cGAS protein" (UniProt accession number: Q8N884) refers to the product of the human gene CGAS, also named MB21D1 (Mab-21 domain containing 1). As used herein, the terms "cGAS", "Cyclic GMP-AMP synthase", "cGAMP synthase", "2'3'-cGAMP synthase", "Mab-21 domain-containing protein 1" are interchangeable. The human gene CGAS (GeneID: 115004) is located on chromosome 6 in location 6q13. cGAS is a cytosolic DNA sensor involved in immunity response against viruses. cGAS has a nucleotidyltransferase activity, it catalyses the formation of cyclic GMP-AMP from ATP and GTP. cGAS presents two DNA binding domains in positions 173-215 and 384-407.

As used herein, the term "mouse cGAS protein" (UniProt accession number: Q8C6L5) refers to the product of the mouse gene CGAS. The mouse gene CGAS (GeneID: 214763) is located on chromosome 9 in location 9E1.

As used herein, the term "human AIM2 protein" (UniProt accession number: O14862) refers to the product of the human gene AIM2 (Absent In Melanoma 2). As used herein, the terms "AIM2", "Absent in melanoma 2", "interferon-inducible protein AIM2" are interchangeable. The human gene AIM2 (GeneID: 9447) is located on chromosome 1 in location 1q22. AIM2 is involved in innate immune response by recognizing cytosolic double-stranded DNA and inducing caspase-1-activating inflammasome formation in macrophages.

AIM2 has a pyrin domain that allows interaction with PYCARD (PYRIN-PAAD-DAPIN (PYD) and caspase-recruitment domain (CARD) containing domain) and a HIN-200 domain (position 138-337) which is the DNA binding domain.

As used herein, the term "mouse AIM2 protein" (UniProt accession number: Q91VJ1) refers to the product of the mouse gene AIM2 (Absent In Melanoma 2). The mouse gene AIM2 (Gene ID: 383619) is located on chromosome 1 in location 1H3.

In still another preferred embodiment, the above mentioned protein has lost its function, preferably its catalytic or enzymatic function. This can be achieved by mutation of the gene coding for the protein. For example, the function considered here can be its catalytic activity when the protein is an enzyme. The loss of function of the protein must not impair its ability to bind DNA or modify its cellular localization.

Preferably, said protein is a cGAS protein that has lost its nucleotidyltransferase activity. More preferably said protein is a mouse cGAS protein or a human cGAS protein that has lost its nucleotidyltransferase activity. Still more preferably, said protein is a human cGAS protein which presents one or several mutations selected from E225A, D227A, K173A, R176A, K173E, L174N, T211Q, R376I, Y436I, G212A, S213A, K394A, K394E, K407A, K407E, and K411A and has lost its nucleotidyltransferase activity, more preferably said protein is a human cGAS protein which presents a mutation or a combination of mutations selected from an E225A and a D227A mutations, a K173A and a R176A mutations, a K173E mutation, a L174N mutation, a T211Q and a R376I and a Y436I mutations, a G212A and S213A mutations, a K394A mutation, a K394E mutation, a K407A mutation, a K407E mutation, and a K411A mutation, still more preferably said protein is a human cGAS protein which presents an E225A mutation and/or a D227A mutation, even more preferably said protein is a human cGAS protein which presents an E225A mutation and a D227A mutation. E225A mutation and D227A mutations prevent the fixation of magnesium on the catalytic site of cGAS, thereby impairing its nucleotidyltransferase activity.

Alternatively, said protein is an AIM2 protein that has lost its ability to interact with PYCARD. More preferably, said protein is a mouse AIM2 protein or a human AIM2 protein that has lost its ability to interact with PYCARD. Still more preferably, said protein is a human AIM2 protein which presents one or several mutations selected from L10A, L11A, L14A, R24E, F27G, F27L, Y74R, G38E, K39E, D15R, D19A, E20A, E21A, D23A, and has lost its ability to interact with PYCARD, preferably said protein is a human AIM2 protein which presents a F27G mutation. Upon binding to DNA, AIM2 is thought to undergo oligomerization and to associate with PYCARD initiating the recruitment of caspase-1 precursor and processing of interleukin-1 beta and interleukin-18.

In yet another preferred embodiment, the above mentioned protein is fused to one or several detection entities, so as to facilitate its detection. The detection entity may be selected from the group consisting of a tag, an enzyme or a fluorescent protein.

Preferably, the detection entity can be at the N-terminal extremity of the protein or at the C-terminal extremity of the protein. More preferably, the detection entity is at the N-terminal extremity of the protein.

The protein can be fused to a tag. A used herein "tag" refers to protein or peptide sequences genetically grafted onto a recombinant protein and can be detected by specific antibodies. Appropriate tags encompass, without being limited to, FLAG-Tag, His-tag, Strep-tag, Avi-tag, HA-tag (hemagglutinin-tag), S-tag, E-tag, V5-tag, Xpress-tag, VSV-tag, SBP-tag, Softag 1, Softag 2, Softag 3, Isopetag, Spy-tag, calmodulin-tag, Myc-tag, ProtA-tag (proteine A from *Staphylococcus aureus*), Polyglutamate-tag, Tetracysteine-tag, Thioredoxin-tag, NusA-tag, GST-tag (Glutathion-S-Transferase-tag), CBP-tag (Chitin Binding Protein-tag), MBP-tagt (Maltose Binding Protein-tag), and the like. Preferably, the tag is a FLAG-tag.

The protein can also be fused to an enzyme. Appropriate enzymes encompass, without being limited to, horseradish peroxidase, or luciferase. Horseradish peroxidase is an enzyme that catalyzes the conversion of chromogenic substrates (e.g., TMB, DAB, ABTS) into colored products, and that even produces light when acting on chemiluminescent substrates (e.g. Enhanced Chemiluminescence by luminol). Luciferase is a generic term for the class of oxidative enzymes that produce bioluminescence, for example the firefly luciferase (EC 1.13.12.7) from the firefly *Photinus pyralis*.

In a particular embodiment, the protein can be fused to an enzyme capable to modify histones. Histones modifications may then be detected and quantified using a protein capable to interact specifically with these histone modifications, for example a DamID protein.

In another particular embodiment, the protein can also be fused to a part of an enzyme, the other part of this enzyme being constitutively expressed in the nucleus of the cell. In such an embodiment, the presence of the protein in the nucleus allows to functionally recreate the enzyme. For example, the protein of the invention can be fused to a part of lacZ, the other part being constitutively expressed by the nucleus of the cell. The presence of a functional lacZ activity in the cell can be detected and quantified using the substrate of lacZ, X-Gal.

The protein of the invention can also be fused to a fluorescent protein. As used herein "fluorescent protein" refers to proteins that are members of a structurally homologous class of proteins that share the unique property of being self-sufficient to form a visible wavelength chromophore from a sequence of 3 amino acids within their own polypeptide sequence. Fluorescent proteins can be genetically grafted onto a recombinant protein allowing to subsequently visualize the location and dynamics of the protein using fluorescence microscopy. Appropriate fluorescent proteins encompass, without being limited to, GFP (Green Fluorescent Protein), EGFP (Enhanced GFP), sfGFP (super folder GFP), RFP (Red Fluorescent Protein), YFP (Yellow Fluorescent Protein), EYFP (Enhanced YFP), CFP (Cyan Fluorescent Protein), ECFP (Enhanced CFP), BFP (Blue Fluorescent Protein), Tag-BFP, T-Sapphire, mPlum, AQ143, mCherry, sfCherry (super folder Cherry), tdTomato, mStrawberry, J-Red, DsRed-Monomer, mOrange, mOrange2, mKO, mKO2, mCitrine, Venus, YPet, Emerald, Cerulean, CyPet, mTagBFP, mTurquoise, mApple, mKate2, Sirius, Azurite, mTFP1, mUKG1, mAG1, AcGFP1, TagGFP2, mWasabi, EmGFP, TagYFP, Topaz, SYFP2, TagRFP, TagRFP-T, mRuby, mRasperry, mPlum, mNeptune, mAmetrine, mKeima, Sirius, mBlueberry, mHoneydew, AmCyan1, Midori-Ishi Cyan, copGFP, TurboGFP, ZsGreen, TurboYFP, Zs Yellow1, TurboRFP, DsRed2, DsRed-express, DsRed-Express2, DsRed-Max, AsRed2, TurboFP602, RFP611, Katushka, Katushka2, AQ143, PA-GFP, anm2CP (KillerRed), Dronpa, KikG, EosFP, Kaede (red), Kaede (green), dendGFP, EBFP2, mKalama1, Sapphire, SCFP3A, mTurquoise2, monomeric Midoriishi-Cyan, TagCFP, Superfolder GFP, Monomeric Azami Green, mUKG, Clover, mNeonGreen, Citrine, Monomeric Kusabira-Orange, mKOk, mTangerine, mRuby2, HcRed-Tandem, NirFP, TagRFP657, TagBFP, mTagBFP2, IFP1.4, iRFP, mKeima Red, LSS-mKate1, LSS-mKate2, mBeRFP, PA-GFP, PAmCheryl, PATagRFP, KikGR1 (green), KikGR1 (red), PS-CFP2, mEos2 (green), mEos2 (red), mEos3.2 (green), mEos3.2 (red), PSmOrange, Dronpa cFP484.

Preferably, the protein is fused to one detection entity, preferably a fluorescent protein, even more preferably a fluorescent protein selected from the group consisting of GFP, EGFP, sfGFP, RFP, TagBFP, mTagBFP2, tagRFP, tdTomato, mCherry, sfCherry, Venus, TagRFP657. More preferably, the protein is fused to GFP, EGFP or sfGFP. In a most preferred embodiment, the protein is fused to EGFP.

In another particular embodiment, the protein of the invention can also be fused to a part of a fluorescent protein, the other part of this fluorescent protein being constitutively expressed in the nucleus of the cell, in particular by a nucleus protein having a non-sequence specific DNA binding activity, for instance a histone. In such an embodiment, the presence of the protein in the nucleus allows to functionally recreate the fluorescent protein (by functional, is intended fluorescent). For example, the protein of the invention can be fused to a part of a fluorescent protein selected from one of the above described lists, preferably from the group consisting of GFP, EGFP, mCherry, or a sfCherry, more preferably to a part of sfGFP or sfCherry, even more preferably to a part of sfGFP, the other part being constitutively expressed by a protein of the nucleus of the cell, preferably a nucleus protein having a non-sequence specific DNA binding activity, for instance a histone. The presence of a fluorescent sfGFP in the cell can be detected and quantified. Such a system is disclosed in detail in PMID: 26988139, Kamiyama et al, 2016, Nat Commun, 7, 11046 with a system splitting sfGFP in two parts: GFP1-10 and GFP11. For example, one of the part, preferably GFP11, can be fused to the protein of the invention and the other part, preferably GFP1-10, can be fused to a nucleus protein, preferably a nucleus protein having a DNA binding activity, in particular a non-sequence specific DNA binding activity, for instance a histone. This system may decrease the background noise and thereby increase the signal specificity.

In a particular embodiment, the protein is fused to two detection entities, preferably detection entities belonging to two different categories of the above mentioned detection entities, more preferably the protein is fused to a tag and to a fluorescent protein or a part thereof, even more preferably the protein is fused to a FLAG and a GFP, EGFP, sfGFP, or a part thereof.

In another particular embodiment, the protein is a human cGAS protein, preferably presenting an E225A mutation and a D227A mutation, fused with a fluorescent protein or a part thereof, preferably a fluorescent protein selected from the group consisting of GFP, EGFP, sfGFP, RFP, tagRFP or a part thereof, and optionally fused with a FLAG. In a preferred embodiment, the protein is a human cGAS protein presenting an E225A mutation and a D227A mutation and fused with a FLAG and an EGFP, preferably the protein is the EGFP-FLAG-cGAS E225A/D227A protein (SEQ ID NO: 4). Alternatively, the protein is the GFP11-FLAG-cGAS E225A/D227A protein (SEQ ID NO: 14).

In yet another particular embodiment, the protein is a human AIM2 protein, preferably presenting a F27G mutation, fused with a fluorescent protein or a part thereof, preferably a fluorescent protein selected from the group consisting of GFP, EGFP, sfGFP protein, RFP, tagRFP, or a part thereof, and optionally fused with a FLAG. In a preferred embodiment, the protein is a human AIM2 protein presenting an F27G mutation and fused with a FLAG and an EGFP, preferably the protein is the AIM2 F27G-EGFP protein (SEQ ID NO: 11).

Eukaryotic Cell Suitable for Protein Expression

The above mentioned method comprises a step of expressing a protein having a cytosolic non-nuclear localization in interphase and a non-sequence specific DNA binding activity in a eukaryotic cell or providing a eukaryotic cell expressing a protein having a cytosolic non-nuclear localization in interphase and a non-sequence specific DNA binding activity. Preferably, the protein is fused to a detection entity.

In a preferred embodiment of the above mentioned method, a eukaryotic cell expressing a protein having a cytosolic non-nuclear localization in interphase and a non-sequence specific DNA binding activity is provided. Preferably, the protein is fused to a detection entity.

It should be understood that the invention is not limited with respect to any particular eukaryotic cell type and can be applied to all kinds of eukaryotic cells, following common general knowledge. Indeed, the cell expressing a protein of the invention can be any eukaryotic cell, preferably the cell expressing a protein of the invention is a mammal cell, more preferably a human cell. In particular, the cell expressing a protein of the invention can be a cell from a cell line, preferably a human cell-line, a cell from a primary cell culture, preferably a human primary culture, or a cell from a biological sample from a subject.

As used herein, the term "cell line" refers to a permanently established cell culture that will proliferate indefinitely given appropriate fresh medium and space. Examples of cell lines suitable for the expression of the protein of the invention comprise, but are not limited to HeLa, RPE-1, Mutu-DCs, THP-1, L929, leucocyte cell lines, in particular HL60 and Jurkat, brain tumor cell lines, in particular glioblastoma cell lines.

As used herein, the term "primary cell culture" refers to the initial culturing of cells derived directly from the parent tissue. Cells in primary culture have the same karyotype and chromosome number as those in the original tissue. Examples of primary cell cultures suitable for the expression of the protein of the invention comprise, but are not limited to human and mouse dendritic cells, macrophages, BMDC (Bone-Marrow Derived Macrophages), B lymphocytes, T lymphocytes, fibroblasts, neurons, glia cells, and cells from animal models of fast aging, for example Werner or Progeria models.

As used herein, the term "biological sample" refers to any sample containing cells, preferably human cells from the subject. Preferably, the subject is a mammal, more preferably a human. Examples of such biological samples include fluids such as blood, plasma, urine, as well as biopsies, organs, tissues or cell samples. Preferably, the biological sample is a pathological sample, i.e. a sample containing cells distinctive of the pathology of the subject. More preferably, the biological sample is a cancer sample. Examples of cells from a sample from a subject suitable for the expression of the protein of the invention comprise, but are not limited to, cancer cells of a cancer sample, immune cells of a blood sample or of a lymphoid organ sample, fibroblasts of a skin sample, and brain cells from a brain sample.

As above mentioned, the cell provided by the method of the invention express the protein of the invention, preferably fused to a detection entity.

In said provided cell, the protein expression can be constitutive or inducible. Preferably the protein is constitutively expressed by the cell. In particular the gene coding for the protein is placed under the control of a constitutive eukaryotic promoter. Alternatively, the expression of the protein in the cell is inducible. In particular, the gene coding for the protein can be placed under the control of an inducible eukaryotic promoter.

The protein expression can also be transient or stable. Preferably, the protein expression is stable. As used herein, the term "stable expression" refers to cells stably transfected by a gene, i.e. cells in which the transfected gene becomes part of the genome and is therefore replicated. For instance, the sequence coding for the protein, preferably fused to a detection entity, is incorporated into the cell's chromosome.

In another preferred embodiment of the above mentioned method, the method comprises a step of expressing a protein having a cytosolic non-nuclear localization in interphase and a non-sequence specific DNA binding activity in a eukaryotic cell. Preferably, the protein is fused to a detection entity.

A variety of transfection techniques, well known by the skilled person, can be used to express a protein in a cell. In particular, techniques relying on the use of an expression vector in which the gene coding for the protein has been cloned. Such vectors may be selected from plasmids, recombinant viruses like lentiviral vectors, phages, episomes, artificial chromosomes, and the like. Many such vectors are commercially available and may be produced according to recombinant techniques well known per se in the art, such as the methods set forth in manuals such as Sambrook et al., Molecular Cloning (2d ed. Cold Spring Harbor Press 1989), which is hereby incorporated by reference herein in its entirety.

Transfection may be carried out using techniques known per se in the art, such as lipofection, electroporation, calcium phosphate precipitation, etc.

According to the vector choice and/or transfection procedure, the resulting protein expression can be transient or stable. In transient transfections of cells, the vector remains extrachromosomal and disappear after few mitosis. On the opposite, in stable transfections, the gene become inserted in the genome, e.g., through homologous or heterologous recombination, or by any other integration process. Thus, the gene remains expressed by the cells even after several cell divisions.

Preferably, the protein expression is stable. More preferably, the vector used for stable expression of the protein is a lentiviral vector. For instance, a pTRIP lentiviral vector, preferably with a CMV promotor, in particular a pTRIP-CMV-EGFP-FLAG-CGAS lentiviral vector, a pTRIP-CMV-EGFP-FLAG-CGAS E225A/D227A lentiviral vector (SEQ ID NO: 9), a pTRIP-CMV-AIM2 F27G-EGFP lentiviral vector (SEQ ID NO: 12), a pTRIP-CMV-EGFP-tagRFP-CGAS lentiviral vector, or a pTRIP-SFFV-GFP(1-10)-H2B-P2A-GFP11-FLAG-cGAS E225A/D227A lentiviral vector (SEQ ID NO: 17).

Characterization of the Interphase Nuclear Envelope Rupture Events

Interphase nuclear envelope rupture events can be characterized by the intensity and/or the frequency and/or the localization of these events.

Intensity and Frequency of the Interphase Nuclear Envelope Rupture Events

The above mentioned method comprises a step of measuring the intensity and/or frequency of interphase nuclear envelope rupture events, said interphase nuclear envelope rupture events being characterized by the presence of the protein of the invention, preferably fused to a detection entity, in the nucleus of the cell.

As used herein, "measuring" refers to the detection of the interphase nuclear envelope rupture events and to their quantification, allowing to calculate their intensity, as well as their frequency over time.

When an interphase nuclear envelope rupture event occurs, the barrier between the nucleus and the cytosol is temporary abolished and proteins can move freely from one compartment to the other. In particular, the protein of the invention can enter into the nucleus through the breach. When the event ends, most of the proteins are redirected to the compartment which they belong to. Without being bound by the theory, it is thought that because the protein of the invention can bind to DNA of any sequence, the proteins of the invention that have entered the nucleus and will bind DNA and will remain in the nucleus after the breach repair. Thus, detecting the presence of the protein of the invention in the nucleus of a cell allows to detect that there was a nuclear envelope rupture event in this cell. Accordingly, the quantification of the protein of the invention in the nucleus of a cell allows to determine the intensity of the nuclear envelope rupture event.

As used herein, "intensity" may refer to the magnitude of a single interphase nuclear envelope rupture event in a cell. As used herein, "intensity" may also refer to the global magnitude observed in a cell population at a given time. At a cellular level, the intensity of an event is proportional to the size of the breach and to the time that the breach remains open. Indeed, the larger a breach is and the longer it remains open, the more proteins will enter into the nucleus and bind DNA. Thus, the intensity of an event, at a cellular level, is proportional to the number of proteins of the invention that entered into the nucleus of a cell during an interphase nuclear envelope rupture event or that remained into the nucleus after the event. At the level of a population, the global intensity, at a given time, depends also of the fraction of cells in the population that had an interphase nuclear envelope rupture event before measuring, i.e. is proportional either to the proportion of cells that present proteins of the invention in their nucleus or is proportional to the number of proteins of the invention that entered into the nucleus of all the cells that present an interphase nuclear envelope rupture event or that remained in these cells after such events, at a given time.

As used herein, "frequency" refers to the number of interphase nuclear envelope rupture events that a cell, or a population of cell, undergo in a given time by this given time.

In a preferred embodiment, the intensity and/or frequency of the interphase nuclear envelope rupture events are measured on a population of cells. Preferably, the population of cells comprises between about 10 cells and between about 10,000,000 cells, preferably between about 50 cells and between about 1,000,000 cells, more preferably between about 1,000 cells and about 500,000 cells, still more preferably between 10,000 and 100,000 cells.

Prior to this step of measuring, the method may further comprise a step of submitting said cells to an experimental procedure. The experimental procedure may be any experimental procedure that is susceptible to impact the intensity and/or frequency of interphase nuclear envelope rupture events. For example, the experimental procedure may be contacting the cells with a test compound. A test compound is a compound susceptible to modify the intensity and/or frequency of interphase nuclear envelope rupture events. The test compound can be any molecule, in particular an organic molecule, preferably an organic molecule selected from the group consisting in an amino acid, a peptide, a protein, an antibody, a fatty acid, a lipid, a nucleotide, a nucleic acid, a siRNA, a carbohydrate, a derivative thereof, or a combination thereof. The test compound can be any chemical, in particular a chemical from a chemical library. Indeed, the method of the invention is particularly suitable for screening chemical libraries.

In a preferred embodiment, cells are submitted to an experimental procedure at least 10 minutes before measuring the intensity and/or frequency of the interphase nuclear envelope rupture events. Preferably, cells are submitted to an experimental procedure at least 30 minutes before measuring the intensity and/or frequency of the interphase nuclear envelope rupture events, more preferably at least 1 hour before, still more preferably at least 5 hours before, even more preferably at least 10 hours before. In a particular embodiment, cells are submitted to an experimental procedure about a whole interphase before measuring the intensity and/or frequency of the interphase nuclear envelope rupture events.

In another particular embodiment, the intensity and/or frequency of the interphase nuclear envelope rupture events are measured no more than 10 hours after the cells are submitted to an experimental condition, preferably no more than 3 hours, more preferably no more than 1 hour, even more preferably no more than 30 minutes. In a particular embodiment, the intensity and/or frequency of the interphase nuclear envelope rupture events are measured no more than 10 minutes after the cells are submitted to an experimental condition, preferably no more than 1 minute.

Interphase nuclear envelope rupture events are measured by detection of the protein, more particularly by detecting the detection entity when a detection entity is fused to the protein. In a most preferred embodiment, the detection entity is a fluorescent protein, preferably a fluorescent protein selected from the group consisting of GFP, EGFP, sfGFP, RFP, tagRFP, or a fragment thereof, more preferably the fluorescent protein is EGFP.

Interphase nuclear envelope rupture events can be measured in real-time or at an end-point.

In a preferred embodiment, interphase nuclear envelope rupture events are measured in real-time, for example under a microscope, preferably under a fluorescent microscope. Monitoring interphase nuclear rupture events in real-time necessitate conditions suitable for maintaining cells alive. It allows to measure the intensity and the frequency of the events in cells. Preferably, in such embodiments, the protein of the invention is fused to a fluorescent protein. Preferably, the interphase nuclear envelope rupture events are monitored during at least 1 minute, preferably during at least 10 minutes, more preferably during at least one hour, still preferably during at least 3 hours, even more preferably during at least 10 hours and in a most preferred embodiment during about a whole interphase. Preferably the monitoring of the cells start before submitting the cells to an experimental condition. Alternatively, the monitoring of the cells start when the cells are submitted to an experimental procedure or no more than 10 minutes after.

In another preferred embodiment, interphase nuclear envelope rupture events are measured at an end-point. Monitoring interphase nuclear rupture events at an end-point allows to measure the global intensity of events that occurs in the cell before the measurement. Preferably, cells are fixed before the step of measuring. Alternatively, cells are fixed and permeabilized before the step of measuring. As used herein, "cell fixation" refers to the fixation of a population of cells to a slide in a way that preserve the cells from decay, thereby preventing autolysis or putrefaction. Fixation terminates any ongoing biochemical reactions, and may also increase the mechanical strength or stability of the treated cells. As used herein, "cell permeabilization" refers to the process of making the cell membrane and the nuclear envelope permeable, often through the use of surfactants. Permeabilization allows for example antibodies to enter into the nucleus. A variety of fixation and permeabilization techniques, well known by the skilled person, can be used to fix and permeabilize the cells of the invention.

Localization of the Interphase Nuclear Envelope Rupture Events

The above mentioned method may further comprise a step of localizing the interphase nuclear envelope rupture events on the nuclear envelope of a cell, said interphase nuclear envelope rupture event localization being characterized by the localization of the proteins of the invention in the nucleus of the cell during or after the event.

Indeed, when a breach occurs in the nuclear envelop of a cell, the protein of the invention enters into the nucleus through the breach and bind DNA in the vicinity of the breach.

Co-localization of other proteins and cellular structure to the breach might help to identify proteins or cellular structures important for maintenance of nuclear envelope and/or nuclear envelope breach repair.

Analyzing the localization of the protein of the invention in the nucleus may also help to differentiate dead or post-mitotic cells from cells which have undergone an interphase nuclear envelope rupture event. Indeed, in dead or post-mitotic cells, the protein of the invention will be present in the whole nucleus. On the opposite, in cells which have undergone an interphase nuclear envelope rupture event, the protein of the invention will be localized at proximity of the breach.

Detection, Quantification and Localization of the Protein of the Invention in the Nucleus of the Cell The detection, quantification and localization of the protein of the invention in the nucleus of the cell can rely on different techniques, well known from the man skilled in the art, in particular by immunocytochemistry techniques, by direct enzymatic dosage or by direct fluorescence measurement.

In a particular embodiment, the detection, quantification and localization of the protein of the invention in the nucleus of the cell is determined by immunocytochemistry techniques. The detection and quantification of the protein of the invention in the nucleus of the cell by immunocytochemistry may rely on antibodies specific of the protein itself or on antibodies specific of a tag fused to the protein of the invention. Preferably, the protein of the invention is detected and quantified by an antibody specific of tag fused with the protein of the invention. Appropriate tags encompass, without being limited to, FLAG-Tag, His-tag, Strep-tag, Avi-tag, HA-tag (hemagglutinin-tag), S-tag, E-tag, V5-tag, Xpress-tag, VSV-tag, SBP-tag, Softag 1, Softag 2, Softag 3, Isopetag, Spy-tag calmodulin-tag, Myc-tag, ProtA-tag (protein A from *Staphylococcus aureus*), Polyglutamate-tag, Tetracysteine-tag, Thioredoxin-tag, NusA-tag, GST-tag (Gluta-thion-S-Transferase-tag), CBP-tag (Chitin Binding Protein-tag), MBP-tagt (Maltose Bibdibg Protein-tag), and the like. Preferably, the tag is a FLAG-tag. In an alternative embodiment, the protein of the invention is detected and quantified by an antibody specific of the protein of the invention itself, preferably a protein devoid of any tag or other detection entity.

In another particular embodiment, the detection, quantification and localization of the protein of the invention in the nucleus of the cell is determined by direct enzymatic dosage. The detection and quantification of the protein of the invention in the nucleus of the cell by direct enzymatic dosage rely on enzymatic reaction with an enzyme fused to the protein of the invention. Appropriate biochemical enzyme encompass, without being limited to, horseradish peroxidase or luciferase.

In a preferred embodiment, the detection, quantification and localization of the protein of the invention in the nucleus of the cell is determined by direct fluorescence measurement. The detection and quantification of the protein of the invention in the nucleus of the cell by direct fluorescence measurement rely on the fluorescence of a fluorescent protein or a part thereof fused to the protein of the invention. Appropriate fluorescent proteins encompass, without being limited to, GFP (Green Fluorescent Protein), EGFP (Enhanced GFP), sfGFP (super folder GFP), RFP (Red Fluorescent Protein), YFP (Yellow Fluorescent Protein), EYFP (Enhanced YFP), CFP (Cyan Fluorescent Protein), ECFP (Enhanced CFP), BFP (Blue Fluorescent Protein), Tag-BFP, T-Sapphire, mPlum, AQ143, mCherry, sfCherry (super folder Cherry), tdTomato, mStrawberry, J-Red, DsRed-Monomer, mOrange, mOrange2, mKO, mKO2, mCitrine, Venus, YPet, Emerald, Cerulean, CyPet, mTagBFP, mTurquoise, mApple, mKate2, Sirius, Azurite, mTFP1, mUKG1, mAG1, AcGFP1, TagGFP2, mWasabi, EmGFP, TagYFP, Topaz, SYFP2, TagRFP, TagRFP-T, mRuby, mRasperry, mPlum, mNeptune, mAmetrine, mKeima, Sirius, mBlueberry, mHoneydew, AmCyanl, Midori-Ishi Cyan, copGFP, TurboGFP, ZsGreen, TurboYFP, Zs Yellow1, TurboRFP, DsRed2, DsRed-express, DsRed-Express2, DsRed-Max, AsRed2, TurboFP602, RFP611, Katushka, Katushka2, AQ143, PA-GFP, anm2CP (KillerRed), Dronpa, KikG, EosFP, Kaede (red), Kaede (green), dendGFP, EBFP2, mKalama1, Sapphire, SCFP3A, mTurquoise2, monomeric Midoriishi-Cyan, TagCFP, Superfolder GFP, Monomeric Azami Green, mUKG, Clover, mNeonGreen, Citrine, Monomeric Kusabira-Orange, mKOk, mTangerine, mRuby2, HcRed-Tandem, NirFP, TagRFP657, TagBFP, mTagBFP2, IFP1.4, iRFP, mKeima Red, LSS-mKate1, LSS-mKate2, mBeRFP, PA-GFP, PAmChery1, PATagRFP, KikGR1 (green), KikGR1 (red), PS-CFP2, mEos2 (green), mEos2 (red), mEos3.2 (green), mEos3.2 (red), PSmOrange, Dronpa, or a part thereof. Preferably, the fluorescent protein is selected from the group consisting of GFP, EGFP, sfGFP, RFP, TagBFP, mTagBFP2, tagRFP, tdTomato, mCherry, sfCherry, Venus, TagRFP657, or a part thereof. More preferably, the fluorescent protein is selected from the group consisting of GFP, EGFP, sfGFP, or a part thereof. Even more preferably, the fluorescent protein is EGFP, sfGFP, or a part thereof. In a most preferred embodiment, the fluorescent protein is EGFP.

The detection and quantification of the protein of the invention in the nucleus of the cell by direct fluorescence measurement may in particular rely on the fluorescence of a split fluorescent protein, the first part of the split fluorescent protein being fused to the protein of the invention and the second part of the split fluorescent protein being fused to a nuclear protein, preferably a nuclear DNA binding protein, more preferably a nuclear nonspecific DNA binding protein. In a preferred embodiment, the nuclear nonspecific DNA binding protein is selected from the group consisting in lamins, BAF (Barrier-to-Autointegration Factor) proteins, histones, proteins having a NLS (Nuclear Localization Signal) or a NLS itself, more preferably the nuclear nonspecific DNA binding protein is an histone, preferably selected from the group consisting of histones 1, histones 2B, histones 2A, histones 3, and histones 4, more preferably the histone is a histone 2B (cf. Example 4 and also Kamiyama D et al (Nat Commun, 2016; 7:11046) for a general presentation of the technique). Appropriate split fluorescent proteins according to the invention encompass but are not limited to split proteins obtained from the split of fluorescent proteins selected from the above described lists of fluorescent proteins, preferably split fluorescent proteins according to the invention are selected from the couples GFP(1-10) (which encode for the ß-sheets 1-10 of the sfGFP) and GFP11 (which encodes for the 11$^{th}$ ß-sheet of sfGFP), sfCherry1(1-10) and sfCherry11. In a most preferred embodiment, split fluorescent proteins according to the invention are GFP(1-10) and GFP11.

When spatially separated, GFP(1-10) and GFP11 do not fluoresce, it's only when GFP(1-10) and GFP11 are in close proximity that the full sfGFP is reconstituted and fluoresces.

Preferably, GFP(1-10) is fused to a nuclear protein, preferably a nuclear nonspecific DNA binding protein, more preferably a DNA binding protein such as a histone, even more preferably histone 2B, and GFP11 is fused to the protein of the invention. Alternatively, GFP(1-10) is fused to the protein of the invention and GFP11 to a nuclear protein, preferably a nuclear nonspecific DNA binding protein, more preferably a DNA binding protein such as a histone, even more preferably histone 2B.

Comparison to a Reference Level, Analyze of the Results and Treatment

In another embodiment of the above mentioned method, the method may also comprise a step of comparing the frequency and intensity of interphase nuclear envelope rupture events with a reference level.

The reference level may be obtained by measuring the intensity and/or frequency of interphase nuclear envelope rupture events in the absence of said experimental procedure, for example in the absence of submitting the cells to a compound susceptible to modify the intensity and/or frequency of interphase nuclear envelope rupture events.

Preferably, the reference level is measured on cells coming from the same culture batch or from the same sample. More preferably, the reference level is measured on the same cells, before submitting the cells to the experimental procedure. Alternatively, the reference level is measured on cells of the same type and species. In particular, the reference level can be an average of the levels measured with different cells at different times, preferably cells of the same type and species.

In a further embodiment of the above mentioned method, the method further comprises the step of determining whether the experimental procedure, for example submitting or contacting the cells to a test compound, modify the intensity and/or the frequency of the interphase nuclear envelope rupture events. The determination of whether the experimental procedure modify the intensity and/or the frequency of the interphase nuclear envelope rupture events is based on the comparison between the intensity and/or the frequency of the interphase nuclear envelope rupture events of the cells submitted to the experimental procedure with the intensity and/or the frequency of the interphase nuclear envelope rupture events of the reference level. The experimental procedure may increase or decrease the intensity and/or the frequency of the interphase nuclear envelope rupture events.

Preferably, the experimental procedure, for example contacting the cells with a test compound, increases or decreases the intensity and/or the frequency of interphase nuclear membrane rupture events when the intensity and/or the frequency of the interphase nuclear membrane rupture events are increased or decreased compared to a reference level of at least 5%, preferably of at least 10%, more preferably of at least 20%, still preferably of at least 50%, even more preferably of at least 90%.

In a specific embodiment of the above mentioned method, the method is an in vitro method for screening or identifying a compound capable of increasing or decreasing the intensity and/or the frequency of interphase nuclear envelope rupture events in eukaryotic cells comprising:

(a) providing a eukaryotic cell expressing a protein having a cytosolic non-nuclear localization in interphase and a non-sequence specific DNA binding activity; and (b) contacting said cell with a test compound; and (c) measuring the intensity and/or frequency of interphase nuclear envelope rupture events in said cell, said interphase nuclear envelope rupture events being characterized by the presence of said protein in the nucleus of said cell; and
(d) comparing the intensity and/or frequency of said interphase nuclear envelope rupture events with a reference level in the absence of test compound and determining if said compound increases or decreases the intensity and/or the frequency of said interphase nuclear envelope rupture events.

Preferably, the above described method further comprises a step of selecting the compound which increases or decreases the intensity and/or frequency of said interphase nuclear envelope rupture events.

The compounds selected for their ability to increase the intensity and/or frequency of interphase nuclear envelope rupture events are suitable for cancer treatment or induction of innate immunity, in immunotherapy, in adjuvant, in vaccine compositions, in infectious diseases.

The compounds selected for their ability to decreases the intensity and/or frequency of interphase nuclear envelope rupture events are suitable for anti-ageing treatment and in the treatment of auto-immunity disease.

Cell Expressing the Protein of the Invention

In a second aspect, the invention relates to a cell expressing a protein of the invention. Preferably, the cell stably express the protein of the invention.

In a preferred embodiment, the protein is selected from the group consisting of a cGAS protein and an AIM2 protein, preferably the protein is selected from the group consisting of mouse, rat or human cGAS proteins and AIM2 proteins, more preferably the protein is selected from the group consisting of human cGAS protein (SEQ ID NO: 1) and human AIM2 protein (SEQ ID NO: 2), even more preferably the protein is the human cGAS protein.

In another preferred embodiment, the protein has lost its function, preferably its catalytic or enzymatic function. Preferably, the protein is a mouse, rat or human cGAS protein that has lost its nucleotidyltransferase activity, more preferably the protein is a human cGAS protein that has lost its nucleotidyltransferase activity, still more preferably the protein is a human cGAS protein which presents an E225A mutation and/or a D227A mutation, or any other cGAS mutation disclosed previously in the present document, even more preferably the protein is a human cGAS which presents an E225A mutation and a D227A mutation. Alternatively, the protein is a mouse, rat or human AIM2 protein that has lost its ability to interact with PYCARD, preferably the protein is a human AIM2 protein which present a F27G mutation or any other AIM2 mutation disclosed previously in the present document, even more preferably the protein is a human AIM2 protein which present a F27G mutation.

In yet another preferred embodiment, the protein is fused to at least one detection entity. Preferably the detection entity is selected from the group consisting of a tag, an enzyme or a fluorescent protein. More preferably the detection entity is a fluorescent protein or a part thereof. Still more preferably the detection entity is a fluorescent protein selected from the group consisting of EGFP, GFP, sfGFP, RFP, TagBFP, mTagBFP2, tagRFP, tdTomato, mCherry, sfCherry, Venus, TagRFP657, or a part thereof. Even more preferably the protein is fused to the EGFP, GFP, sfGFP or a part thereof. In a most preferred embodiment, the protein is fused to EGFP.

In a particular embodiment, the protein is fused to two detections entity. Preferably, the protein is fused to GFP, EGFP, sfGFP, RFP, tagRFP, or a part thereof and a FLAG. More preferably, the protein is fused to EGFP and a FLAG.

More preferably, the sequence encoding the protein, especially the protein fused to a detection entity, is incorporated into the cell's chromosome.

In a particularly preferred embodiment, the invention relates to a cell stably expressing a cGAS protein, preferably mutated in E225A and/or D227A, fused to at least one detection entity. Preferably, the cGAS protein is a human cGAS protein, preferably mutated in E225A and/or D227A, fused to a fluorescent protein or a part thereof, preferably an EGFP, GFP, sfGFP, RFP, tagRFP, or a part thereof. Even more preferably the cell of the invention stably express a human cGAS protein, preferably mutated in E225A and/or D227A, fused to an EGFP, GFP, sfGFP, RFP, tagRFP, or a part thereof, and a FLAG. In a most preferred embodiment, the cell of the invention stably express a human cGAS protein, preferably mutated in E225A and/or D227A, fused to an EGFP and a FLAG. In another preferred embodiment, the cell of the invention stably express a human cGAS protein mutated in E225A and/or D227A and fused to a GFP11 and a FLAG. Alternatively, the cell of the invention stably express a human cGAS protein fused to an EGFP and a FLAG. Still alternatively, the cell of the invention stably express a human cGAS protein fused to a tagRFP and a FLAG.

In another particularly preferred embodiment, the invention relates to a cell stably expressing an AIM2 protein, preferably mutated in F27G, fused to at least one detection entity. Preferably, the AIM2 protein is a human AIM2 protein, preferably mutated in F27G, fused to a fluorescent protein or a part thereof, preferably an EGFP, GFP, sfGFP, RFP, tagRFP, or a part thereof. Even more preferably the cell of the invention stably express a human AIM2 protein, preferably mutated in F27G, and fused to an EGFP, GFP, sfGFP, RFP, tagRFP, or a part thereof and a FLAG. In a most preferred embodiment, the cell of the invention stably express a human AIM2 protein mutated in F27G and fused to an EGFP and a FLAG.

Transgenic Mouse Expressing the Protein of the Invention

In a third aspect, the invention relates to a transgenic mouse expressing a protein of the invention.

The protein of the invention can be expressed by some or all of the cells of the transgenic mouse. Preferably, at least one cell of the transgenic mouse expresses the protein of the invention. More preferably, all the cell of the mouse express the protein of the invention. The expression of the protein in the cells of the mouse can also be conditional.

In a preferred embodiment, the protein expressed by the transgenic mouse is selected from the group consisting of a cGAS protein and an AIM2 protein, preferably the protein is selected from the group consisting of human cGAS protein (SEQ ID NO: 1) and human AIM2 protein (SEQ ID NO: 2), even more preferably the protein is the human cGAS protein.

In another preferred embodiment, the protein expressed by the transgenic mouse has lost its function, preferably its catalytic or enzymatic function. Preferably, the protein is a human cGAS protein that has lost its nucleotidyltransferase activity, more preferably the protein is a human cGAS which presents an E225A mutation and/or a D227A mutation. Alternatively, the protein is a human AIM2 protein that has lost its ability to interact with PYCARD, more preferably the protein is a human AIM2 which presents an F27G mutation.

In yet another preferred embodiment, the protein expressed by the transgenic mouse is fused to at least one detection entity. Preferably the detection entity is selected from the group consisting of a tag, an enzyme or a fluorescent protein. More preferably the detection entity is a fluorescent protein or a part thereof. Still more preferably the detection entity is a fluorescent protein selected from the group consisting of EGFP, GFP, sfGFP, RFP, TagBFP, mTagBFP2, tagRFP, tdTomato, mCherry, sfCherry, Venus, TagRFP657, or a part thereof. Even more preferably the protein is fused to the EGFP, GFP, sfGFP, or a part thereof.

In a particular embodiment, the protein expressed by the transgenic mouse is fused to two detections entity. Preferably, the protein is fused to EGFP, GFP, sfGFP, RFP, tagRFP, or a part thereof, and FLAG. More preferably, the protein is fused to EGFP and FLAG.

In a particularly preferred embodiment, the invention relates to a transgenic mouse expressing a cGAS protein, preferably mutated in E225A and/or D227A, fused to at least one detection entity. Preferably, the cGAS protein is a human cGAS protein, preferably mutated in E225A and/or D227A, fused to a fluorescent protein or a part thereof, preferably an EGFP, GFP, sfGFP, RFP, tagRFP, or a part thereof. Even more preferably the transgenic mouse of the invention express a human cGAS protein, preferably mutated in E225A and/or D227A, fused to EGFP, GFP, sfGFP, RFP, tagRFP, or a part thereof, and FLAG. In a most preferred embodiment, the transgenic mouse of the invention express a human cGAS protein mutated in E225A and/or D227A and fused to EGFP and a FLAG. In another preferred embodiment, the transgenic mouse of the invention express a human cGAS protein mutated in E225A and/or D227A and fused to GFP11 and a FLAG. Alternatively, the transgenic mouse of the invention express a human cGAS protein fused to EGFP and a FLAG. Still alternatively, the transgenic mouse of the invention express a human cGAS protein fused to tagRFP and a FLAG.

In another particularly preferred embodiment, the invention relates to a transgenic mouse expressing an AIM2 protein, preferably mutated in F27G, fused to at least one detection entity. Preferably, the AIM2 protein is a human AIM2 protein, preferably mutated in F27G, fused to a fluorescent protein or a part thereof, preferably an EGFP, GFP, sfGFP, RFP, tagRFP, or a part thereof. Even more preferably the transgenic mouse of the invention express a human AIM2 protein, preferably mutated in F27G, fused to EGFP, GFP, sfGFP, RFP, tagRFP, or a part thereof and a FLAG. In a most preferred embodiment, the transgenic mouse of the invention express a human AIM2 protein mutated in F27G and fused to EGFP and a FLAG.

Kit and Use of a Kit

The invention also concerns, in a forth aspect, a kit for screening or identifying a compound capable of increasing or decreasing the intensity and/or the frequency of interphase nuclear membrane rupture events in eukaryotic cells and/or for monitoring interphase nuclear membrane rupture events in a eukaryotic cell, wherein the kit comprises a cell expressing a protein of the invention, as previously described. Preferably, as previously described, the cell stably expresses the protein of the invention.

The invention also concerns, in a particular aspect, a kit for screening or identifying a compound capable of increasing or decreasing the intensity and/or the frequency of interphase nuclear membrane rupture events in eukaryotic cells and/or for monitoring interphase nuclear membrane rupture events in a eukaryotic cell, wherein the kit comprises a cell expressing a protein of the invention fused to a first part of a split fluorescent protein and a nuclear protein, preferably a nuclear DNA binding protein, more preferably a nuclear nonspecific DNA binding protein, in particular an histone, preferably histone 2B, fused to a second part of a split fluorescent protein, wherein the split fluorescent protein only fluoresce when the two parts are in close vicinity. Preferably, as previously described, the cell stably expresses the protein of the invention.

The split fluorescent proteins can be selected from the couples GFP(1-10) and GFP11, or sfCherry1(1-10) and sfCherry11.

Preferably, GFP(1-10) is fused to the nuclear protein, preferably a nuclear nonspecific DNA binding protein such as a histone, more preferably histone 2B, and GFP11 is fused to the protein of the invention. Alternatively, GFP(1-10) is fused to the protein of the invention and GFP11 to a nuclear protein, preferably a nuclear nonspecific DNA binding protein such as a histone, more preferably histone 2B.

Optionally, the above mentioned kits further comprises a leaflet providing guidelines to use such kits.

The invention also concerns, in a fifth aspect, the use of a kit for screening or identifying a compound capable of increasing or decreasing the intensity and/or the frequency of interphase nuclear membrane rupture events in eukaryotic cells and/or for monitoring interphase nuclear membrane rupture events in a eukaryotic cell, wherein the kit comprises a recombinant cell as described herein or a vector suitable for preparing such a cell, preferably a vector suitable for stable transfection and comprising a gene coding for a cGAS protein mutated in E225A and/or D227A and fused to a fluorescent protein or a part thereof or an AIM2 protein mutated in F27G and fused to a fluorescent protein or a part thereof, and eukaryotic cell stable transfection means.

In a preferred embodiment, the kit comprises a pTRIP lentiviral vector, preferably with a CMV promotor, in particular a pTRIP-CMV-EGFP-FLAG-CGAS E225A/D227A lentiviral vector (SEQ ID NO: 9).

In another preferred embodiment, the kit comprises a pTRIP lentiviral vector, preferably with a CMV promotor, in particular a pTRIP-CMV-AIM2 F27G-EGFP lentiviral vector (SEQ ID NO: 12).

In a particular embodiment, the kit comprises a pTRIP lentiviral vector, preferably with a SFFV promotor, in particular a pTRIP-SFFV-GFP(1-10)-H2B-P2A-GFP11-FLAG-cGAS E225A/D227A lentiviral vector (SEQ ID NO: 17).

In another particular embodiment, the kit comprises a pTRIP lentiviral vector, preferably with a CMV promotor, in particular a pTRIP-CMV-EGFP-FLAG-CGAS lentiviral vector.

In still another particular embodiment, the kit comprises a pTRIP lentiviral vector, preferably with a CMV promotor, in particular a pTRIP-CMV-tagRFP-FLAG-CGAS lentiviral vector.

In a particular embodiment, the kit comprises a protein of the invention fused to a first part of a split fluorescent protein and a nuclear protein, preferably a nonspecific DNA binding protein such as an histone, more preferably histone 2B, fused to a second part of a split fluorescent protein, wherein the split fluorescent protein only fluoresce when the two parts are in close vicinity.

Use of a Cell, a Transgenic Mouse and a Vector

The invention also concerns, in a sixth aspect, the use of a protein fused to a detection entity and having a cytosolic non-nuclear localization in interphase and a non-sequence specific DNA binding activity, a cell expressing such a protein fused to a detection entity or a transgenic animal comprising such a cell for screening or identifying a compound capable of increasing or decreasing the intensity and/or the frequency of interphase nuclear membrane rupture events in eukaryotic cells and/or for monitoring interphase nuclear membrane rupture events in a eukaryotic cell, wherein said cell expresses a protein of the invention, as previously described. Preferably, the protein fused to a detection entity can be any protein as disclosed above. Preferably, as previously described, the cell stably expresses the protein of the invention.

In a seventh aspect, the invention also concerns the use of a transgenic mouse for screening or identifying a compound capable of increasing or decreasing the intensity and/or the frequency of interphase nuclear membrane rupture events in eukaryotic cells and/or for monitoring interphase nuclear membrane rupture events in a eukaryotic cell, wherein cells of said transgenic mouse express a protein of the invention, as previously described. Preferably, as previously described, the cells of said transgenic mouse stably express the protein of the invention.

In an eighth aspect, the invention also concerns the use of a vector for screening or identifying a compound capable of increasing or decreasing the intensity and/or the frequency of interphase nuclear membrane rupture events in eukaryotic cells and/or for monitoring interphase nuclear membrane rupture events in a eukaryotic cell, wherein said vector is suitable for preparing a recombinant cell expressing a protein of the invention, as previously described.

Preferably, as previously described, the vector is suitable for stable transfection and comprises a gene coding for a cGAS protein, preferably mutated in E225A and/or D227A, fused to a fluorescent protein or a part thereof. In a preferred embodiment, the vector comprises a pTRIP lentiviral vector, preferably with a CMV promotor, in particular a pTRIP-CMV-EGFP-FLAG-CGAS E225A/D227A lentiviral vector (SEQ ID NO: 9). In a particular embodiment, the vector comprises a pTRIP lentiviral vector, preferably with a SFFV promotor, in particular a pTRIP-SFFV-GFP(1-10)-H2B-P2A-GFP11-FLAG-cGAS E225A/D227A lentiviral vector (SEQ ID NO: 17). In another particular embodiment, the vector comprises a pTRIP lentiviral vector, preferably with a CMV promotor, in particular a pTRIP-CMV-EGFP-FLAG-CGAS lentiviral vector. In still another particular embodiment, the vector comprises a pTRIP lentiviral vector, preferably with a CMV promotor, in particular a pTRIP-CMV-tagRFP-FLAG-CGAS lentiviral vector.

Alternatively, as previously described, the vector is suitable for stable transfection and comprises a gene coding for an AIM2 protein mutated in F27G and fused to a fluorescent protein or a part thereof. In a preferred embodiment, the vector comprises a pTRIP lentiviral vector, preferably with a CMV promotor, in particular a pTRIP-CMV-AIM2 F27G-EGFP lentiviral vector (SEQ ID NO: 12).

In a ninth aspect, the invention also concerns the use of a DNA sequence for screening or identifying a compound capable of increasing or decreasing the intensity and/or the frequency of interphase nuclear membrane rupture events in eukaryotic cells and/or for monitoring interphase nuclear membrane rupture events in a eukaryotic cell, wherein said DNA sequence codes for the protein of the invention, as previously described, and is therefore suitable for preparing a recombinant cell expressing a protein of the invention. Preferably, as previously described, said DNA sequence codes for a cGAS protein, preferably mutated in E225A and/or D227A, fused to a fluorescent protein or a part thereof. More preferably said DNA sequence codes for a cGAS protein, preferably mutated in E225A and D227A, fused to EGFP, GFP, sfGFP, RFP, tagRFP, or a part thereof, and FLAG. Even more preferably the DNA sequence is a DNA sequence (SEQ ID NO: 3) coding for the fusion protein EGFP-FLAG-cGAS E225A/D227A (SEQ ID NO: 4). In a particular embodiment, the DNA sequence is a DNA sequence (SEQ ID NO: 13) coding for the fusion protein GFP11-FLAG-cGAS E225A/D227A (SEQ ID NO: 14). In another particular embodiment, the DNA sequence is a DNA sequence coding for the fusion protein EGFP-FLAG-cGAS. In still another particular embodiment, the DNA sequence is a DNA sequence coding for the fusion protein tagRFP-FLAG-cGAS.

Alternatively, as previously described, said DNA sequence codes for an AIM2 protein, preferably mutated in F27G, fused to a fluorescent protein or a part thereof. More preferably said DNA sequence codes for an AIM2 protein, preferably mutated in F27G, fused to EGFP, GFP, sfGFP, RFP, tagRFP, or a part thereof. Even more preferably the DNA sequence is a DNA sequence (SEQ ID NO: 10) coding for the fusion protein AIM2 F27G-EGFP (SEQ ID NO: 11).

The invention also concerns, in a particular aspect, the use of a protein of the invention as previously described, a cell expressing such a protein, a transgenic animal comprising such a cell, a DNA sequence coding for such a protein, or a vector comprising such a DNA sequence, for monitoring the rupture of the nuclear membrane at the beginning of mitosis.

Further aspects and advantages of the present invention will be described in the following examples, which should be regarded as illustrative and not limiting.

EXAMPLES

Material and Methods
Channels Preparation and Cell Loading

Micro-channels were prepared as previously described (Heuzé M L et al, 2011, 769, pp. 415-434). Briefly, polydimethylsiloxane (PDMS) (GE Silicones) was used to prepare 7 µm wide and 5 µm high micro-channels with constrictions of varying lengths and widths from a self-made mold. For HeLa cells, larger channels of 12 µm width and 5 µm height were used because of their larger nuclei. Channels with constrictions were incubated with 15 µg/mL of fibronectin for 30 min then washed with PBS at least 3 times and finally incubated with medium (containing drugs if necessary) for at least 5 hours before adding cells. Not that the height inside constriction varied depending on the width: height was 2 µm for 1.5 µm wide constrictions, 3.5 µm for 2 µm wide constrictions, 4 µm for 3 µm and 4 µm wide constrictions, and 5 µm for 5 µm wide constrictions.
Cell Confinement LifeAct mDCs were plated on glass bottom either with or without 1.6 mg/ml bovine collagen (Filling or No Filling) and then a 5 µm roof of PDMS was placed on top, as previously described (Le Berre M et al, 2012, *Integr Biol* (Camb), 4(11), pp. 1406-1414, Liu Y J et al, 2015, Cell, 160(4), pp. 659-672). Briefly, The side of the 10 mm confining glass slides bearing the PDMS pillars structures was cleaned with isopropanol, well-dried, treated with plasma for 1 min, and modified with 0.5 mg/mL pLL-PEG in 10 mM pH 7.4 HEPES buffer for 1 h at room temperature. For compression to break the nucleus, cells on FluoroDishes (WPI) were squeezed with confining structures of PDMS on glass slides. The confining structure on the glass slide was made in PDMS from molds fabricated by standard photolithography. Briefly, an SU8 2005 photoresist (Microchem) was used to fabricate the mold on a silicon wafer with a regular holes array (diameter: 440 mm, 1 mm spacing), following the manufacturer's protocol. The mold was treated with trimethylchlorosilane (TMCS) for 3 min by evaporation. Afterward, a drop of PDMS mixture (8/1 w/w PDMS A/crosslinker B) was poured into the SU8 mold. Then, a 10 mm standard microscope coverslip, freshly activated for 2 min in a plasma chamber Harrick Plasma, Ithaca, N.Y., USA), was pressed on a PDMS drop to get a residual PDMS layer of minimal thickness. After baking at 95° C. on a hot plate for 15 min, excess PDMS was removed. To peel off the glass slide with PDMS pillars, a drop of isopropanol was poured on the slide. Finally, the slide was gently raised by inserting a razor blade between the slide and the mold, allowing the confining glass slides bound to the PDMS structures to be lifted away. A multi-well plate confiner was designed to confine cells under various conditions in parallel. The modified cover lid of a multi-well plate was used to apply confining slides to cells. In this case, large PDMS pillars were stuck on the cover lid of the multi-well plate to hold confining slides. When the lid was closed, the pillars pushed the confining slides onto the culture substrate and confined the cells. Multiple wells can be processed simultaneously and a larger surface of confining slides can be used. The process of fabrication and handling is as follows: first, large PDMS pillars were fabricated by pouring a PDMS mixture (A:B=35:1) into a custom-made mold, removing bubbles under vacuum, baking overnight at 80° C., and getting the pillars out of the mold with the help of small amount of isopropanol.

Mice

Bone marrow was taken from C57BL/6 mice, to differentiate immature mouse dendritic cells (mDCs), described in (Faure-André G et al, 2008, Science, 322(5908), pp. 1705-1710).

Lifeact-EGFP mice were a kind gift from Michael Sixt lab (IST, Austria), and generated as described (Riedl J et al, 2010, Nat Methods, 7(3), pp. 168-169).

Cells

Monocytes were isolated from peripheral adult human blood as previously described (Lahaye X, Satoh T et al., 2013, Immunity, 39(6), pp. 1132-1142). Monocytes were cultured and differentiated into dendritic cells (hDCs) in RPMI medium with Glutamax, 10% FBS, PenStrep, Gentamicin (50 µg/ml, GIBCO), and HEPES (GIBCO) in the presence of recombinant human GM-CSF (Miltenyi) at 10 ng/ml and IL-4 (Miltenyi) at 50 ng/ml.

Immature mouse bone-marrow derived dendritic cells (mDCs) were cultured 10-12 days in DCs medium (IMDM, FCS (10%), Glutamine (20 mM), pen-strep (100 U/mL) and 2-mercaptonethanol (50 µM)) supplemented with granulocyte-macrophage colony stimulating factor (50 ng/mL)-containing supernatant obtained from transfected J558 cells, as previously described (Faure-André G et al, 2008, Science, 322(5908), pp. 1705-1710). After 4 days of differentiation, all cells are passed to a density of 10-20 million per 120 cm² and repeated again at day 7. Dendritic cells were then experimented with at between days 10 and 12.

HeLa cells were cultured in DMEM Glutamax (Gibco) supplemented with 10% FBS (GE Healthcare) and 1% penicillin and streptavidin (Lonza). The HeLa cells expressing CHMP4B-EGFP at endogenous levels were a kind gift from Antony Hymann's lab (Poser I et al, 2008, Nat Methods, 5(5), pp. 409-415). RPE-1 cells were grown in DMEM-F12 Glutamax medium (Gibco), supplemented with 10% FBS and 1% penicillin and streptavidin (Lonza). RPE-1 cells expressing 53BP1-EGFP were obtained from the lab of Rene Medema (Janssen A et al, 2011, Sciences, 333(6051), pp. 1895-1898). RPE-1 cells expressing NLS-EGFP were obtained from the lab of Martin Hetzer (Hatch E M et al, 2013, Cell, 154(1), pp. 47-60). Stable cell line of HeLa expressing MS2-mCherry-NLS was kindly made in the Buzz Baum lab. HeLa bac cell line expressing endogenous LAP2I3-EGFP and H2B-mCherry were a kind gift from Mark Petronczki lab (Holmer L et al, 2001, Mol Life Sci, 58(12-13), pp. 1741-1747).

Constructs

The plasmids pSIV3+, psPAX2, pCMV-VSV-G and pTRIP-CMV were previously described (Manel N. et al, 2010, Nature, 467(7312), pp. 214-217; Satoh T et al, 2013, Methods Mol Biol, 960, pp. 401-409). Human cGAS WT open reading frame was amplified by PCR from cDNA prepared from monocyte-derived dendritic cells. Human cGAS E225A/D227A mutant was obtained by overlapping PCR mutagenesis. FLAG-cGAS and FLAG-cGAS E225A/D227 were cloned in pTRIP-CMV in frame with EGFP to obtain pTRIP-CMV-EGFP-FLAG-cGAS and pTRIP-CMV-EGFP-FLAG-cGAS E225A/D227A (SEQ ID NO: 9). pTRIP-CMV-tagRFP was generated by substituting the tagRFP sequence (Evrogen) to the EGFP sequence of pTRIP-CMV. pTRIP-CMV-tagRFP-FLAG-cGAS was generated by cloning FLAG-cGAS in frame. pTRIP-SFFV was generated by substitution of the CMV promoter with the SFFV promoter from GAE-SFFV-EGFP-WPRE (Negre D et al, 2000, 7(19), pp. 1613-1623). pTRIP-SFFV-EGFP-NLS (NLS-EGFP hereafter) was generated by introduced the SV40 NLS sequence (PKKKRKVEDP, SEQ ID NO: 5) by overlapping PCR at the N-terminal of EGFP in pTRIP-SFFV.

Human AIM2 was amplified by PCR from cDNA prepared from monocyte-derived dendritic cells. The mutation F27G was introduced by overlapping PCR. AIM2 F27G was cloned in pTRIP-CMV in frame with EGFP to obtain pTRIP-CMV-AIM2 F27G-EGFP (SEQ ID NO: 12). GFP(1-10) sequence was amplified from pcDNA3.1-GFP(1-10) (Addgene #70219). H2B sequence was amplified from pSMPUW-IRES-Neo H2B mRFP. GFP(1-10) was fused in frame to H2B sequence by overlapping PCR to obtain GFP(1-10)-H2B (SEQ ID NO: 15). GFP11 sequence was of synthesis, and was added to FLAG-cGAS E225A/D227A by overlapping PCR to obtain GFP11-FLAG-cGAS E225A/D227A (SEQ ID NO: 13). The P2A sequence was amplified from pTRIP-CMV-P2A and added to GFP11-FLAG-cGAS E225A/D227A to obtain P2A-GFP11-FLAG-cGAS E225A/D227A. GFP(1-10)-H2B and P2A-GFP11-FLAG-cGAS E225A/D227A were fused by overlapping PCR to obtain GFP(1-10)-H2B-P2A-GFP11-FLAG-cGAS E225A/D227A that was cloned in pTRIP-SFFV to obtain the vector pTRIP-SFFV-GFP(1-10)-H2B-P2A-GFP11-FLAG-cGAS E225A/D227A (SEQ ID NO: 17).

For knockdown experiments the vectors were: pLKO.1-Puro-shLacZ (control vector), pLKO.1-Puro-LMNA sh2 (TRCN0000061835), pLKO.1-Puro-LMNB1 sh2 (TRCN0000029270) and were purchased from SIGMA.

Collagen Gel with CCL21 Gradient

Collagen gels were prepared at 1.6 mg/mL of Bovine collagen (Cell Systems, PurCol). DCs were embedded in polymerizing collagen at a concentration of 106 per mL and then placed on glass bottom dishes. After 20 min of collagen gelation at 37° C., medium containing CCL21 at 200 ng/ml was added to equilibrate the gel and generate a gradient across the collagen (Vargas P et al, in press, Nat Cell Biol).

mDC Migration in Mouse Ear Explants

Ears from C57BL/6 mice were excised and a pair of forceps was used to create a hole on the skin. The ventral and dorsal sides of the explant were separated by peeling. The ventral sheet was kept and immunostained with anti-LYVE-1 (R&D Systems) primary antibody to mark the lymphatic vessels. After washing with media, a secondary antibody against rat (Jackson Immunoresearch) was used. The ear sheet was then spread flat in a 6 well plate and a PDMS block with a central hole of diameter 8 mm was placed on top of each explant with the ventral side up. Two hundred thousand DCs expressing NLS-EGFP (see below) were added in 100 µL of culture medium inside the hole. After 1 h of incubation, the ear sheet was washed with culture medium and then placed with the face on which cells were incubating against the bottom glass slide in a Fluoro-Dish. Ear explants were nailed to a block of PDMS to prevent the explant from moving during imaging. Imaging was performed on an inverted confocal microscope, at 37° C. and with 5% CO2, taking z-stacks 50 µm in height with a 5 µm step size.

For quantification of nuclear deformation in ear explants, dendritic cells were prelabeled with CFSE (ThermoScientific) and then allowed to migrate in the ear explants for 5 hours before fixation with paraformaldehyde. Ear explants were then stained for hoechst to label nuclei and imaged with an inverted fluorescent microscope.

Quantifications

Nuclear circularity was quantified by thresholding the Hoechst signal and taking circularity=$4\pi(area/perimeter^2)$. To quantify nuclear leakage of NLS, a small ROI was put in front of the nucleus and the average intensity of this cytoplasm was divided by the average intensity of the nuclear NLS signal before entering the constriction. This takes into account differences in expression levels of NLS-EGFP.

siRNA siRNA 5'-AAA GCA UGG ACG AUC AGG AAG-3' (SEQ ID NO: 6) was used to deplete CHMP3 (Jimenez Science 2014), SMARTpool for SUN1 and SUN2 (Dharmacon, GE LifeSciences), both 5'-GGUG-GUGACGAUCUGGGCU-3' (SEQ ID NO: 7); and 5'-AACUGGACUUCCAGAAGAACAUC-3'(SEQ ID NO: 8) to target LMNA. Non-targeting siRNA (Dharmacon, GE Life Technologies) was used as the control. siRNA was transfected with Lipofectamine RNAiMAX (Invitrogen). Cells were transfected with 120 nM siRNA 48 h and again 24 h before the experiment.

Lentivector Transductions

Transduced hDCs were obtained by infecting monocytes purified from blood with pTRIP-CMV-EGFP-FLAG cGAS E225A/D227A (SEQ ID NO: 9) lentiviral vectors and after 4 to 5 days of differentiation. Transduction of freshly isolated monocytes from blood has been adapted from (Satoh T et al, 2013, Methods Mol Biol, 960, pp. 401-409). 2 million monocytes were seeded in a 6 well plate in 2 ml of medium. 2 ml of fresh virus and 2 ml of SIV-VLP were added to each well in presence of GM-CSF, IL-4 and 8 µg/ml of Protamine (SIGMA). For knockdown experiments, 2 days after transduction, 3 ml of medium were replaced with 3 ml of fresh medium containing GM-CSF, IL-4 and Puromycin (Invivogen) at a final concentration of 2 µg/ml at day 4 or 5 of differentiation cells were resuspended in fresh medium with fresh cytokines and used in assays.

Transduced mDCs were obtained by transduction of murine bone marrow from C57BL/6 mice. 1.8 million bone marrow cells were plated in a 6 well plate at day of purification (day 0) in 2 ml of medium. At day 1.40 ml of fresh pTRIP-SFFV-EGFP-NLS lentivector supernatant were loaded in Ultra-Clear Centrifuge tubes (Beckman Coulter) and ultracentrifuged at 100,000 g in a SW32 rotor (Beckman coulter) for 90 minutes at 4° C. and resuspended in 400 µl of in RPMI medium with Glutamax, 10% FBS, PenStrep, Gentamicin (50 µg/ml, GIBCO). 200 µl of ultracentrifuged virus were used to infect one well of cells in presence of 8 µg/ml of Protamine. Cells were then differentiated for 11 days and split as described above.

For HeLa and RPE-1 cells transduction, 0.5 million cells were plated in a 6 well plate in 1ml and infected with 2 ml of fresh pTRIP-CMV-EGFP-FLAG-cGAS lentivector in presence of 8 µg/ml of Protamine. The cells were then FACS-sorted by gating on the brightest EGFP-positive cells.

Lentiviral Particles Production in 293FT Cells

Lentiviral particles were produced as previously described from 293FT cells (Lahaye X, Satoh T et al., 2013, Immunity, 39(6), pp. 1132-1142). Lentiviral viral particles and viral-like particles were produced by transfecting 1 µg of psPAX2 and 0.4 µg of pCMV-VSV-G together with 1.6 µg of a lentiviral vector plasmid per well of a 6-well plate.

Antibodies and Reagents

For imaging the nucleus, cells were incubated with 200 ng/mL of Hoechst 33342 (Life Technologies) or 34580 (Invitrogen) for 30 minutes at 37° C. and 5% CO2. The following primary antibodies were used for immunoblotting: LmnA/C (H110, Santa Cruz), anti-actin (Millipore), anti-CHMP3 (Santa Cruz), anti-SUN2 (AbCam), and for immunofluorescence; monoclonal mouse Anti-phospho-Histone H2A.X (Ser139) (Millipore), anti Lamin-B1 Nuclear Envelope marker (Abcam), Anti-Nuclear Pore Complex Proteins antibody [Mab414] (Abcam).

For immunofluorescence, secondary antibodies anti-mouse-Alexa488 and anti-Goat-Alexa488 (Jackson ImmunoResearch Laboratories) were used. ATMi (KU-55933, TOCRIS) was used at 10 µM to inhibit DNA repair.

Immunoblotting

Cells were lysed on ice for 45-60 minutes in a buffer containing 100 mM Tris, 150 mM NaCl, 0.5% NP-40, 1:100 of protease inhibitor cocktail (Roche) and 1:100 of phosphatase inhibitor cocktail (Sigma). Thirty micrograms of soluble extracts were loaded onto a 4-20% TGX gradient gel (BioRad) and transferred onto a Trans-Blot Turbo PVDF/Nitrocellulose membrane (BioRad). The membrane was blocked, incubated with the appropriate antibodies and revealed with SuperSignal West Dura substrate (Thermo Scientific).

Photodamage and Time-Lapse Imaging

Cells were cultured in Leibovitz's L-15 CO2-independent medium (GIBCO) with 10% FBS during the acquisition. Spinning-disc confocal microscopy was carried out with a Yokogawa CSU-X1 spinning-disc head on a Nikon Eclipse Ti inverted microscope equipped with an EMCCD camera (Evolve, Photometrics), a NanoScanZ piezo focusing stage (Prior Scientific) and a motorized scanning stage (Marzhauser) and a Nikon S Fluor 100x/1.3 NA objective. The UV-laser damage experiments were performed with a pulsed 355 nm ultraviolet laser (Roper Scientific) driven by iLas software. This microscope was operated with Metamorph and images were processed with FIJI.

Example 1

The nuclear envelope (NE) functions as a barrier to segregate the chromatin from the cytoplasm, and is considered to remain intact during interphase. Only under pathological circumstances is the NE thought to open in non-mitotic cells. It can bud during viral infection (1) or be completely breached in laminopathies, pathologies associated to mutations in genes coding for nuclear lamina proteins, especially in LMN A/C and in cancer cells. Many cancer cells have been found to express lower levels of LMN A/C, which correlates with a higher degree of metastatic potential, potentially because it makes their nuclei more deformable, and thus allow them to migrate through narrower pores and to invade tissues. Importantly, a recent study demonstrated that complete removal of this protein leads to an increase in cell death during transmigration, and eventually reduces the extent of metastasis. The cause of this cell death remains unknown. Similarly to cancer cells, several types of immune cells have also been reported to express lower levels of, or even no LMNA/C. These cells, such as neutrophils, lymphocytes or dendritic cells, also have the capacity to migrate through dense tissues, between other cells, through walls of lymph and blood vessels and through interstitial space in tissues, and their response to pathogens is tightly associated with their migratory capacities. This raises the question of whether specific survival mechanisms exist that allow highly migratory and deformable cells to survive their journey through tissues, despite a large degree of nuclear deformation.

To assess the degree of nuclear deformation associated with cell migration, the inventors compared bone-marrow-derived mouse dendritic cells (mDCs), migrating between 2 surfaces spaced 5 µm apart either without (FIG. 1A) or with collagen filling (FIG. 1B), as well as cells migrating through mice ear explants (FIG. 1C). The inventors found that nuclei were more deformed when cells were migrating through collagen or ear explants: nuclei were more irregularly shaped (FIG. 1D) and the minimum diameter of the nucleus was reduced (FIG. 1E). This reflected a high occurrence of pinched or dumbbell-shaped nuclei already reported as being typical of cancer cells crossing small pores when migrating through collagen gels and tissues. The average minimal nuclear diameter was close to 2 µm, which corresponds to the measured size of the portal dendritic cells use to enter lymphatic vessels. These data suggest that dendritic cells frequently deform their nucleus during steady state migration through physiological environments.

To monitor potential defects in nuclear integrity, the inventors recorded mDCs expressing NLS-EGFP and matured with LPS to express CCR7. They followed cells migrating either through a collagen gel (FIG. 1F), in the presence of a gradient of the CCL21 chemokine, or in an ear explant (FIG. 1G). Most cells displayed, as expected, a bright EGFP signal in the nucleus and a weak cytoplasmic background, suggesting that the nucleo-cytoplasmic barrier was intact. The inventors then specifically investigated cells undergoing strong nuclear deformations and observed a decrease in the NLS-EGFP nuclear signal, which correlated with a decrease in nuclear circularity (FIG. 1H, I note that to compare different cells, time zero was set at minimal circularity for all cells). This was also accompanied by an increase of the NLS-EGFP cytoplasmic signal. Interestingly, the recovery of the nuclear signal occurred with a slight delay after the nucleus had regained its circularity. Taken together, these observations suggest that upon strong nuclear deformation, the nucleo-cytoplasmic barrier was transiently abrogated and then restored, likely corresponding to an opening of the nuclear envelope.

Because collagen gels and ear explants offer poor control over the precise degree of nuclear deformation and do not easily allow for high resolution imaging, the inventors used a migration assay consisting of micro-channels with constrictions of various sizes (FIG. 5A,B), matching the range of sizes observed in vivo for nuclear deformation (FIG. 1E). Migrating cells could spontaneously pass constrictions as small as 1.5 µm. The inventors used cells expressing NLS-EGFP to assess what level of deformation could induce nucleo-cytoplasmic leakage. To extend the findings to human cells and to other cell types, the inventors investigated monocyte-derived human DCs (hDCs) (FIG. 2A, B) as well as cultured cancer cells (HeLa, FIG. 2C, 5C), and normal cultured immortalized cells (RPE1, FIG. 5D). For 2-µm-wide constrictions, the inventors observed that, while the nucleus was crossing the constriction, the NLS-EGFP nuclear signal strongly decreased and the cytoplasmic signal increased (compare time 00:09 and 00:12 for hDCs in FIG. 2A). When the nucleus exited the constriction, the nuclear signal was restored. Deformation of the nucleus through a well-defined artificial constriction thus induced a relocalization of NLS-EGFP (FIG. 2B) similar to what the inventors observed for mDCs in gels and in ear explants (FIG. 1F-I). Cytoplasmic NLS-EGFP signal remained high as long as the nucleus was engaged within the constriction, independently of cell speed (nuclear passage lasted only about 10 min for hDCs but up to several hours for HeLa cells).

Figure 2:
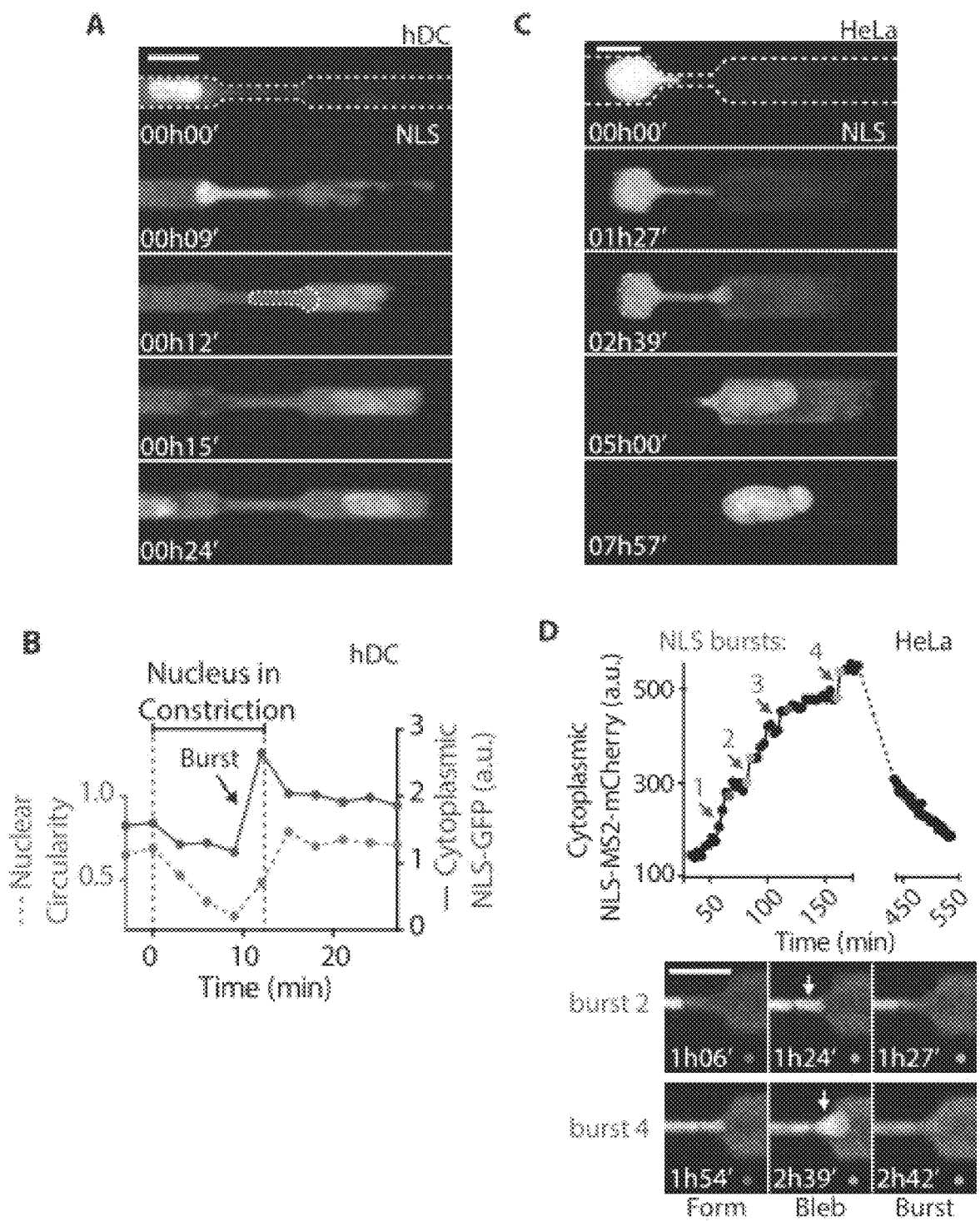
FIG. 2: Nuclear constriction during migration induces leakage of NLS-EGFP and entry of cytoplasmic cGAS into the nucleus. (A) Human Dendritic Cell (hDC) expressing NLS-EGFP migrating through a 7 μm wide channel with a constriction of 15 μm in length and 2 μm in width (L=15 μm, w=2 μm, see methods for constriction height). Nucleus (stained with Hoechst, staining not shown) is outlined in dashed white line when undiscernible from cytoplasmic NLS-EGFP. (B) Quantification of cytoplasmic NLS-EGFP for the hDC shown in (A) with the nuclear circularity determined from Hoechst labeling. (C) HeLa cell expressing NLS-MS2-mCherry passing through a 12 μm wide channel with a constriction 15 μm long and 2 μm wide. (D) Quantification of NLS leakage into the cytoplasm for the HeLa cell shown in C. 4 burst events are indicated on the graph, with events 2 and 4 depicted in the images below the graph with colored dots to indicate location in time on the graph. (E) Quantification of NLS-EGFP localization in cells passing through constrictions 20 μm long with different widths (1.5 μm red, 3 μm blue, 5 μm green, grey curve for cells which did not show any leakage, for all constriction sizes). Data for all cells were aligned with each other so that front end of the nucleus was at the end of the 20 μm long constriction, indicated by the dashed line. To account for differences in expression levels of NLS-EGFP between cells, the average intensity of NLS-EGFP in the cytoplasm was normalized by the initial nuclear intensity of NLS-EGFP before entering the constriction. (F) Percent of cells which survive after passing a constriction (no death observed until the end of the overnight movie, determined from DNA labeling). Constrictions are L=15 μm, w=2 μm. (G) Fraction of cells which open their nucleus during passage through a constriction (L=15 μm, w=2 μm) determined from either NLS-EGFP exit or EGFP-FLAG-cGAS E225A/D227A (SEQ ID NO: 4) entry for hDC cells or EGFP-FLAG-cGAS entry across nucleus for Hela and RPE1 cells (for F and G, n>40 cells and N=3 for RPE1 and hDCs, n=20 and N=2 for HeLa) (H) hDC expressing EGFP-FLAG-cGAS E225A/D227A (DNA-BP) (green) and DNA marked with Hoechst (red) migrating through a constriction. Arrow indicates the precise point along the constriction where cytoplasmic EGFP-FLAG-cGAS E225A/D227A first binds to the DNA at the nuclear tip. (I) Fraction of hDCs in which EGFP-FLAG-cGAS E225A/D227A (DNA-BP) enters the nucleus during passage of constrictions of 15 μm in length for different widths. (J) Location along the constriction where the EGFP-FLAG-cGAS E225A/D227A ((DNA-BP) first enters the nucleus in hDCs. (K) HeLa cell expressing EGFP-FLAG-cGAS (DNA-BP) (green) and H2B-mCherry (red). After the nucleus completely passed the constriction the EGFP-FLAG-cGAS (DNA-BP) remained bound to the region of DNA inside the nucleus. (L) Plot of total intensity of EGFP-FLAG-cGAS (DNA-BP) which has entered the nucleus in the HeLa cell depicted in (K) while passing the constriction. Green arrows indicate sequential events of entry of EGFP-FLAG-cGAS (DNA-BP). Scale bars 10 μm. Experiments with hDCs take into account 3 separate human donors.
Figure 2:
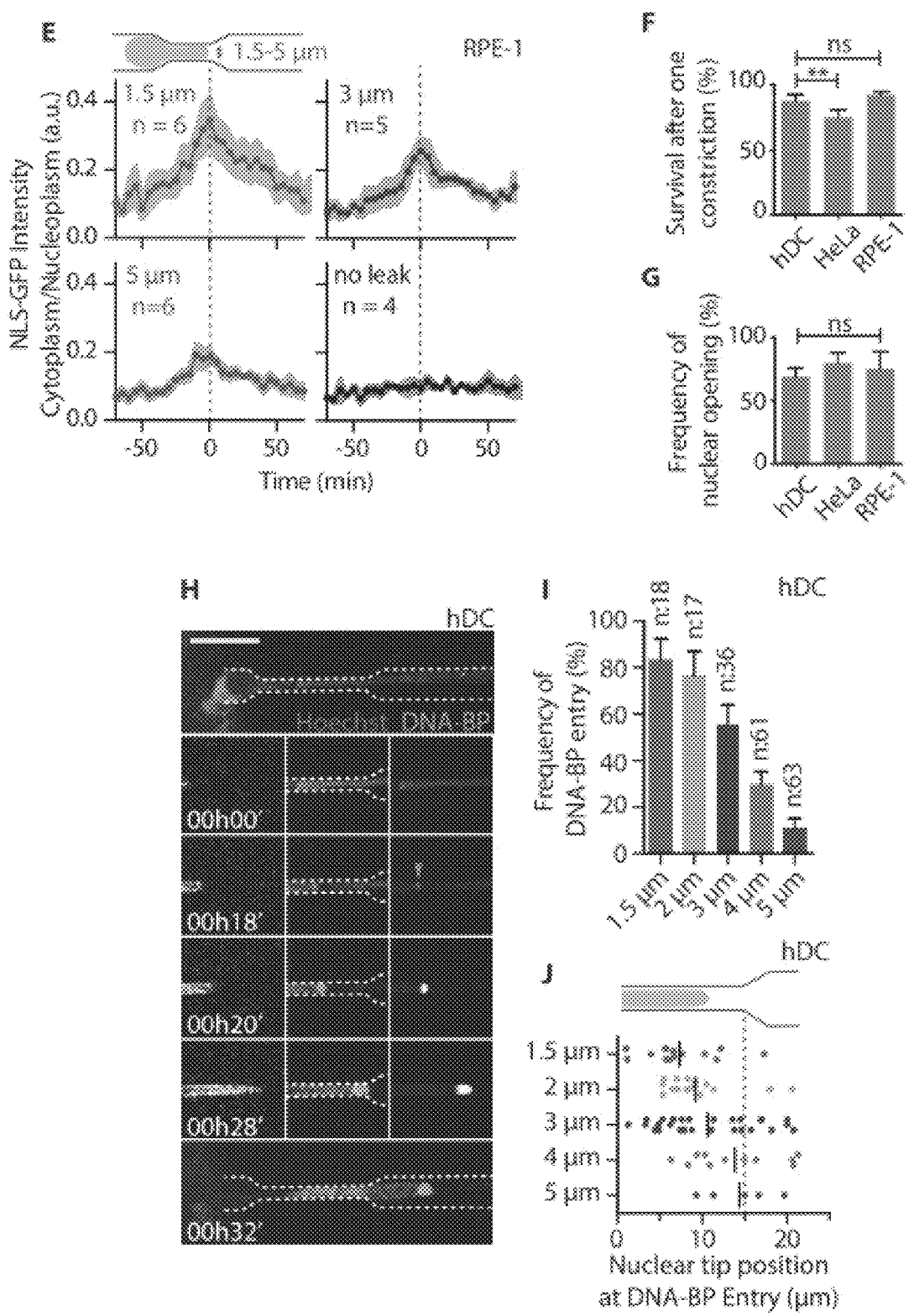
Figure 2:
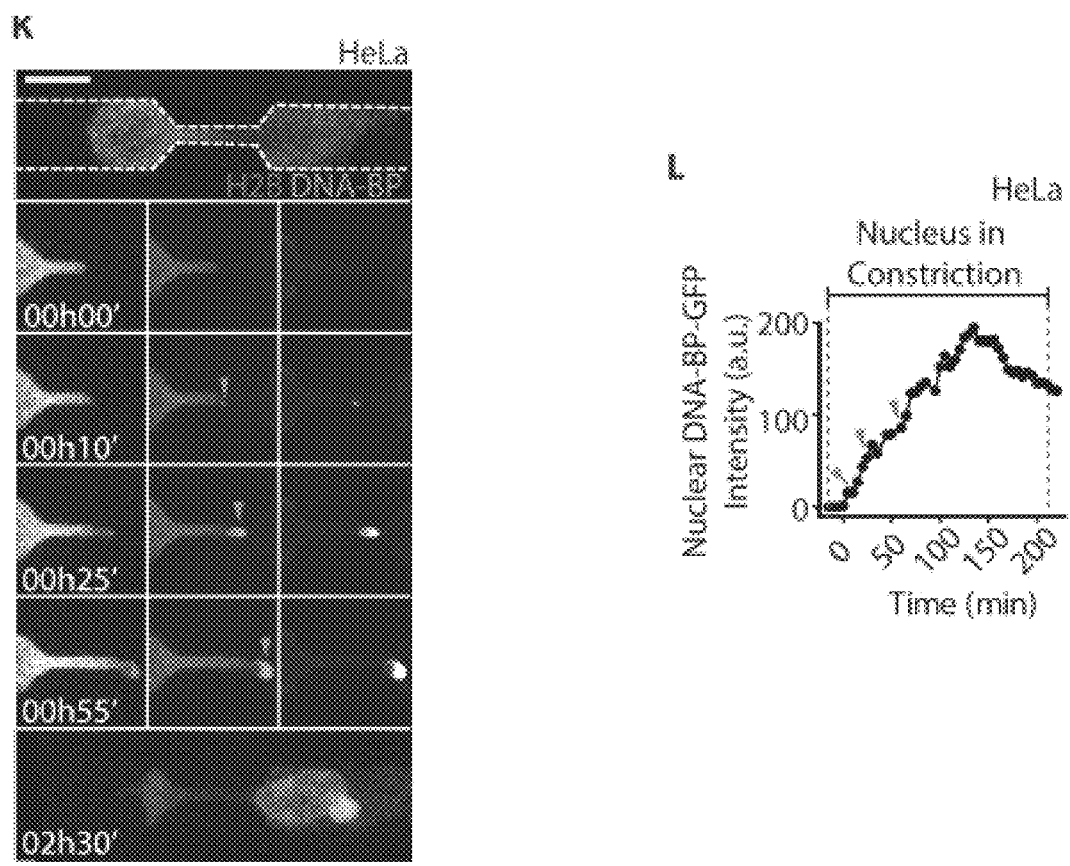

Interestingly, the slow passage of HeLa cells allowed us to observe several individual leakage events (bursts in FIG. 2D), which corresponded to the formation and rapid disappearance of bleb-like structures at the tip of the passing nucleus (FIG. 2D zoomed images at the bottom). This would suggest a mechanism by which deformation of the passing nucleus generates increased internal pressure, leading to the formation of nuclear membrane blebs that eventually rupture and cause NLS-EGFP to leak out of the nucleus. This is followed by a resealing process, until the next bleb forms and ruptures. This is reminiscent of previous observations of non-migrating cells when they are actively compressed.

Consistently, the amount of cytoplasmic leakage of NLS-EGFP increased when the constriction size was narrower (FIG. 2E). The EGFP signal accumulated again in the nucleus after the nucleus had passed the constriction, suggesting that the NE resealed. Passing constrictions had only a marginal effect on cell survival (FIG. 2F, 5E), despite a high frequency of nuclear rupture events, similar for all cell types studied (FIG. 2G). Together, these results suggest that migrating cells, when deforming their nucleus, display a high survival rate despite frequent opening of their nuclear envelopes, and that this survival is likely due to efficient NE resealing.

Figure 5:
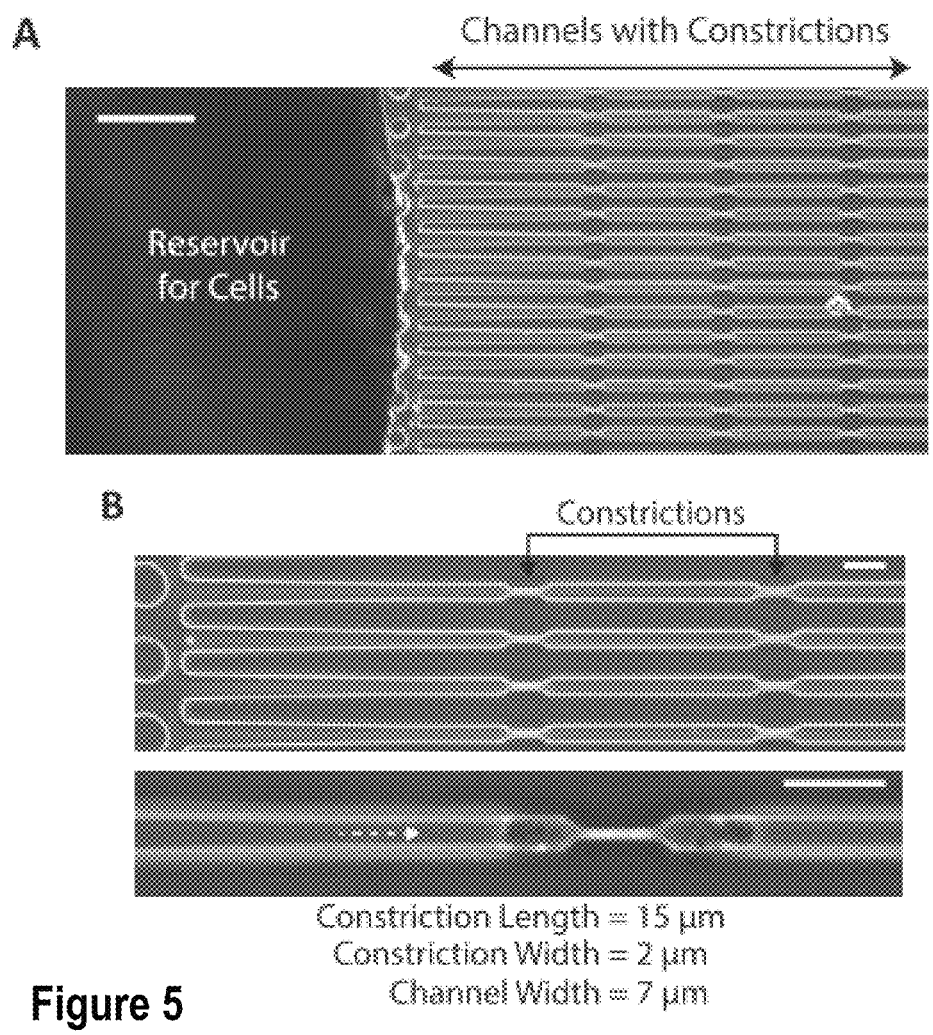
FIG. 5: (A) Low magnification image of the reservoir where cells were added and allowed to migrate spontaneously into channels. The channel contains successive constrictions. Scale bar is 100 µm. (B) Higher magnification image of channels with constrictions. Below: Phase contrast image of an mDC migrating through a constriction. Scale bar 20 µm. (C) HeLa cell expressing NLS-MS2-mCherry slowly passing a constriction. False color was applied to better show the increase in NLS-MS2-mCherry in the cytoplasm. (D) RPE-1 cell expressing NLS-EGFP migrating through a constriction of 15 µm length and 1.5 µm width. (E) Viability of cells after passing a constriction for constrictions of 15 µm in length and 4 µm in width (less nuclear constriction than FIG. 2F). n=10 for HeLa, n>20 for hDCs and RPE1, N=2 (F) hDC expressing EGFP-FLAG-cGAS E225A/D227A (DNA-BP) (green) and DNA labeled with Hoechst (red). The cell was compressed with a PDMS roof until nuclear blebs were observed (white arrow). The bleb then bursted and EGFP-FLAG-cGAS E225A/D227A (DNA-BP) bound to DNA along the nuclear edge locally where the bleb originated. Scale bars 10 µm. (G) Frequency of EGFP-FLAG-cGAS E225A/D227A (DNA-BP) entry in the nucleus for varying constriction dimensions, for hDCs from 4 separate donors. (H) Position along the constriction at which EGFP-FLAG-cGAS E225A/D227A (DNA-BP) entered the nucleus for various constriction dimensions. Dashed lines indicate the exiting end of the constriction, thus points after the dashed line signify breaks occurring after the front nuclear tip had passed the constriction. For G and H, n>25 for each condition, N=3 (I) Location of EGFP-FLAG-cGAS (DNA-BP) entry in the nucleus for HeLa cells expressing EGFP-FLAG-cGAS (DNA-BP) migrating through constrictions, L=15 µm, w=2 µm. n=19, N=2 (J) U2OS cell expressing LaminA-EGFP migrating through a constriction. The Lamina ruptures and reforms constantly at the tip of the nucleus. (K) mDCs with nuclei inside constrictions fixed and stained for nuclear pore complex proteins (green) and DNA with Hoechst (blue). The left cell was also stained for LaminB (red). The tip of the nucleus was devoid of nuclear pores or LaminB staining (white arrows). Cells are representative of more than 10 cells observed. Scale bars are 10 µm. (L-N) Three representative examples of HeLa BAC cells expressing LAP2β-EGFP and H2B-mCherry migrating through constrictions (L=15 µm, w=2 µm). Scale bars are 10 µm.
Figure 5:
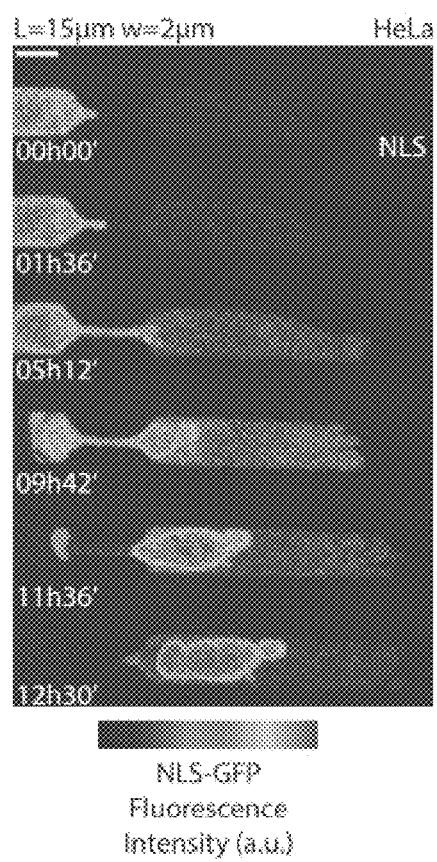
Figure 5:
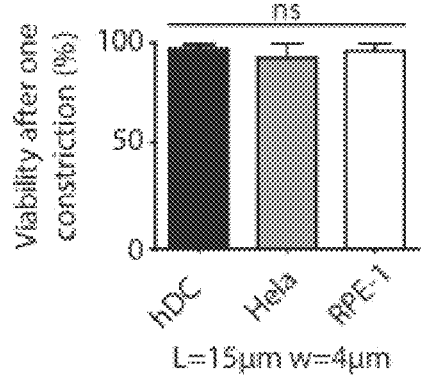
Figure 5:
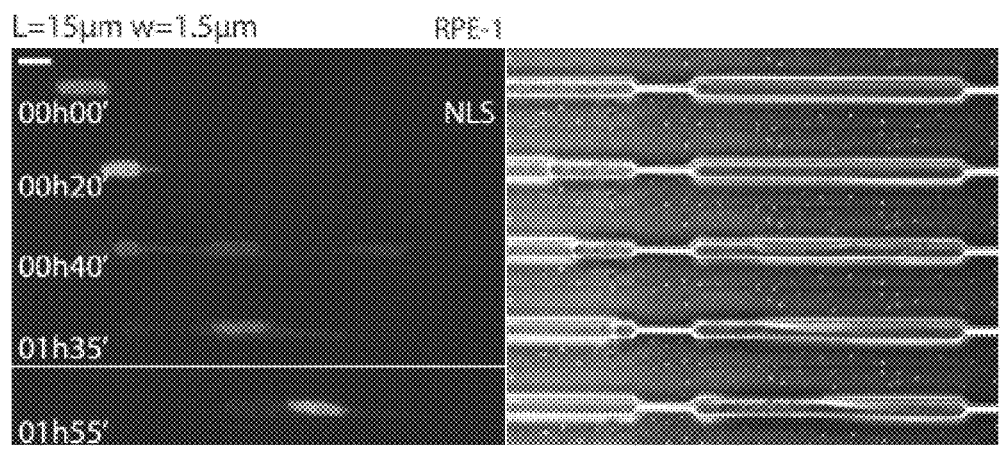
Figure 5:
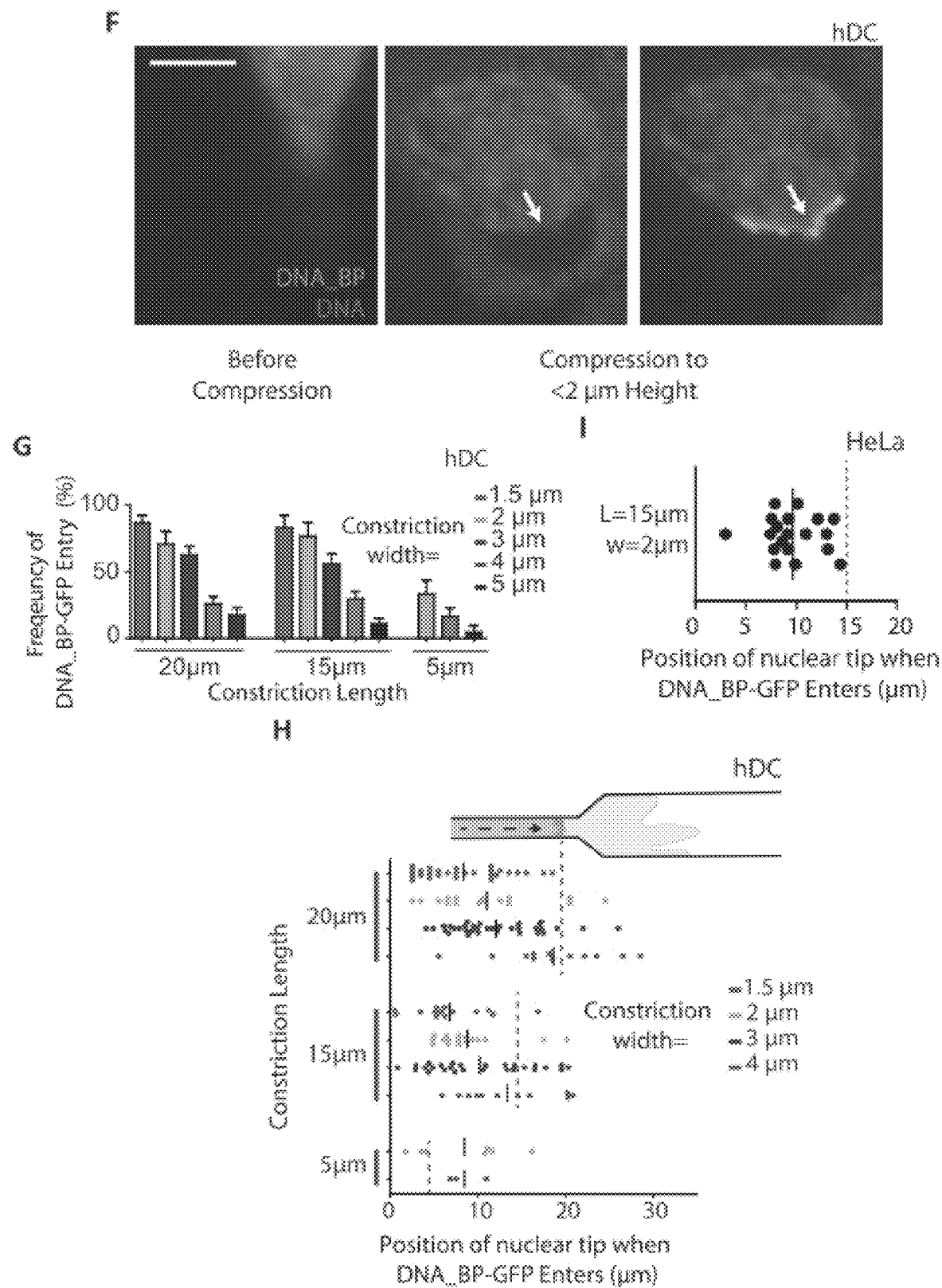
Figure 5:
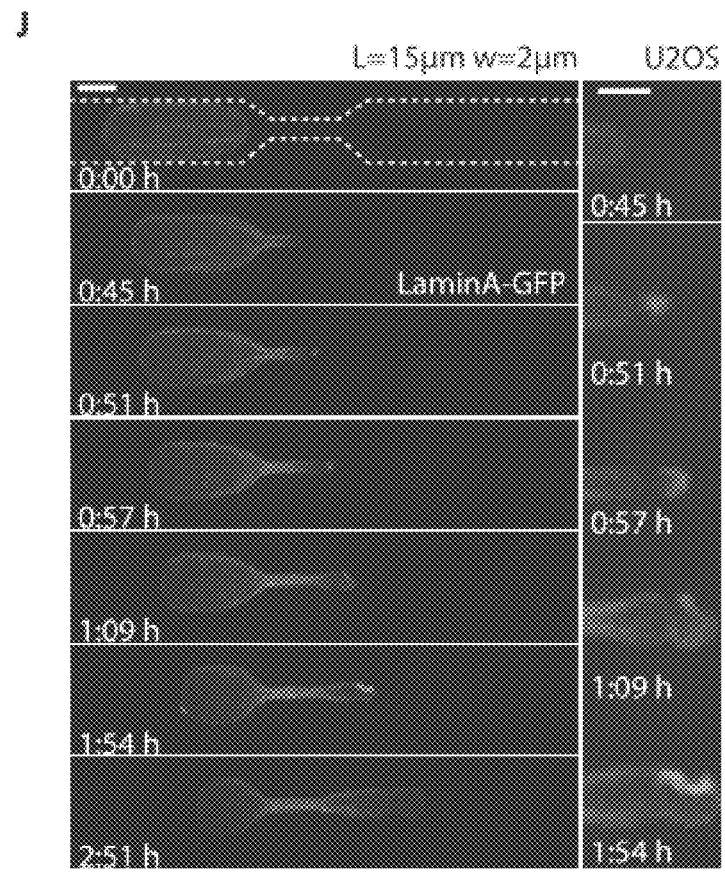
Figure 5:
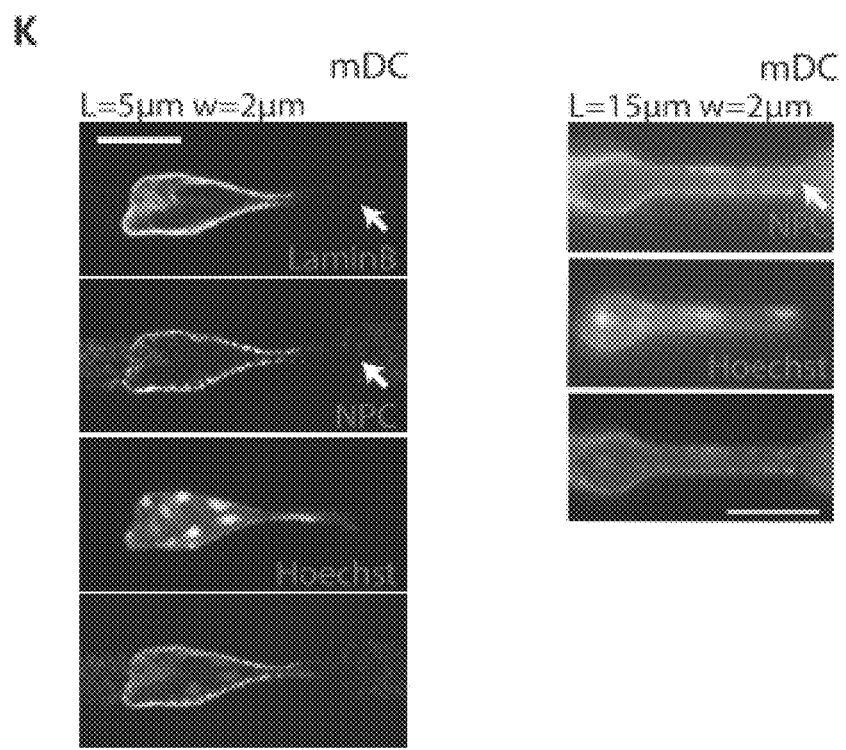
Figure 5:
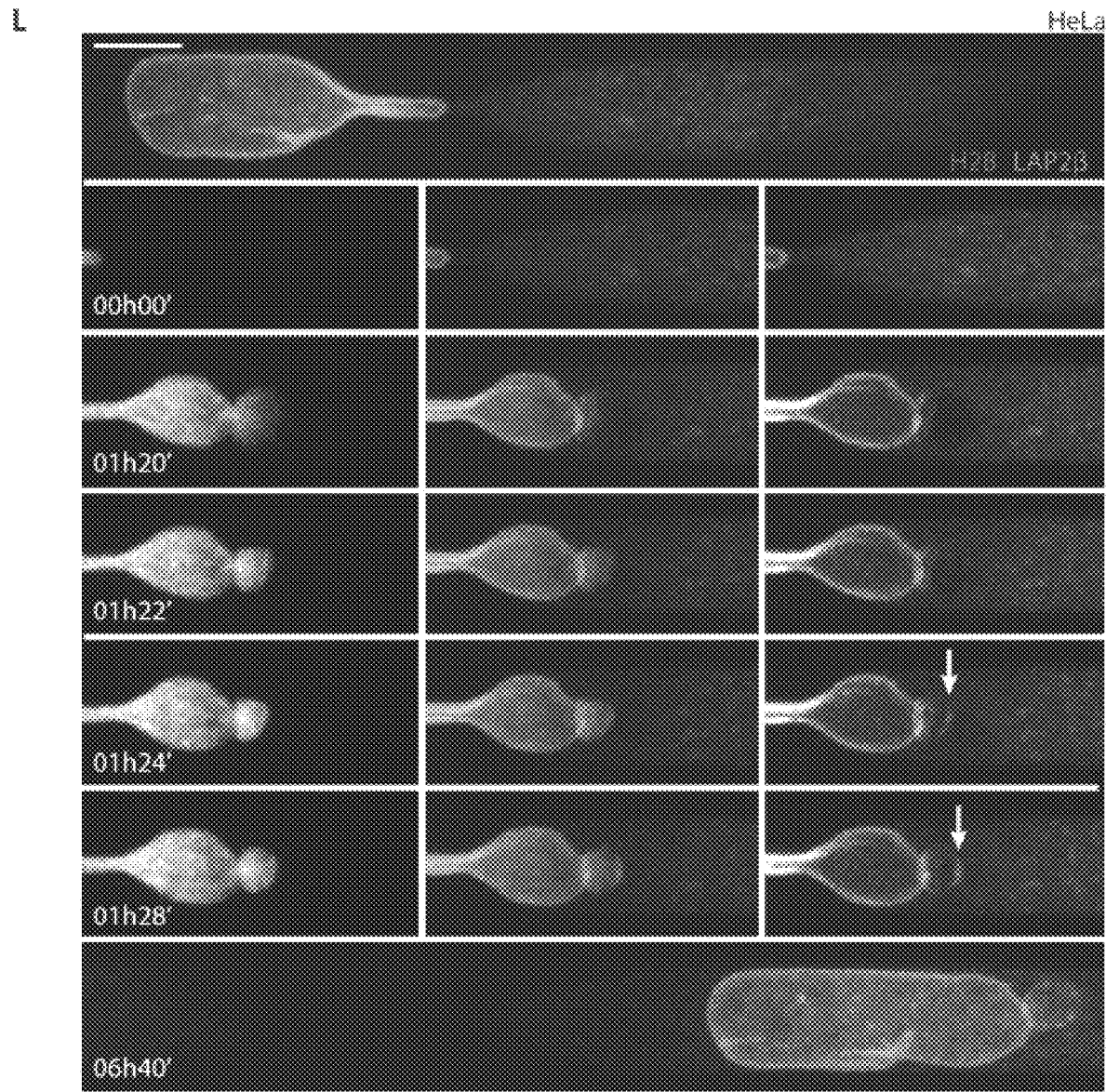
Figure 5:
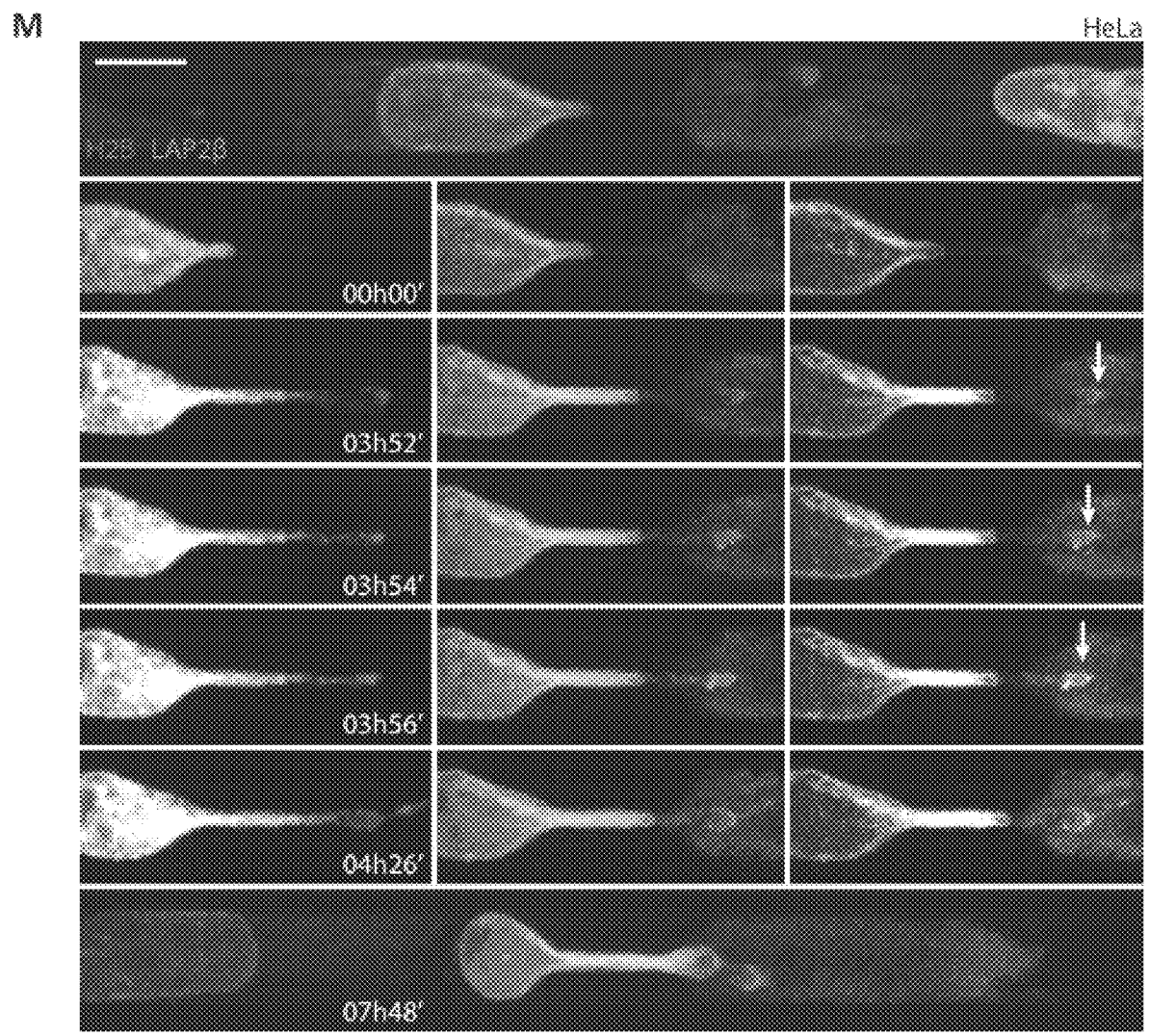
Figure 5:
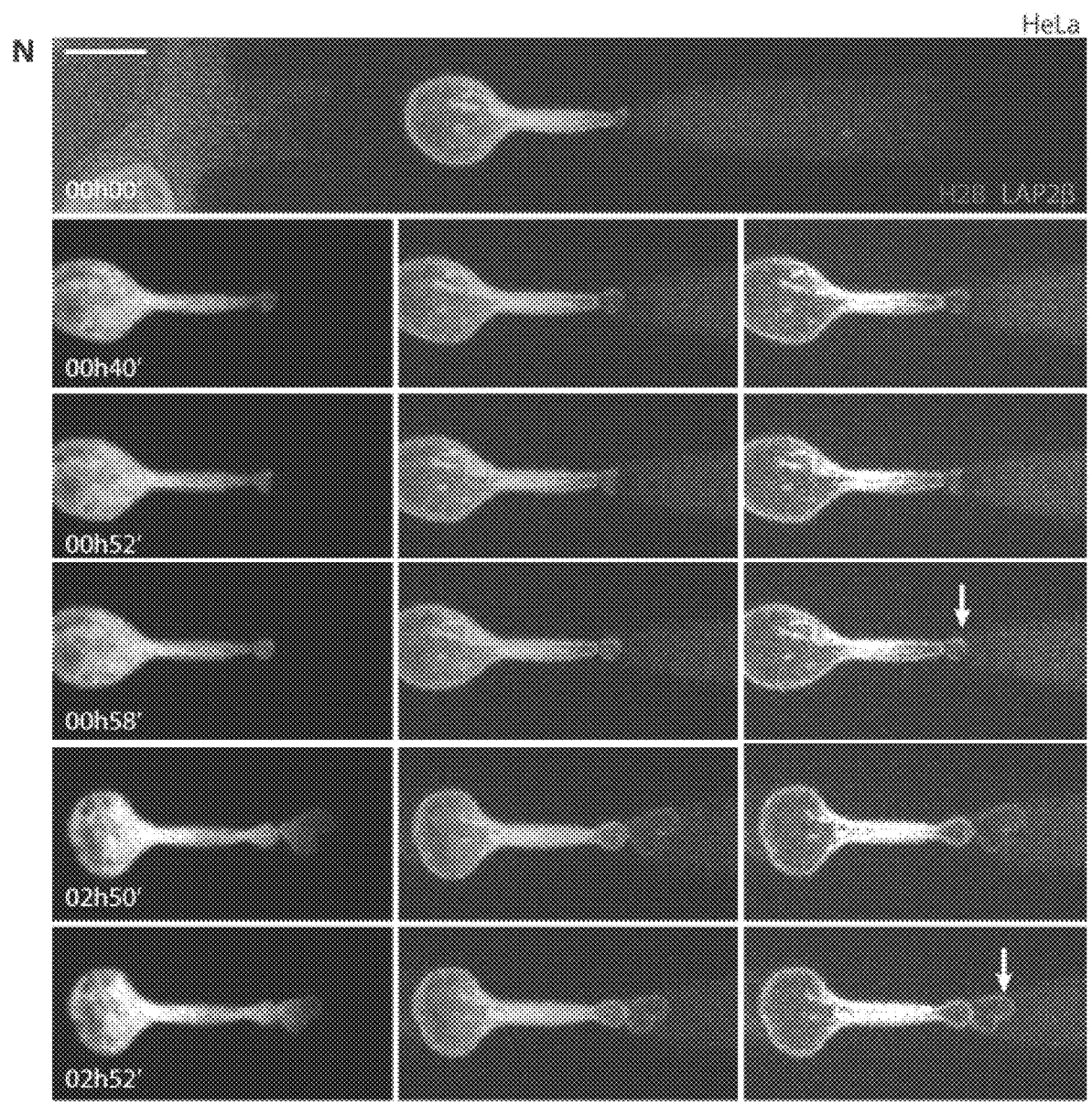
Figure 5:
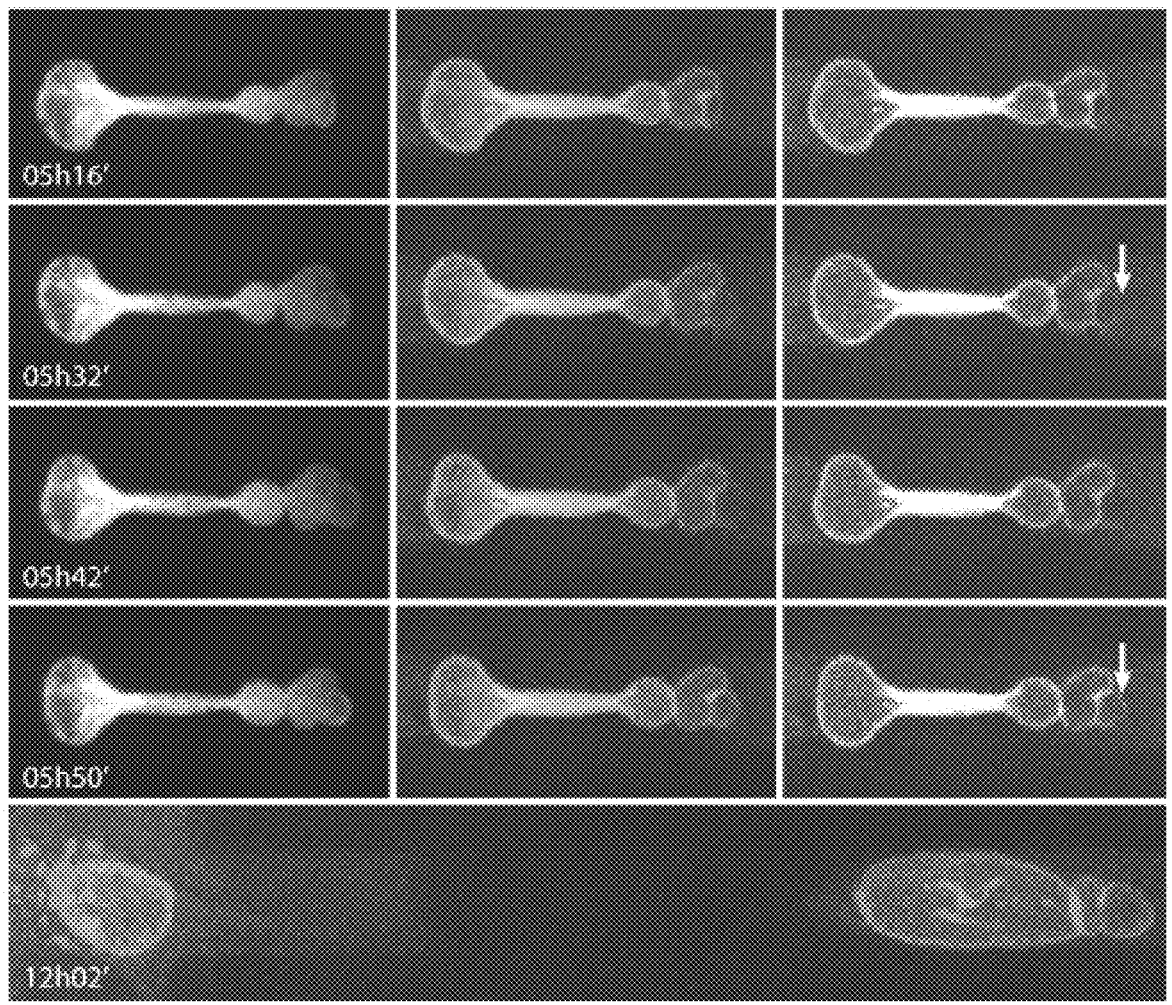

To better characterize the precise timing and location of nuclear envelope rupture, the inventors used cells expressing a cytoplasmic DNA binding probe fused to EGFP: EGFP-FLAG-cGAS in Hela and RPE1 cells and EGFP-FLAG-cGAS E225A/D227A in hDC cells.). The DNA was prestained with Hoechst. Upon compression of hDCs, nuclear blebs were induced, as has been observed previously in other cell types, indicated by the appearance of roundish dark regions lacking both Hoechst staining and EGFP-FLAG-cGAS E225A/D227A staining at the periphery of the compressed nuclei (arrows in FIG. 5F). Upon rupture of these blebs, EGFP-FLAG-cGAS E225A/D227A localized to chromatin (Hoechst stained region) at the exact location where the nuclear bleb had formed and ruptured (FIG. 5F). This showed that this construct could be used to detect the timing and locations of NE rupture events more precisely than the NLS-EGFP probe.

Using this new probe, the inventors confirmed that hDCs transiently opened their NE while migrating through a constriction (FIG. 2H), at a higher frequency (FIGS. 2I and 5G) and earlier in the constriction (FIGS. 2J and 5H) for the smaller dimensions (reaching >80%). Interestingly, ruptures were localized in most cases at the front tip of the deformed nucleus, where nuclear blebs were observed (FIG. 2D, SI). These observations were conserved across all cell types studied (hDCs, RPE1 and HeLa cells). Consistent with the observation of multiple consecutive blebs in slowly migrating HeLa cells (FIG. 2D), multiple rupture events were observed in these cells (FIG. 2K, L). Staining of NE components showed that the nuclear lamina also ruptured (FIG. 5J) and that nuclear pores were excluded from the rupture region at the tip of the nucleus (FIG. 5K). Recording Lap2 β-EGFP, which is an inner nuclear membrane protein that binds the nuclear lamina, together with H2B-mCherry, which labels chromatin, in slow migrating HeLa cells, confirmed that the nuclear envelope formed blebs that eventually ruptured (FIG. 5L). In some cases, threads of chromatin could extend in front of the nucleus, but the nuclear envelope eventually reformed around them (FIG. 5M). Multiple blebs on top of other blebs could also be observed (FIG. 5N). Together, these results indicate that nuclear deformation induces transient leakage of nuclear components into the cytoplasm and likewise cytoplasmic proteins into the nucleus, indicative of NE opening.

Because the nucleo-cytoplasmic barrier was resealed after the nucleus passed through the constriction (as assessed by NLS-EGFP signal nuclear relocalization to the nucleus, FIG. 2E), the inventors hypothesized that a specific mechanism might be involved. The inventors have previously shown that plasma membrane repair requires the ESCRT III complex and recent contributions have shown that it is also involved in resealing the nuclear envelope at the end of mitosis. The inventors therefore used cells co-expressing both CHMP4B-EGFP, an ESCRT III complex subunit, and the FLAG-cGAS probe fused to tagRFP. We used BAC HeLa cells, which express endogenous level of CHMP4B-EGFP, to avoid any artifacts from overexpression.

First, we observed that upon compression of these cells, CHMP4B-EGFP was recruited at the site of rupture of nuclear blebs, similarly to EGFP-FLAG-cGAS E225A/D227A (FIG. 5F). The inventors quantified that nearly all of the nuclear blebs (95% n=62) that burst subsequently recruited CHMP4B-EGFP, and they quantified the time from the burst until the ESCRT III recruitment to be 49±20 sec (n=34). Furthermore, using laser ablation aimed at the nuclear edge, the inventors could also induce recruitment of CHMP4B-EGFP, precisely along the edge of the nucleus, as observed with 3D reconstruction from confocal z-stacks, with a similar timing (48±9 sec, n=8) to that seen in the compression experiments.

Figure 3:
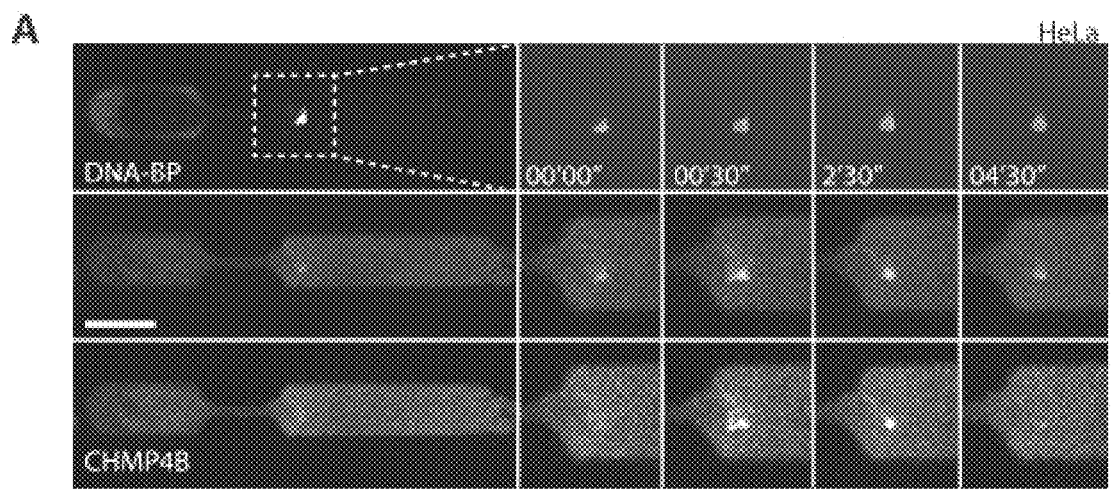
FIG. 3: ESCRT-III is involved in resealing the nuclear envelope during opening induced by nuclear constriction. (A) HeLa cell expressing CHMP4B-EGFP (green) and tagRFP-FLAG-cGAS (DNA-BP) (red/false color) migrating through a constriction (L=15 μm, w=2 μm). (B) Quantification corresponding to the first rupture event for the cell shown in (A) (C) Quantification of subsequent opening events as the nucleus continued to pass through the constriction for the cell shown in (A) (D) Time for rise to maximum intensity for tagRFP-FLAG-cGAS (DNA-BP) and CHMP4B-EGFP (n=7, N=2) (E) Time for onset of the first appearance of CHMP4B-EGFP accumulation at nuclear envelope for different types of opening events. Comparison is made to ESCRT-III recruitment to reseal plasma membrane (PM) indicated with * (numbers extracted from 17). Error bars are SEM (N=3 for compression and laser wounding, N=2 for constrictions) (F-H) RPE-1 cells expressing NLS-EGFP passing through constrictions (L=20 μm, w=3 μm), after various treatments with siRNA. (I-K) Quantification of NLS-EGFP localization in cells treated with control SiRNA (black curves) and with different SiRNAs (red curves). n>6 cells for each curve (N=2). Error bars are SEM. Scale bars are 20 μm.
Figure 3:
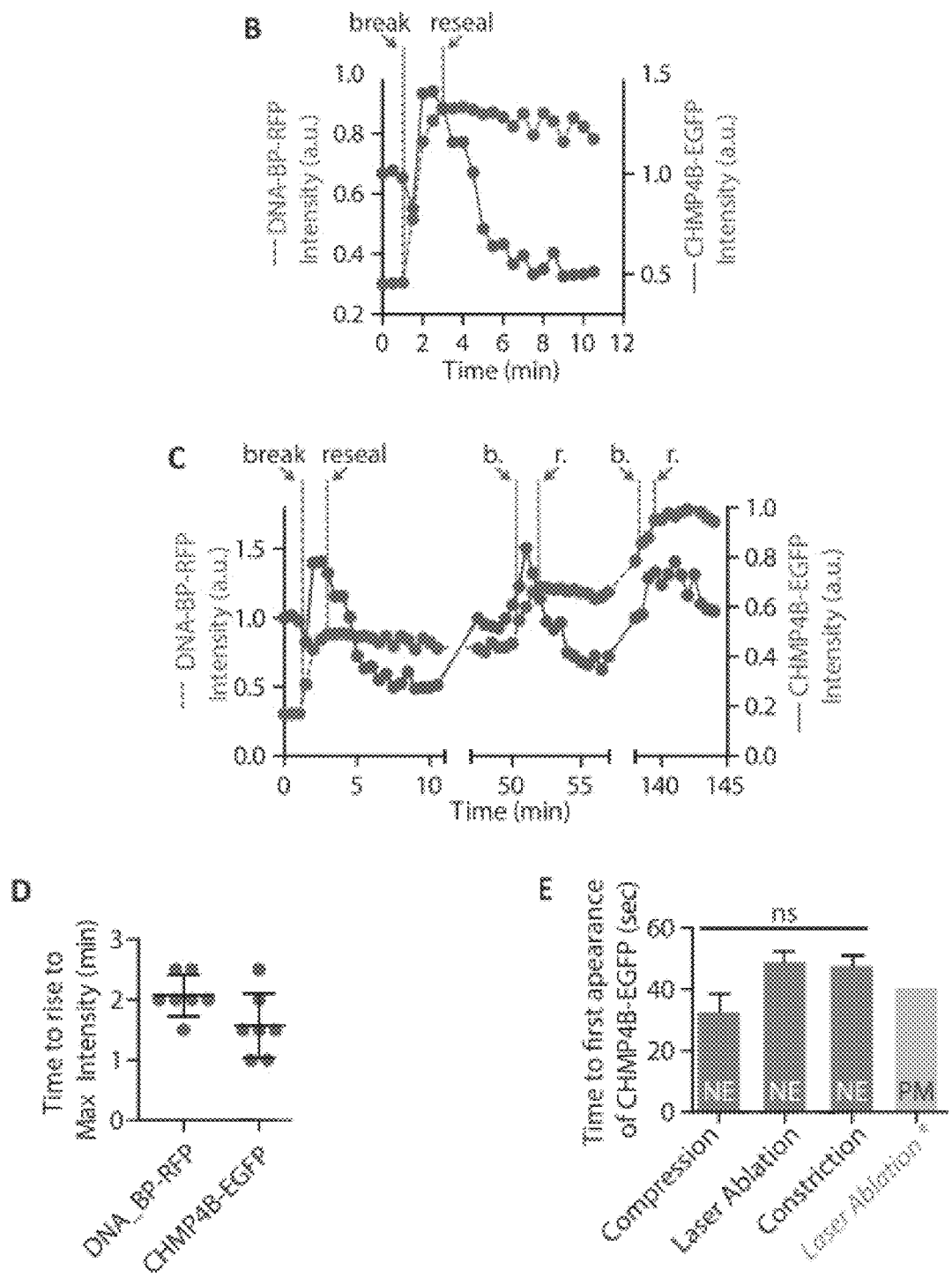
Figure 3:
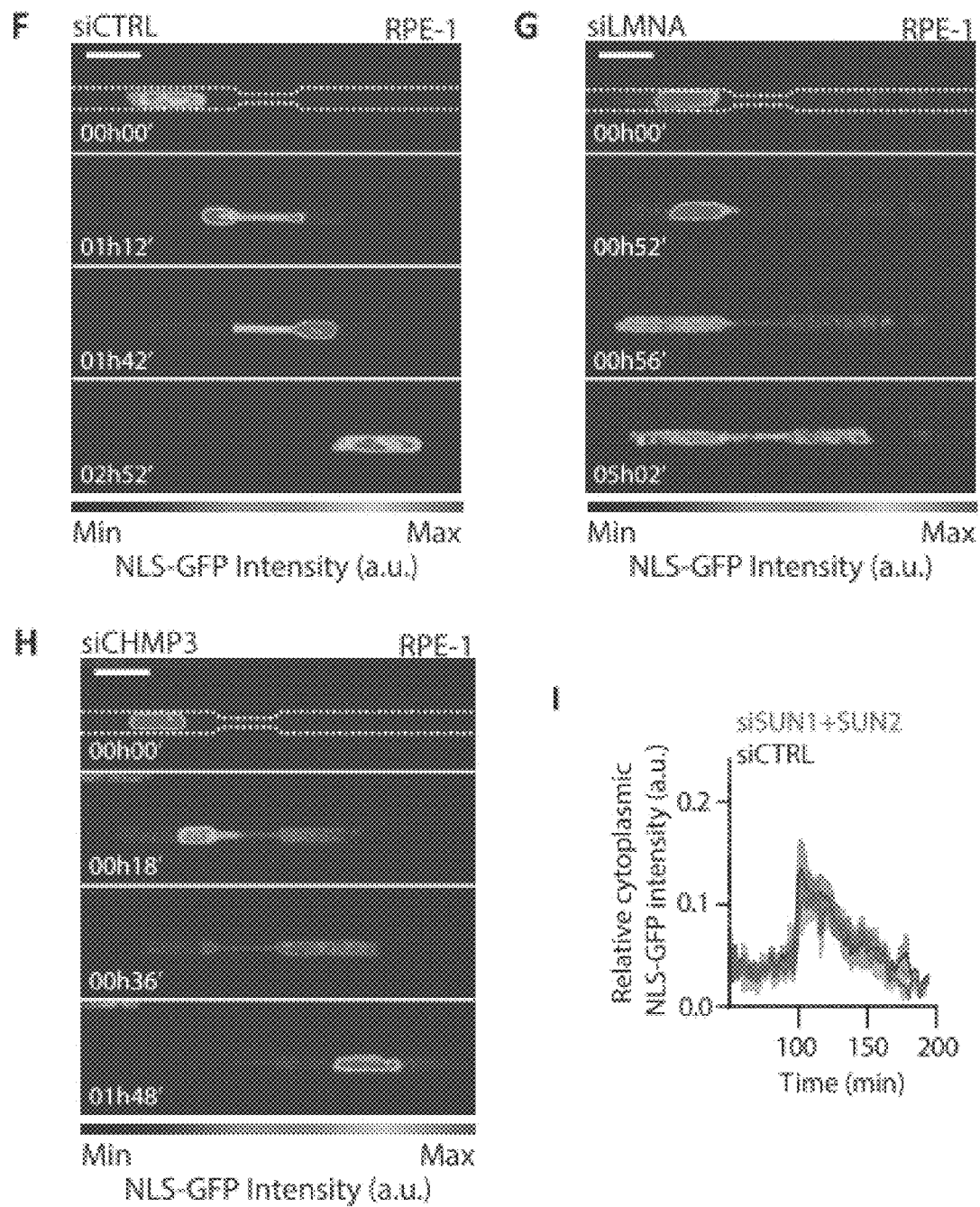
Figure 3:
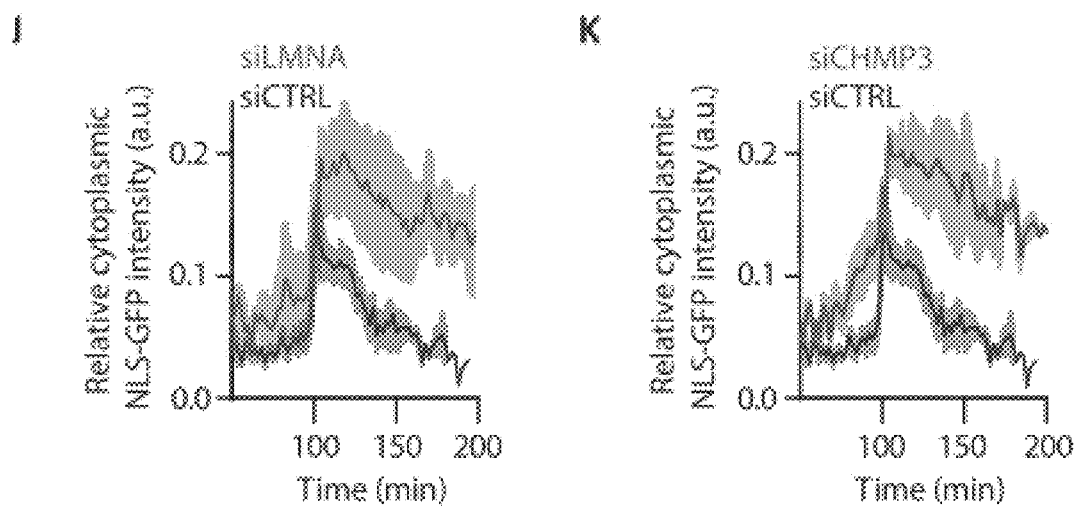

To correlate nucleo-cytoplasmic leakage with ESCRT III recruitment, the inventors then imaged HeLa cells, which migrate slowly through constrictions and break their nucleus multiple times. The inventors observed that CHMP4B-EGFP was transiently recruited to sites of tagRFP-FLAG-cGAS entry, at the nucleus tip (FIG. 3A). Quantifying the level of tagRFP-FLAG-cGAS in the nucleus allowed us to identify the precise timing of NE rupture (at the onset of the signal increase), and the timing of NE resealing (the plateauing of the tagRFP-FLAG-cGAS nuclear signal), for each rupture event (FIG. 3B). CHMP4B-EGFP localized to the site of NE rupture just after the rupture occurred, and decreased after resealing (FIG. 3A-D). Collectively, when inducing NE rupture with these 3 different methods (compression, laser and confined migration), the inventors found the kinetics for the recruitment of CHMP4B-EGFP to be similar to what they had previously observed after plasma membrane wounding (FIG. 3E). These experiments strongly suggested that, similarly to plasma membrane repair and nuclear envelope reformation at the end of mitosis, the resealing of the nuclear envelope after rupture due to nuclear deformation in migrating cells also requires the ESCRT III complex machinery.

To directly test the function of ESCRT III in NE resealing, the inventors knocked down CHMP3 in RPE1 cells expressing NLS-EGFP. This knockdown is known to induce a strong delay in nuclear envelope resealing after mitosis; it also delayed recruitment of CHMP4B-EGFP at the nuclear envelope of HeLa cells after laser wounding. The inventors also knocked down LMNA/C, whose depletion causes spontaneous NE rupture, and knocked down a combination of SUN1 and 2, inner nuclear envelope proteins whose depletion has not been reported to have such effect. As expected, we found that LMNA/C-depleted cells exhibited random bursts of NLS-EGFP from the nucleus into the cytoplasm even in the absence of nuclear constriction.

When these cells migrated through constrictions, and contrary to control cells (FIG. 3F), they incurred a complete loss of nuclear signal (FIG. 3G, note that the representative cell shown in FIG. 3G even undergoes apoptosis as the nucleus crosses the constriction, which is discussed later). Compared to control cells (black curves in FIG. 3I, J, K), they also took longer to recover the nuclear NLS-EGFP signal after passing the constriction (FIG. 3J). Conversely, cells depleted for both SUN1 and 2 showed no difference in NLS-EGFP localization compared with control cells (FIG. 3I). In contrast to LMNA/C-depleted cells, CHMP3-depleted cells did not show any leakage of NLS-EGFP in the cytoplasm when cells were outside constrictions, indicating that CHMP3 depletion did not make the nuclear envelope more susceptible to spontaneous rupture. However, when CHMP3-depleted cells passed through constrictions, they showed increased EGFP signal in the cytoplasm, like LMNA/C depleted cells, and the cytoplasmic signal remained for prolonged periods of time after the cells passed the constriction (FIG. 3H, K). Altogether, these experiments demonstrate that the ESCRT III complex, while not involved in maintaining the structural integrity of the nucleus, is essential to reseal the nuclear envelope after rupture induced by nuclear deformation in migrating cells.

The inventors hypothesized that efficient resealing was responsible for the high survival rate of cells passing through constrictions. The inventors thus quantified the occurrence of cell death after passage through a single constriction in RPE1 cells either depleted for LMNA/C, or for CHMP3. As expected from previous work by others, the inventors found a dramatic increase in death in LMNA/C-depleted cells (FIG. 4A), even inside straight channels, but stronger when cells were passing constrictions where the NE ruptured for longer periods of time. Conversely, CHMP3 depletion did not induce an increase in cell death even when cells were passing constrictions (FIG. 4A), showing that prolonged nuclear opening alone was not enough to cause cell death.

LMNA/C-depleted cells are known to exhibit defects in their DNA damage response. The inventors therefore imaged RPE-1 cells expressing 53BP1-EGFP, a protein recruited to DNA double strand breaks to mediate their repair. These cells showed a transient increase in the number and intensity of 53BP1-EGFP foci during passage of the nucleus through a constriction (FIG. 4B-D), indicating that DNA damage occurred following nuclear deformation during migration and was repaired after the nucleus exited the constriction. This rise and fall in the number and intensity of 53BP1-EGFP foci was reminiscent of the dynamics of NLS-EGFP cytoplasmic localization. This suggested that DNA double-stranded breaks might be caused by nuclear envelope opening.

Figure 4:
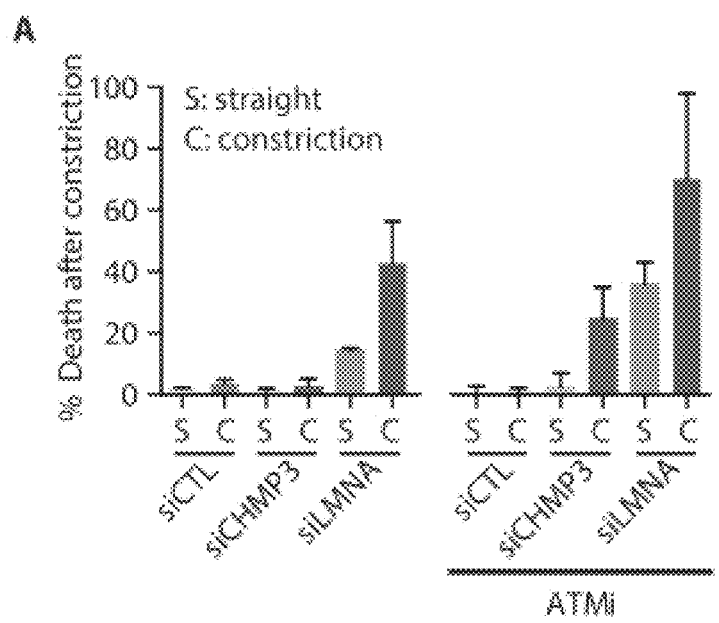
FIG. 4: DNA is broken and repaired in nuclei passing through constrictions, following nuclear envelope rupture. (A) Quantification of the fraction of RPE1 cells dying after passing one constriction. 'Straight' is the control for cells moving across the same distance in channels without constrictions (left to right, n=300, 300, 240, 240, 90, 90, 300, 300, 120, 60, 60, 60; N=3 for each condition) (B) RPE-1 cell expressing 53BP1-EGFP (grey) and tagRFP-FLAG-cGAS (DNA-BP) (red) migrating through a constriction (L=15 μm, w=2 µm). Red arrow indicates the point at which tagRFP-FLAG-cGAS (DNA-BP) begins to enter the nucleus. (C) Quantification of increase in the number of 53BP1-EGFP foci in the nucleus while passing a constriction (L=15 µm, w=1.5 µm). n=7 cells, N=3 (D) Total intensity of 53BP1-EGFP foci in nuclei passing constrictions (L=15 µm, w=1.5 µm). n=7 cells, N=3 (E) Quantification of increase in tagRFP-FLAG-cGAS (DNA-BP) intensity (red curve) inside the nucleus plotted with the increase in number of 53BP1-EGFP foci (black curve) for a representative cell. Inset dot plot: quantification of the time lag (Δt) between the first onset of tagRFP-FLAG-cGAS (DNA-BP) entering the nucleus and the first increase in number of 53BP1-EGFP foci. (F) Quantification of the number of 53BP1-EGFP foci in the nucleus of cells passing constrictions, for cells which showed entry of tagRFP-FLAG-cGAS (DNA-BP) in the nucleus (red curve, n=23) compared to cells which did not show entry of tagRFP-FLAG-cGAS (DNA-BP) (black curve, n=5 cells), for the same size of constrictions (L=15 µm, w=1.5 µm and 2 µm). N=3 (G) 53BP1-EGFP density profile in nuclei at different stages of passing constrictions. Density profiles were produced for nuclei i) before entering, ii) when the nuclear tip first reached the end of the constriction, iii) when the nucleus was halfway through the constriction, iv) after exiting the constriction (N=2). Constriction are (L=15 µm, w=2 µm). Error bars are SEM. Scale bars are 20 µm.
Figure 4:
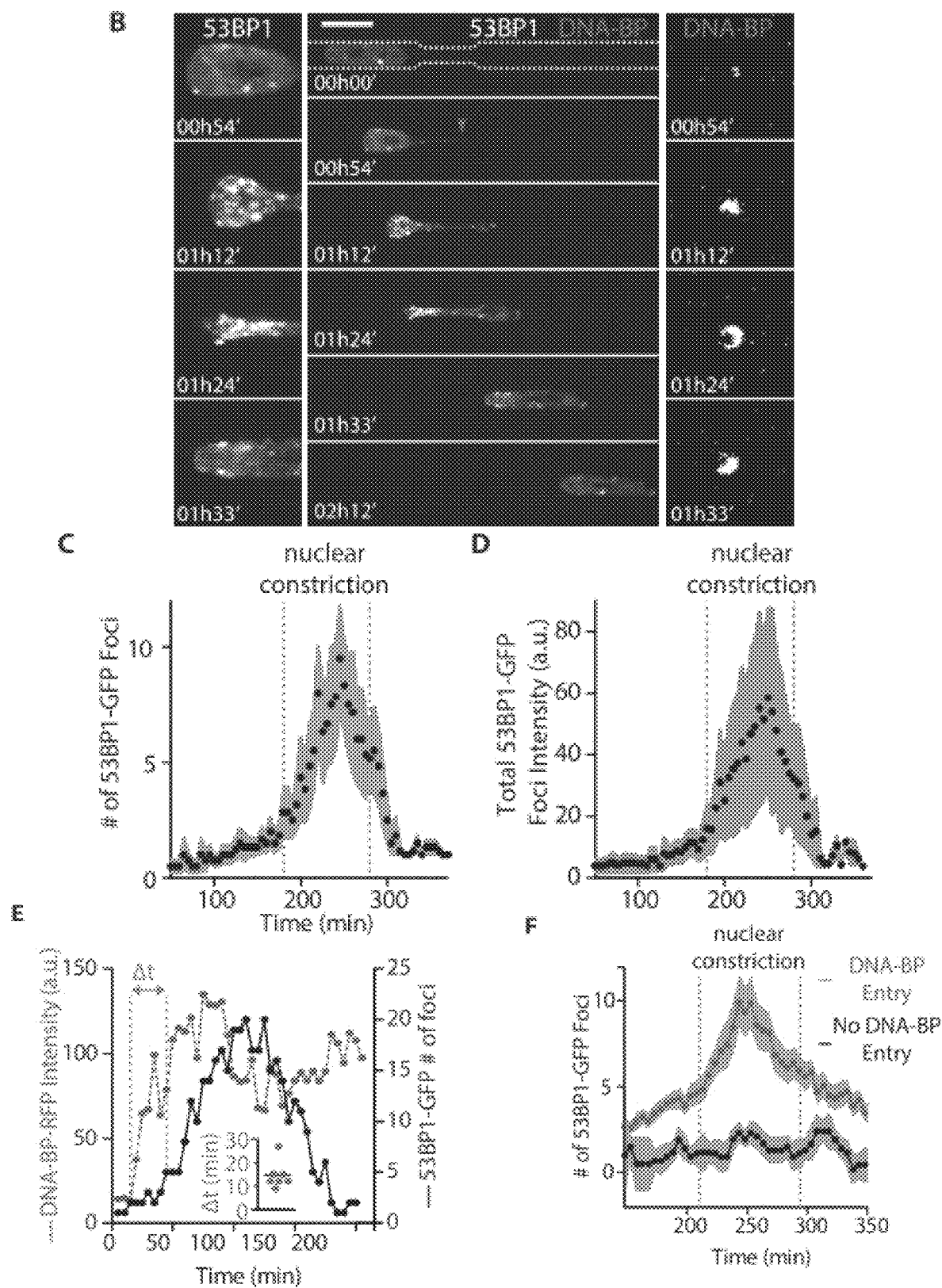
Figure 4:
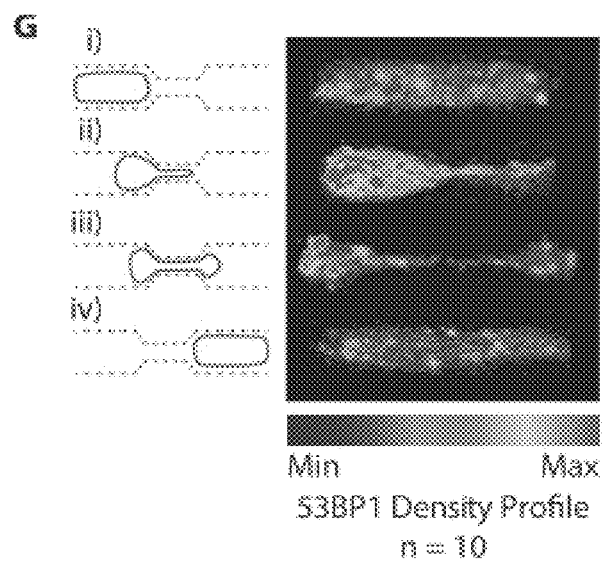

To test this, the inventors imaged cells expressing both 53BP1-EGFP and tagRFP-FLAG-cGAS, and found that the formation of 53BP1-EGFP foci always followed the recruitment of tagRFP-FLAG-cGAS into the nucleus (FIG. 4B, E). Furthermore, only cells that exhibited entry of tagRFP-FLAG-cGAS into the nucleus also showed an increase in 53BP1-EGFP (FIG. 4F). Interestingly, the 53BP1-EGFP foci were not restricted to the region of tagRFP-FLAG-cGAS staining at the nuclear front tip, the most deformed part of the nucleus, but were rather dispersed throughout the nucleus (FIG. 4G). This observation is not consistent with a direct mechanical effect of nuclear deformation on DNA breaks in the nucleus. Rather, it suggests that diffusing cytoplasmic factors enter during nuclear envelope rupture, and in turn induce DNA damage. In conclusion, these experiments show that nuclear envelope rupture in migrating cells induces the formation of DNA double strand breaks.

53BP1-EGFP foci rapidly disappeared when cells exited the constriction, suggesting efficient DNA repair. The inventors therefore hypothesized that the cell death observed upon migration through constrictions in LMNA/C-depleted cells could be caused by a defect in DNA repair combined with a high degree of DNA damage due to prolonged nuclear envelope opening. To test this hypothesis, the inventors inhibited DNA repair using an ATM inhibitor (ATMi, Fig S4E; 22), in control cells and in cells depleted for LMNA/C, or CHMP3. Upon ATMi treatment, the level of cell death was further increased in LMNA/C-depleted cells, and it reached about 30% in CHMP3-depleted cells, while this treatment had no effect on control cells or on CHMP3 depleted cells that did not migrate through constrictions (FIG. 4A). Together these experiments show that DNA damage due to prolonged nuclear envelope opening can lead to cell death provided that DNA repair is also reduced.

In summary, these results show that nuclear deformation during cell migration leads to transient opening of the NE, and that the ESCRT III complex is required for fast resealing. This transient opening leads to nucleo-cytoplasmic mixing, potentially causing DNA damage. Deciphering the precise mechanism by which nuclear deformation in migrating cells lead to NE opening would require further investigation, but our observations suggest the following model. Migrating cells, when facing a constriction, exert a force on their nucleus to deform it; this produces an increase in nuclear surface tension and in intra-nuclear pressure (as seen in experiments in which the nucleus is deformed by application of an external compression); increased intra-nuclear pressure leads to formation of nuclear envelope blebs (separation of the inner and outer NE membranes from the underlying nuclear lamina), which eventually rupture, inducing a transient leakage of nuclear proteins in the cytoplasm and likewise allow cytoplasmic proteins to enter the nucleus. The rupture of the double membrane would spontaneously lead to the formation of pores, to which ESCRT complex components would be recruited, leading to rapid sealing, similar to what happens at the end of mitosis during NE reformation or plasma membrane repair. The fact that similar mechanisms underlie membrane repair in these different contexts is consistent with the similar kinetics observed.

How would NE opening lead to DNA damage? The cell cytoplasm contains several enzymes that degrade DNA, some of which are involved in protection against cytoplasmic DNA, others in mitotic processing of chromatin. Mitotic control of the activity of these enzymes has been reported; this control prevents chromosomal damage after nuclear envelope breakdown at mitotic entry. But when such proteins are artificially engineered to accumulate in the nucleus in interphase cells, they induce a large number of DNA breaks. Upon opening of the nuclear envelope during cell migration through constrictions in interphase cells, such proteins could diffuse inside the nucleus and damage it. Alternatively, cytoplasmic ROS could have a similar effect. Support for this hypothesis comes from reports of massive DNA damage in micronuclei after nuclear envelope rupture, although the precise factors inducing this damage have not been identified. This makes DNA repair an essential process for the survival of cells migrating through dense environments, as they are constantly opening their NE. Consistent with this observation, highly migratory dendritic cells are known to have an elevated level of DNA repair machinery compared with their non-migratory precursors, and nuclear rupture induced by compression was shown to induce expression of genes associated with DNA repair.

The inventors propose that nuclear deformation in migrating cells, particularly in immune and cancer cells, causes transient rupture of their nuclear. As when cells exit mitosis, the ESCRT III complex is essential to ensure resealing of the nucleo-cytoplasmic barrier in migrating cells. The inventors anticipate that in various developmental, immunological or pathological contexts, nuclear-deformation-associated nuclear envelope rupture could lead to a large range of cellular responses. Such responses could have physiological functions, or lead to pathologies in the case of excessive nuclear envelope opening or defects in DNA repair.

Example 2

Figure 6:
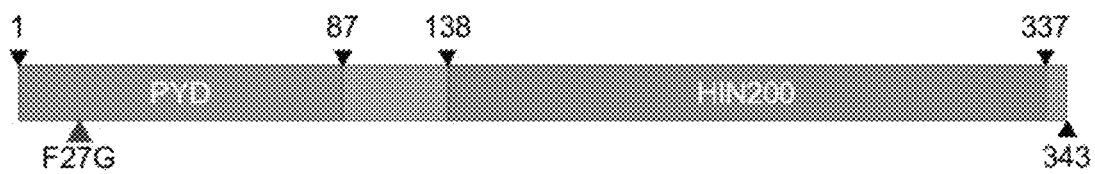
FIG. 6: (A) Schematic representation of the domains of human AIM2. The HIN200 domain binds DNA. The PYD domain activates inflammasome. To avoid inflammasome activation, the PYD domain carries the mutation F27G. EGFP is fused to the C-terminal of AIM2 with no linker. (B) Migration of human Monocyte Derived Dendritic Cells (MDDCs) transduced with AIM2 F27G-EGFP (SEQ ID NO: 10) in PDMS channels with constrictions (W: 2 µm, L: 5 µm). Top: AIM2 F27G-EGFP; Middle: siR-DNA; Bottom: DIC (Differential Interference Contrast). Scale bar is 10 µm.
Figure 6:
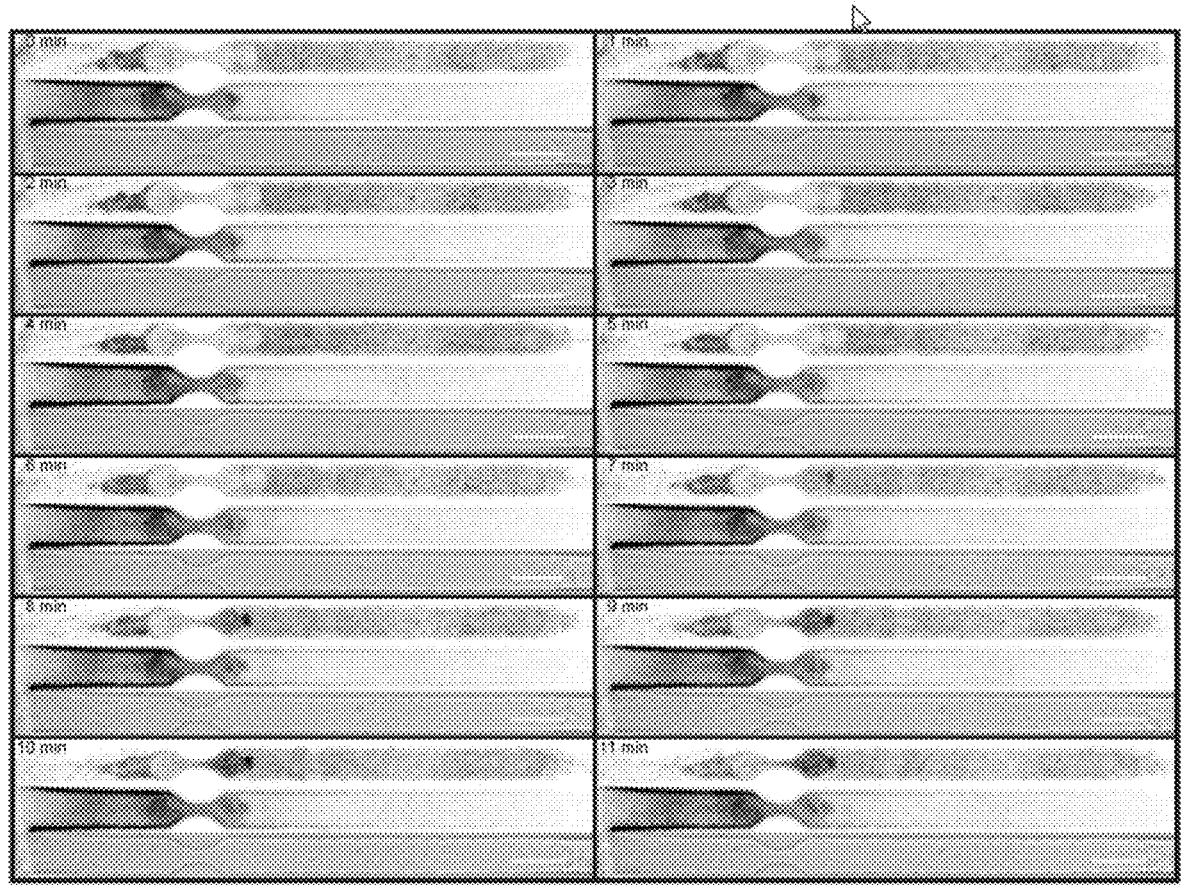

In addition to cGAS, AIM2 is also a cytosolic DNA sensor. AIM2 function is to activate the inflammasome (Hornung V et al, 2009, Nature, 458(7237):514-8). AIM2 binds DNA through its HIN200 domain and activates the inflammasome response thanks to protein-protein interactions through the PYD domain with the adaptor ASC. The inventors introduced the mutation F27G in the PYD domain to inactivate the capability of the sensor to activate the inflammasome response in the cell (Lu A et al, Cell, 2014, 156(6): 1193-1206), and they fused GFP to the C-terminal of the protein with no linker (cf. FIG. 6A). pTRIP-CMV-AIM2 F27G-EGFP (SEQ ID NO: 12) was then transduced in human monocyte derived dendritic cells (MDDCs) and migrated the cells in channels with constrictions. Before nuclear envelope rupture, a bleb devoid of DNA formed at the tip of the nucleus of the migrating cell, as shown in the EGFP channel in FIG. 6B until minute 6. Upon nuclear envelope rupture, at minute 7, EGFP accumulated at the tip of the nucleus where the DNA is now exposed. Therefore, cytosolic AIM2 can bind nuclear DNA upon nuclear envelope rupture and can be used to characterize such events.

Example 3

In order to study how nuclear envelope ruptures during interphase, the inventors focused on the main components of the nuclear cytoskeleton, the nuclear lamina and in particular on its main components A-Type Lamins (Lamin A/C) and B-Type Lamins (Lamin B1 and B2) (Burke B, Nat Rev Mol Cell Biol, 2013, 14(1):13-24).

Figure 7:
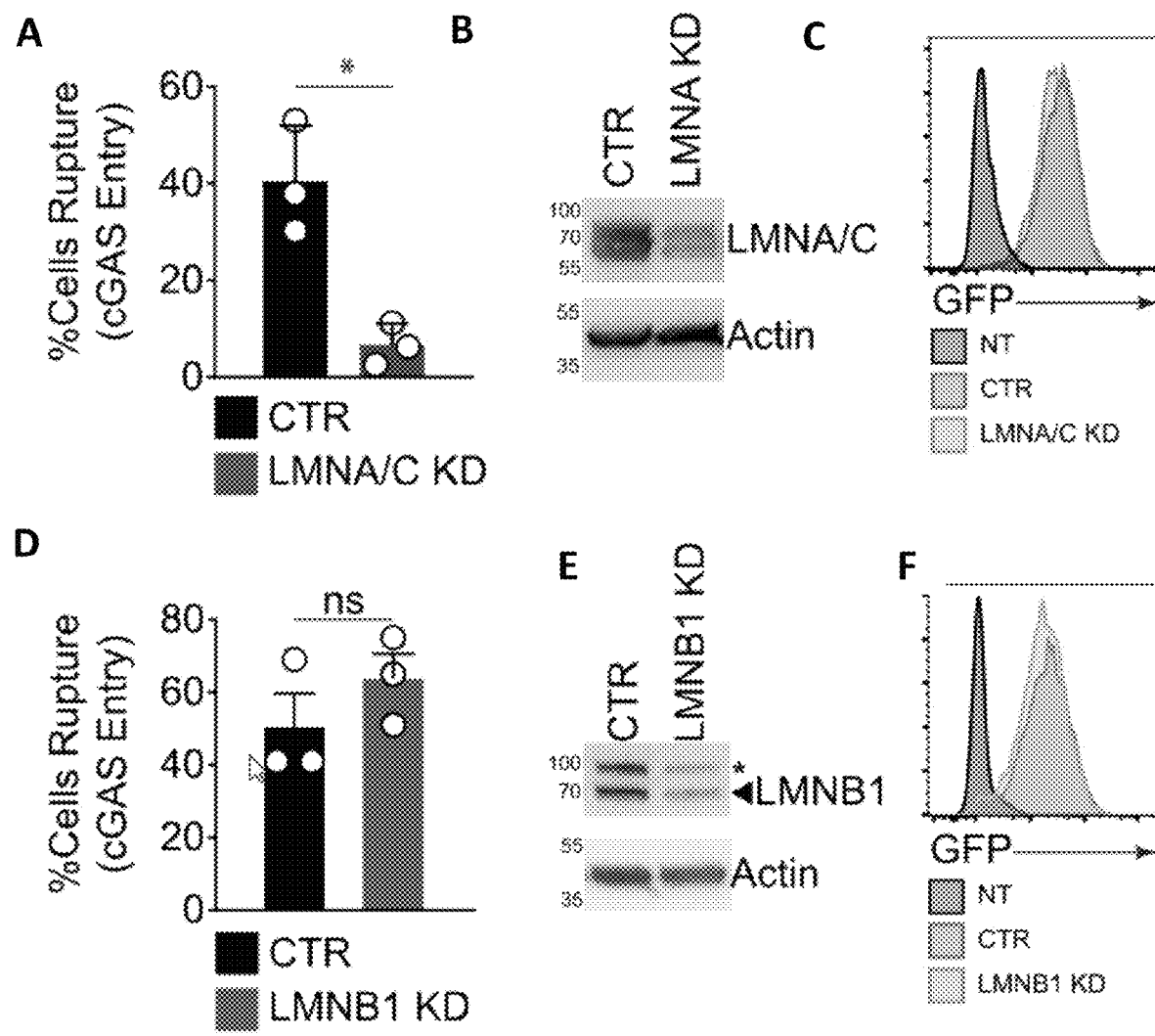
FIG. 7: (A) Percentage of control (CTR) or Lamin A/C (LMNA/C) knockdown MDDCs showing nuclear envelope ruptures while migrating in PDMS microchannels with constrictions (W: 3 µm, L: 15 µm). Nuclear envelope ruptures quantified as cells showing entry of EGFP-FLAG-cGAS E225A/D227A in nuclei. Paired t test, *p≤0.05. Each dot represents an independent donor. (B). Immunoblot of LMNA/C in control and knockdown MDDCs. One donor representative of three independent donors. (C). Histogram of EGFP-FLAG-cGAS E225A/D227A expression in non-transduced MDDCs (NT), control and LMNA/C KD MDDCs. One donor representative of three independent donors. (D). Percentage of control (CTR) or Lamin B1 (LMNB1) knockdown MDDCs showing nuclear envelope ruptures while migrating in PDMS microchannels with constrictions (W: 3 µm, L: 15 µm). Nuclear envelope ruptures quantified as cells showing entry of EGFP-FLAG-cGAS E225A/D227A in nuclei. Paired t test, ns=non-significant. Each dot represents an independent donor. (E). Immunoblot of LMNB1 in control and knockdown MDDCs. *: non-specific band; arrow indicate LMNB1. One donor representative of three independent donors. (F). Histogram of EGFP-FLAG-cGAS E225A/D227A expression in non-transduced MDDCs (NT), control and LMNA/C KD MDDCs. One donor representative of three independent donors.

The inventors first studied the impact of Lamin A/C depletion on nuclear envelope ruptures during cell migration. MDDCs expressing EGFP-FLAG-cGAS E225A/D227A (SEQ ID NO: 4) were knocked-down for Lamin A (cf. FIG. 7B), and migrated in channels with constrictions. Nuclear envelope ruptures were quantified by counting the cells showing EGFP-FLAG-cGAS E225A/D227A foci after migration through a constriction. MDDCs knock-down for Lamin A/C showed almost no nuclear envelope rupture upon migration in constrictions, as compared to control MDDCs (cf. FIG. 7A). Therefore, Lamin A/C is required for nuclear envelope ruptures in MDDCs.

The inventors then studied the impact of depletion of the other nuclear lamina component, Lamin B1. As before, MDDCs expressing EGFP-FLAG-cGAS E225A/D227A were knocked-down for Lamin B1 (cf. FIG. 7E) and migrated in channels with constriction. Opposed to Lamin A/C depletion, MDDCs knock-down for LMNB1 showed a modest but not significant increase in nuclear envelope ruptures events (cf. FIG. 7D). Therefore, opposed to Lamin A/C, Lamin B1 does not modulate nuclear envelope rupture events.

Those results also demonstrate that the in vitro method of the invention is able to screen or identify a compound capable of decreasing (e.g. Lamin A/C) or increasing (e.g. LMNB1) the frequency of interphase nuclear envelope rupture events in eukaryotic cells.

Example 4

In order to develop novel methods to detect nuclear envelope ruptures during interphase, the inventors adapted the SplitGFP system to their nuclear envelope ruptures sensor (Kamiyama D, Nat Commun, 2016; 7:11046). SplitGFP relies on sfGFP that has been split in two parts: GFP(1-10) which encode for the ß-sheets 1-10 of sfGFP, and GFP11, which encodes for the 11th ß-sheet of sfGFP. GFP (1-10) and GFP11 can be used to tag two different proteins or one protein and one organelle in cells. When spatially separated, GFP(1-10) and GFP11 do not fluoresce. On the contrary, when GFP(1-10) and GFP11 are put in close proximity, the full sfGFP is reconstituted and fluoresces. The inventors fused GFP(1-10) to Histone 2B (H2B), a nuclear protein, and GFP11 to cGAS E225A/D227A, which resides in the cytosol. If GFP11-FLAG-cGAS E225A/D227A (SEQ ID NO: 14) can access nuclear DNA, the GFP11 will reconstitute the full sfGFP and fluoresce.

Figure 8:
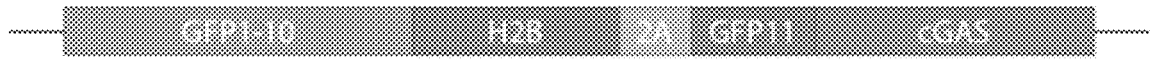
FIG. 8: (A). Schematic representation of the construct GFP(1-10)-H2B-P2A-GFP11-FLAG-cGAS. GFP(1-10) and GFP11 are two separate parts of sfGFP (super folder GFP) that when in close proximity reconstitute a full GFP molecule that fluoresces (PMID: 26988139, Kamiyama et al, 2016, Nat Commun, 7, 11046). One part of sfGFP, GFP(1-10)(B sheets 1-10), has been fused to Histone 2B (H2B), a nuclear protein. The other part of sfGFP, GFP11 (B sheet 11), has been fused to cGAS E225A/D227A, which is exclusively cytosolic. Upon nuclear envelope breakdown, GFP11-FLAG-cGAS E225A/D227A (SEQ ID NO: 14) can access the nuclear GFP(1-10)-H2B (SEQ ID NO: 16), and reconstitute the full sfGFP molecule that will fluoresce. (B). One representative MDDC, transduced with the construct in (A), before entering a constriction (W: 2 µm, L: 5 µm). Top: HOECHST; Middle: GFP; Bottom: DIC. Some background nuclear GFP signal is present. (C). One representative MDDC, transduced with the construct in (A), after passing a constriction (W: 2 µm, L: 5 µm). Top: HOECHST; Middle: GFP; Bottom: DIC. Notice the accumulation of GFP signal at the tip of the nucleus (arrow).
Figure 8:
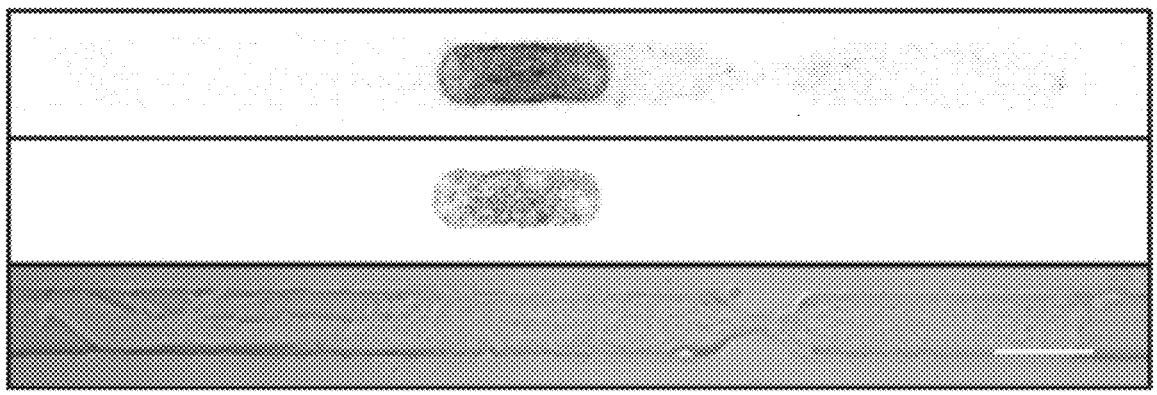
Figure 8:
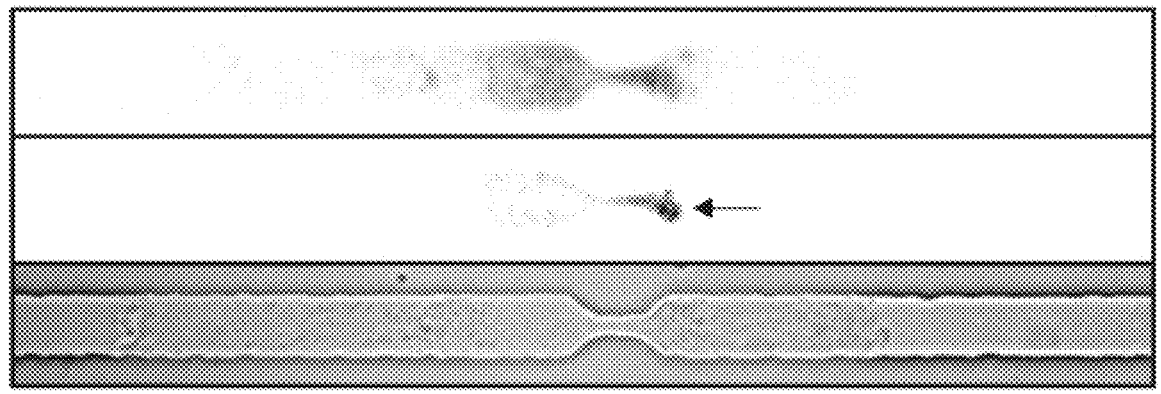

GFP(1-10)-H2B (SEQ ID NO: 15) and GFP11-FLAG-cGAS E225A/D227A (SEQ ID NO: 13) were cloned in a lentiviral vector interposing a P2A sequence between the two fusion proteins (cf. Figure. 8A). The inventors transduced MDDCs with this lentiviral vector (SEQ ID NO: 17), and migrated them in channels with constrictions. Before a constriction no GFP signal was observed in the cytosol (cf. FIG. 8B), indicating that GFP11-FLAG-cGAS E225A/D227A is not fluorescent in the absence of translocation into the nucleus. After an MDDC went through a constriction, GFP signal showed an accumulation at the tip of the nucleus. Therefore the SplitGFP system can be used to monitor nuclear envelope rupture events, and could be potentially implemented in a screening strategy based on imaging techniques or FACS.

The invention claimed is:

1. An in vitro method for screening or identifying a compound capable of increasing or decreasing the intensity and/or frequency of interphase nuclear envelope rupture events in eukaryotic cells comprising:
   (a) providing a eukaryotic cell expressing a protein fused to a detection entity and having a cytosolic non-nuclear localization in interphase and a non-sequence specific DNA binding activity; and
   (b) contacting said cell with a test compound;
   (c) measuring the intensity and/or frequency of the detection entity fused to said protein to detect presence of said protein in the nucleus of said cell, thereby measuring the intensity and/or frequency of interphase nuclear envelope rupture events in said cell, respectively; and
   (d) comparing the intensity and/or frequency of the presence of the detection entity fused to said protein in the nucleus of said cell with a reference level in the absence of said test compound and determining if said compound increases or decreases the intensity and/or frequency of the presence of the detection entity fused to said protein in the nucleus of said cell, thereby determining if said compound increases or decreases the intensity and/or frequency of said interphase nuclear envelope rupture events,
   wherein said protein is a human cGAS that has an E225A mutation or said protein is a human AIM2 that has a F27G mutation.

2. The method according to claim 1, wherein said method further comprises, after step d), a step of selecting the compound which increases or decreases the intensity and/or frequency of said interphase nuclear envelope rupture events.

3. The method according to claim 1, wherein said detection entity is selected from the group consisting of a tag, an enzyme and a fluorescent protein.

4. The method according to claim 1, wherein the intensity and/or frequency of the interphase nuclear envelope rupture events are measured on a population of between about 10 cells and between about 10,000,000 cells.

5. The method according to claim 1, wherein said protein is a human cGAS that has an E225A mutation.

6. The method according to claim 1, wherein said protein is a human AIM2 that has a F27G mutation.

7. The method according to claim 1, wherein the reference level is determined by measuring the intensity and/or frequency of the presence of the detection entity fused to said protein in the nucleus of said cell that is not contacted with said compound, thereby measuring the intensity and/or frequency of interphase nuclear envelope rupture events in said cell, respectively.

* * * * *

UNITED STATES PATENT AND TRADEMARK OFFICE
CERTIFICATE OF CORRECTION

PATENT NO. : 10,969,389 B2
APPLICATION NO. : 16/077744
DATED : April 6, 2021
INVENTOR(S) : Matthieu Piel et al.

Page 1 of 1

It is certified that error appears in the above-identified patent and that said Letters Patent is hereby corrected as shown below:

In the Specification

Column 30,
Line 2, "LAP2I3-EGFP" should read --LAP2β-EGFP--.

Column 34,
Line 64, "(FIG. 2D, SI)." should read --(FIG. 2D, 5I).--.

Signed and Sealed this
Thirtieth Day of November, 2021

Drew Hirshfeld
*Performing the Functions and Duties of the
Under Secretary of Commerce for Intellectual Property and
Director of the United States Patent and Trademark Office*